US010022434B2

(12) United States Patent
Weiner et al.

(10) Patent No.: US 10,022,434 B2
(45) Date of Patent: Jul. 17, 2018

(54) INFLUENZA NUCLEIC ACID MOLECULES AND VACCINES MADE THEREFROM

(71) Applicants: David B. Weiner, Merion, PA (US);
Jian Yan, Wallingford, PA (US);
Matthew Morrow, Bala Cynwyd, PA (US)

(72) Inventors: David B. Weiner, Merion, PA (US);
Jian Yan, Wallingford, PA (US);
Matthew Morrow, Bala Cynwyd, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 14/774,241

(22) PCT Filed: Mar. 12, 2014

(86) PCT No.: PCT/US2014/024363
§ 371 (c)(1),
(2) Date: Sep. 10, 2015

(87) PCT Pub. No.: WO2014/150835
PCT Pub. Date: Sep. 25, 2014

(65) Prior Publication Data
US 2016/0022806 A1    Jan. 28, 2016

Related U.S. Application Data

(60) Provisional application No. 61/787,182, filed on Mar. 15, 2013.

(51) Int. Cl.
| | | |
|---|---|---|
| *A61K 39/145* | (2006.01) | |
| *A61K 39/12* | (2006.01) | |
| *C07K 14/005* | (2006.01) | |
| *C12N 7/00* | (2006.01) | |
| *A61K 39/00* | (2006.01) | |

(52) U.S. Cl.
CPC ............ *A61K 39/145* (2013.01); *A61K 39/12* (2013.01); *C07K 14/005* (2013.01); *C12N 7/00* (2013.01); *A61K 2039/53* (2013.01); *A61K 2039/70* (2013.01); *C07K 2319/02* (2013.01); *C07K 2319/42* (2013.01); *C12N 2760/16022* (2013.01); *C12N 2760/16034* (2013.01); *C12N 2760/16041* (2013.01); *C12N 2760/16071* (2013.01); *C12N 2760/16122* (2013.01); *C12N 2760/16134* (2013.01); *C12N 2760/16222* (2013.01); *C12N 2760/16234* (2013.01); *C12N 2800/22* (2013.01)

(58) Field of Classification Search
None
See application file for complete search history.

(56) References Cited

U.S. PATENT DOCUMENTS

| | | |
|---|---|---|
| 8,298,820 B2 | 10/2012 | Weiner et al. |
| 9,192,660 B2 | 11/2015 | Weiner et al. |
| 2011/0177122 A1 | 7/2011 | Nabel et al. |
| 2011/0182938 A1 | 7/2011 | Weiner et al. |
| 2014/0286981 A1 | 9/2014 | Osorio et al. |

FOREIGN PATENT DOCUMENTS

| | | |
|---|---|---|
| JP | 2011-506272 A | 3/2011 |
| WO | 2010/036948 A2 | 4/2010 |
| WO | 2011/003100 A2 | 1/2011 |
| WO | 2011044152 A1 | 4/2011 |
| WO | 2012/047941 A2 | 4/2012 |
| WO | 2012061239 A2 | 5/2012 |
| WO | 2013/075266 A1 | 5/2013 |

OTHER PUBLICATIONS

GenBank: BAJ40882.1. hemagglutinin [Influenza A virus (A/Kobe/9154/2009(H1N1))]. Dated Dec. 3, 2010.*
GenBank: ACA28844.1. hemagglutinin [Influenza A virus (A/Brisbane/59/2007(H1N1))], dated May 9, 2008.*
Fang et al. Molecular characterization of in vivo adjuvant activity in ferrets vaccinated against influenza virus. J Virol. Sep. 2010;84(17):8369-88. Epub Jun. 9, 2010.*
GenBank: JN899402.1. Influenza A virus (A/Brisbane/59/2007(H1N1)) segment 4 hemagglutinin (HA) gene, complete cds. Dec. 28, 2011.*
Lee et al. Inactivated trivalent seasonal influenza vaccine induces limited cross-reactive neutralizing antibody responses against 2009 pandemic and 1934 PR8. H1N1 strainsVaccine 28 (2010) 6852-6857.*
Laddy et al., Heterosubtypic Protection against Pathogenic Human and Avian Influenza Viruses via in vivo electroporation of synthetic consensus DNA antigens. PLoS ONE 2008. 3(6): e2517; abstract.
Fagone et al. Molecular adjuvant HMGB1 enhances anti-influenza immunity during DNA vaccination. Gene Ther. 2011, 18(11): 1070-1077; Abstract, p. 4, Fig 5 and its legend.
Chen et al., "A consensus-hemagglutinin-based DNA vaccine that protects mice against divergent H5N1 influenza viruses", Proceedings of the National Academy of Sciences, vol. 105, No. 36, Sep. 9, 2008. pp. 13538-13543.

* cited by examiner

*Primary Examiner* — Nianxiang Zou
(74) *Attorney, Agent, or Firm* — Riverside Law LLP

(57) ABSTRACT

Provided herein are nucleic acid sequences that encode novel consensus amino acid sequences of HA hemagglutinin and/or influenza B hemagglutinin, as well as genetic constructs/vectors and vaccines expressing the sequences. Also provided herein are methods for generating an immune response against one or more influenza A serotypes and/or influenza B serotypes, or combinations thereof, using the vaccines that are provided.

15 Claims, 20 Drawing Sheets

Figure 1:
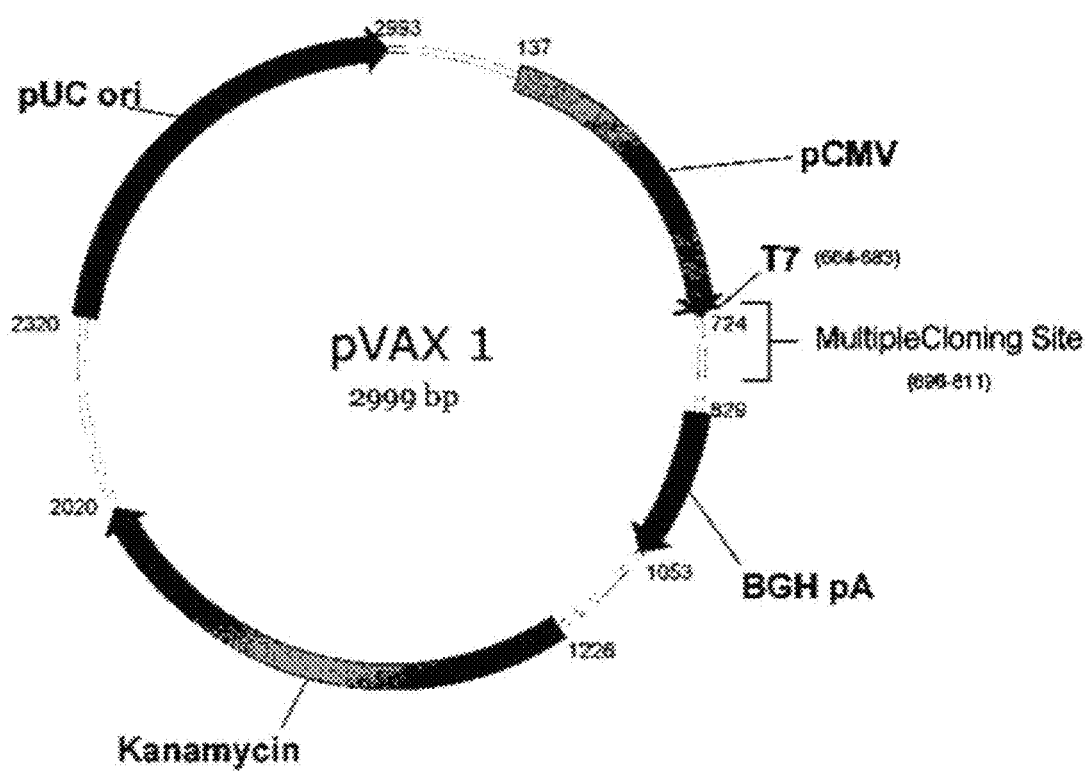

H1 tree of all viruses from last 20 years as well as South Carolina and where the constructs are located

FIGURE 6

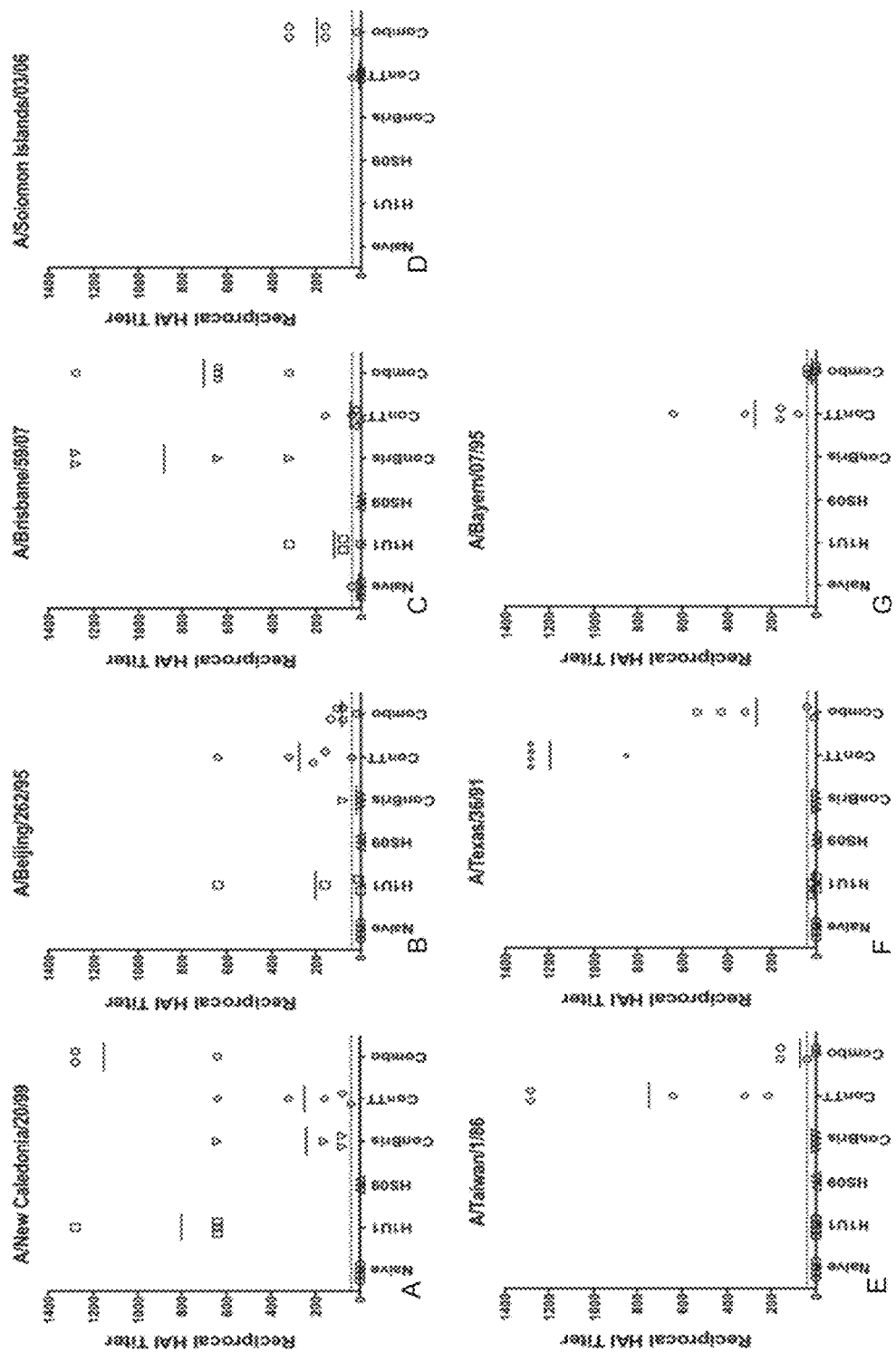
Mouse HAIs against seasonal viruses
FIGURES 7A-G

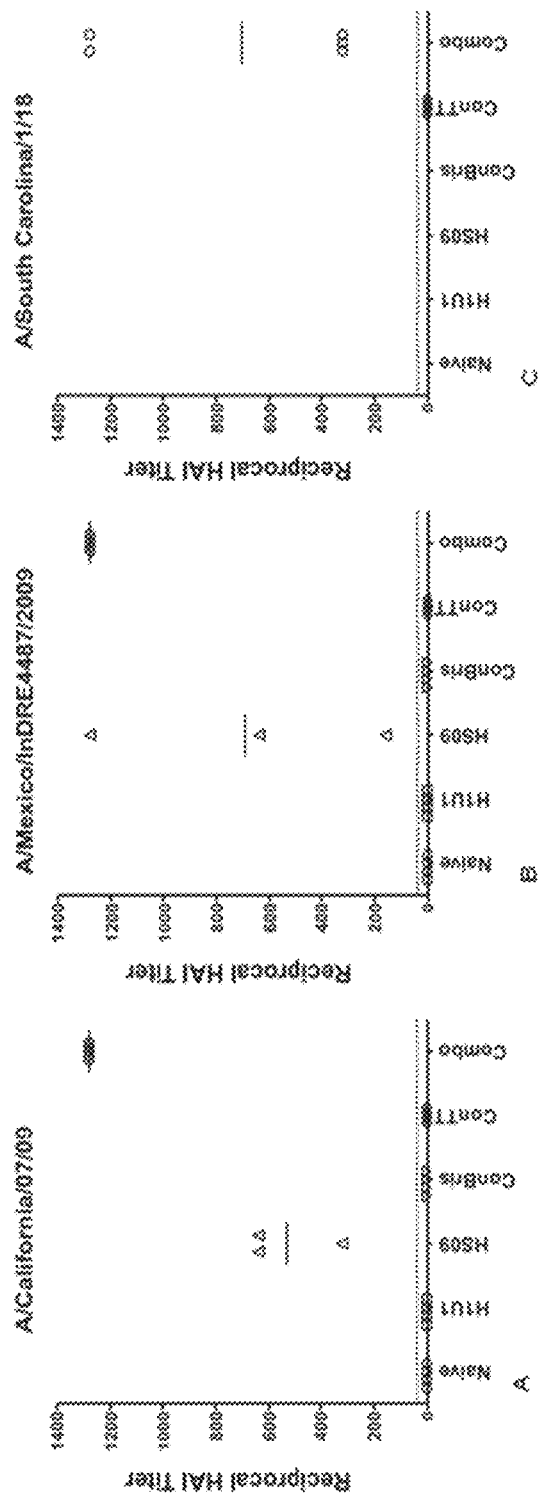
Mouse HAIs against pandemic viruses
FIGURES 8A-C

GUINEA PIGS COMBO VAX

GUINEA PIGS COMBO VAX

FERRETS VAX WITH HS09 & H1U, CHALLENGE STUDY

FIGURES 11A-C

FluB tree of all viruses from last 20 years and where the constructs are located

FIGURES 15A-D
GUINEA PIG DATA

GUINEA PIG DATA
FIGURES 16A-C

FIGURES 17A-C
GUINEA PIG DATA

Flu H3 tree of all viruses from last 20 years and where the constructs are located

FIGURE 18

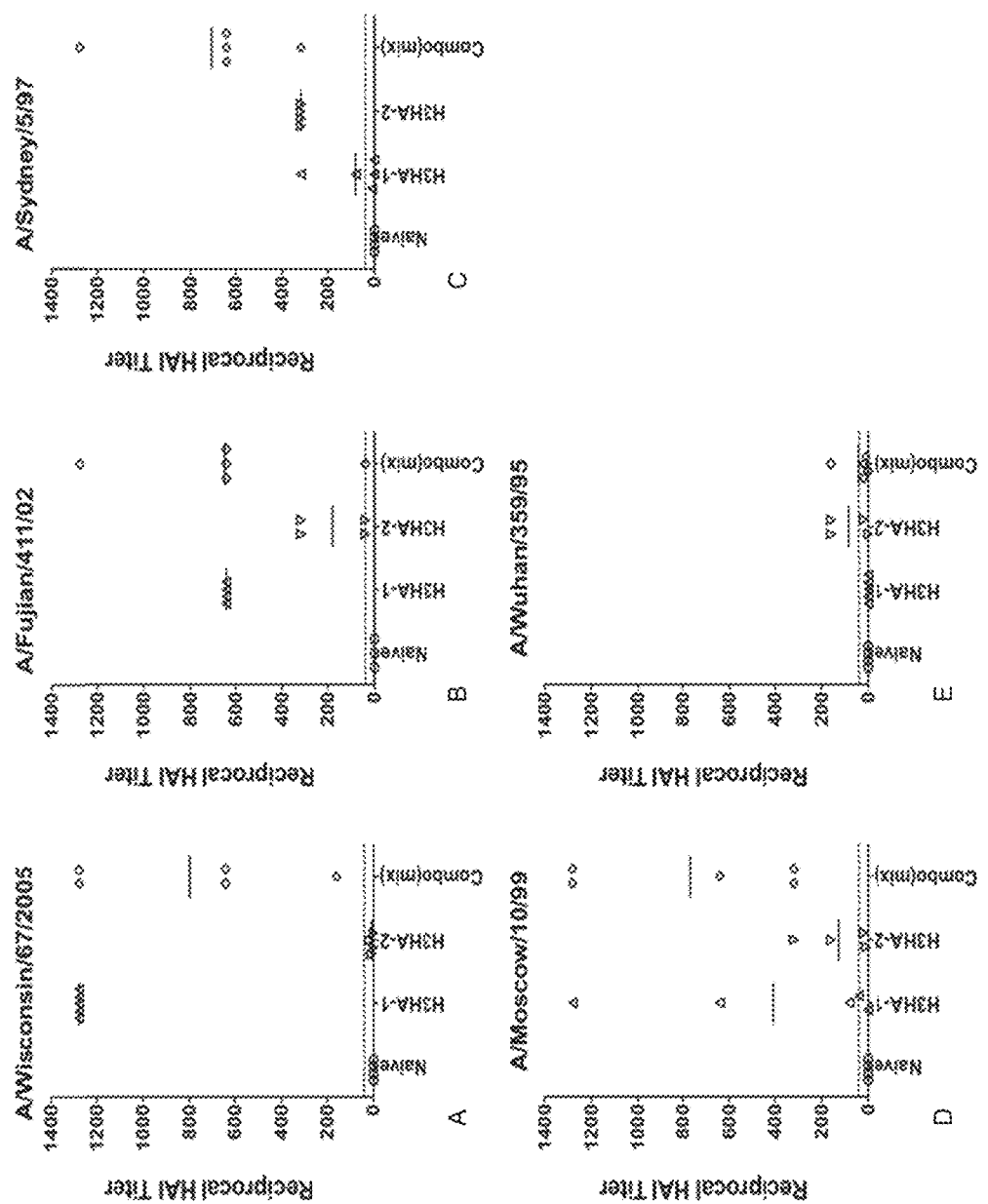
FIGURES 19A-E

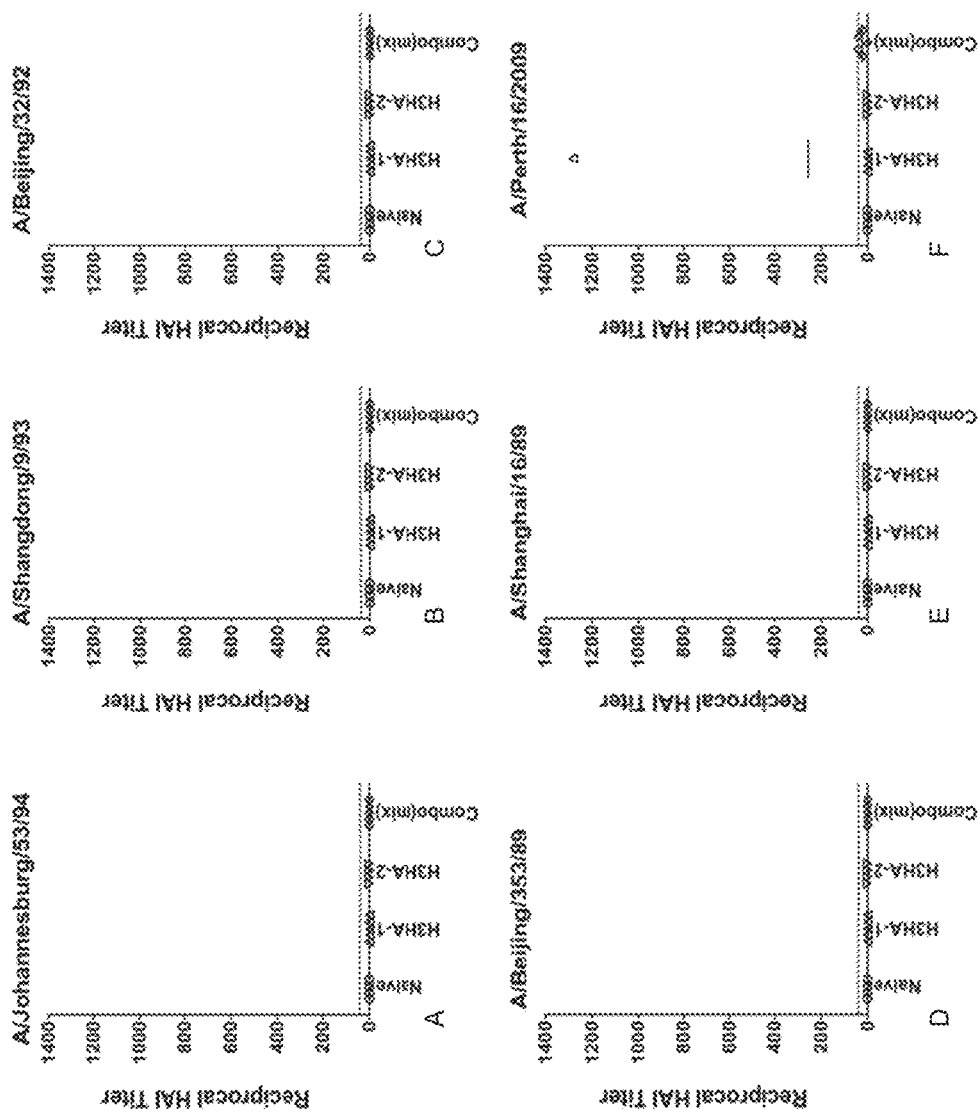
FIGURES 20A-F

```
                        SEQUENCE LISTING

<160> NUMBER OF SEQ ID NOS: 38

<210> SEQ ID NO 1
<211> LENGTH: 1695
<212> TYPE: DNA
<213> ORGANISM: Artificial Sequence
<220> FEATURE:
<223> OTHER INFORMATION: Influenza H1 DNA sequence

<400> SEQUENCE: 1
atgaaggcta tcctcgtcgt gctgctgtac accttcgcca ccgccaacgc cgatacccctg      60 tgcatcggct accacgccaa caacagcacc gacaccgtgg ataccgtgct ggaaaagaac     120
gtgaccgtga cccacagcgt gaacctgctg aagataagc acaacggcaa gctgtgcaag     180
ctgagaggcg tggcccctct gcacctgggc aagtgcaata tcgccggctg gattctgggc     240
aaccccgagt gcgagagcct gtctaccgct agctcctggt cctacatcgt ggagacaagc     300
agcagcgaca acggcacctg ttaccccggc gacttcatcg actacgagga actgcgggag     360
cagctgagca gcgtgtccag cttcgagcgg ttcgagatct cccccaagac cagctcctgg     420
cccaaccacg acagcaacaa gggcgtgacc gccgcctgtc ctcacgctgg cgccaagagc     480
ttctacaaga acctgatctg gctggtcaag aagggcaaca gctaccccaa gctgagcaag     540
agctacatca acgacaaggg caaagaggtc ctcgtcctct ggggcatcca ccaccctagc     600
accagcgccg accagcagag cctgtaccag aacgccgacg cctacgtgtt cgtgggctca     660
tctcggtaca gcaagaagtt caagcccgag atcgccatca gacccaaagt gcgggaccag     720
gaaggccgga tgaactacta ctggaccctg gtggagcccg gcgacaagat caccttcgag     780
gccaccggca atctggtggt gcccagatac gccttcgcca tggaaagaaa cgccggcagc     840
ggcatcatca tcagcgacac ccccgtgcac gactgcaaca ccacctgtca gacccccaag     900
ggcgccatca acaccagcct gcccttccag aacatccacc ccatcaccat cggcaagtgc     960
cctaagtacg tgaagtccac taagctcaga ctggccaccg gcctgagaaa cgtgcccagc    1020
atccagagca gaggcctgtt tggcgccatt gccggcttta tcgagggcgg ctggaccgga    1080
atggtggacg ggtggtacgg ctaccaccac cagaatgagc agggcagcgg ctacgccgcc    1140
gacctgaagt ccacacagaa cgccatcgac gagatcacca caaagtgaa cagcgtgatc    1200 gagaagatga acacccagtt caccgccgtg ggcaaagagt tcaaccacct ggaaaagcgg    1260
atcgagaacc tgaacaagaa ggtggacgac ggcttcctgg acatctggac ctacaacgcc    1320
gagctgctgg tgctgctgga aaacgagcgg accctggact accacgactc caacgtgaag    1380
aatctgtacg agaaagtgcg gagccagctg aagaacaacg ccaaagagat cggcaacggc    1440
tgcttcgagt tctaccacaa gtgcgacaac acctgtatgg aaagcgtgaa gaacggcacc    1500
tacgactacc caagtacag cgaggaagcc aagctgaacc gggaagagat cgacggcgtg    1560
aagctggaaa gcaccggat ctaccagatc ctggccatct actctactgt ggccagctca    1620
```

```
ctggtgctgg tggtgtccct gggcgccatc tccttttgga tgtgctccaa cggcagcctg   1680
cagtgccgga tctgc                                                    1695

<210> SEQ ID NO 2
<211> LENGTH: 566
<212> TYPE: PRT
<213> ORGANISM: Artificial Sequence
<220> FEATURE:
<223> OTHER INFORMATION: Influenza Protein H1 Sequence

<400> SEQUENCE: 2

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350
```

```
Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 3
<211> LENGTH: 1818
<212> TYPE: DNA
<213> ORGANISM: Artificial Sequence
<220> FEATURE:
<223> OTHER INFORMATION: IgE-H1-HAT Antigen DNA Sequence

<400> SEQUENCE: 3

```
ttaattaagg atccgccacc atggactgga cctggattct gttcctggtg gctgctgcca     60
ctagagtgca cagcatgaag gctatcctcg tcgtgctgct gtacaccttc gccaccgcca    120
acgccgatac cctgtgcatc ggctaccacg ccaacaacag caccgacacc gtggataccg    180
tgctggaaaa gaacgtgacc gtgacccaca gcgtgaacct gctggaagat aagcacaacg    240
gcaagctgtg caagctgaga ggcgtggccc ctctgcacct gggcaagtgc aatatcgccg    300
gctggattct gggcaacccc gagtgcgaga gcctgtctac cgctagctcc tggtcctaca    360
tcgtggagac aagcagcagc gacaacggca cctgttaccc cggcgacttc atcgactacg    420
aggaactgcg ggagcagctg agcagcgtgt ccagcttcga gcggttcgag atcttcccca    480
agaccagctc ctggcccaac cacgacagca acaagggcgt gaccgccgcc tgtcctcacg    540
ctggcgccaa gagcttctac aagaacctga tctggctggt caagaagggc aacagctacc    600
ccaagctgag caagagctac atcaacgaca agggcaaaga ggtcctcgtc ctctggggca    660
tccaccaccc tagcaccagc gccgaccagc agagcctgta ccagaacgcc gacgcctacg    720
tgttcgtggg ctcatctcgg tacagcaaga agttcaagcc cgagatcgcc atcagaccca    780
```

```
aagtgcggga ccaggaaggc cggatgaact actactggac cctggtggag cccggcgaca    840
agatcacctt cgaggccacc ggcaatctgg tggtgcccag atacgccttc gccatggaaa    900
gaaacgccgg cagcggcatc atcatcagcg acaccccgt gcacgactgc aacaccacct    960
gtcagacccc caagggcgcc atcaacacca gcctgccctt ccagaacatc caccccatca   1020
ccatcggcaa gtgccctaag tacgtgaagt ccactaagct cagactggcc accggcctga   1080
gaaacgtgcc cagcatccag agcagaggcc tgtttggcgc cattgccggc tttatcgagg   1140
gcggctggac cggaatggtg acgggtggt acggctacca ccaccagaat gagcagggca    1200
gcggctacgc cgccgacctg aagtccacac agaacgccat cgacgagatc accaacaaag   1260
tgaacagcgt gatcgagaag atgaacaccc agttcaccgc cgtgggcaaa gagttcaacc   1320
acctggaaaa gcggatcgag aacctgaaca agaaggtgga cgacggcttc ctggacatct   1380
ggacctacaa cgccgagctg ctggtgctgc tggaaaacga gcggaccctg gactaccacg   1440
actccaacgt gaagaatctg tacgagaaag tgcggagcca gctgaagaac aacgccaaag   1500
agatcggcaa cggctgcttc gagttctacc acaagtgcga caacacctgt atggaaagcg   1560
tgaagaacgg cacctacgac tacccccaagt acagcgagga agccaagctg aaccgggaag   1620
agatcgacgg cgtgaagctg gaaagcaccc ggatctacca gatcctggcc atctactcta   1680
ctgtggccag ctcactggtg ctggtggtgt ccctgggcgc catctccttt tggatgtgct   1740
ccaacggcag cctgcagtgc cggatctgca tctacccta cgacgtgccc gactacgcct   1800
gatgactcga ggcgcgcc                                                  1818

<210> SEQ ID NO 4
<211> LENGTH: 593
<212> TYPE: PRT
<213> ORGANISM: Artificial Sequence
<220> FEATURE:
<223> OTHER INFORMATION: IgE-H1-HATanitgen amino acid seqeunce

<400> SEQUENCE: 4

Met Asp Trp Thr Trp Ile Leu Phe Leu Val Ala Ala Thr Arg Val
1               5                   10                  15

His Ser Met Lys Ala Ile Leu Val Val Leu Leu Tyr Thr Phe Ala Thr
            20                  25                  30

Ala Asn Ala Asp Thr Leu Cys Ile Gly Tyr His Ala Asn Asn Ser Thr
        35                  40                  45

Asp Thr Val Asp Thr Val Leu Glu Lys Asn Val Thr Val Thr His Ser
    50                  55                  60

Val Asn Leu Leu Glu Asp Lys His Asn Gly Lys Leu Cys Lys Leu Arg
65                  70                  75                  80

Gly Val Ala Pro Leu His Leu Gly Lys Cys Asn Ile Ala Gly Trp Ile
                85                  90                  95

Leu Gly Asn Pro Glu Cys Glu Ser Leu Ser Thr Ala Ser Ser Trp Ser
            100                 105                 110

Tyr Ile Val Glu Thr Ser Ser Ser Asp Asn Gly Thr Cys Tyr Pro Gly
        115                 120                 125

Asp Phe Ile Asp Tyr Glu Glu Leu Arg Glu Gln Leu Ser Ser Val Ser
    130                 135                 140

Ser Phe Glu Arg Phe Glu Ile Phe Pro Lys Thr Ser Ser Trp Pro Asn
145                 150                 155                 160

His Asp Ser Asn Lys Gly Val Thr Ala Ala Cys Pro His Ala Gly Ala
                165                 170                 175
```

Lys Ser Phe Tyr Lys Asn Leu Ile Trp Leu Val Lys Lys Gly Asn Ser
                180                 185                 190

Tyr Pro Lys Leu Ser Lys Ser Tyr Ile Asn Asp Lys Gly Lys Glu Val
            195                 200                 205

Leu Val Leu Trp Gly Ile His His Pro Ser Thr Ser Ala Asp Gln Gln
        210                 215                 220

Ser Leu Tyr Gln Asn Ala Asp Ala Tyr Val Phe Val Gly Ser Ser Arg
225                 230                 235                 240

Tyr Ser Lys Lys Phe Lys Pro Glu Ile Ala Ile Arg Pro Lys Val Arg
                245                 250                 255

Asp Gln Glu Gly Arg Met Asn Tyr Tyr Trp Thr Leu Val Glu Pro Gly
            260                 265                 270

Asp Lys Ile Thr Phe Glu Ala Thr Gly Asn Leu Val Val Pro Arg Tyr
        275                 280                 285

Ala Phe Ala Met Glu Arg Asn Ala Gly Ser Gly Ile Ile Ile Ser Asp
290                 295                 300

Thr Pro Val His Asp Cys Asn Thr Thr Cys Gln Thr Pro Lys Gly Ala
305                 310                 315                 320

Ile Asn Thr Ser Leu Pro Phe Gln Asn Ile His Pro Ile Thr Ile Gly
                325                 330                 335

Lys Cys Pro Lys Tyr Val Lys Ser Thr Lys Leu Arg Leu Ala Thr Gly
            340                 345                 350

Leu Arg Asn Val Pro Ser Ile Gln Ser Arg Gly Leu Phe Gly Ala Ile
        355                 360                 365

Ala Gly Phe Ile Glu Gly Gly Trp Thr Gly Met Val Asp Gly Trp Tyr
370                 375                 380

Gly Tyr His His Gln Asn Glu Gln Gly Ser Gly Tyr Ala Ala Asp Leu
385                 390                 395                 400

Lys Ser Thr Gln Asn Ala Ile Asp Glu Ile Thr Asn Lys Val Asn Ser
                405                 410                 415

Val Ile Glu Lys Met Asn Thr Gln Phe Thr Ala Val Gly Lys Glu Phe
            420                 425                 430

Asn His Leu Glu Lys Arg Ile Glu Asn Leu Asn Lys Lys Val Asp Asp
        435                 440                 445

Gly Phe Leu Asp Ile Trp Thr Tyr Asn Ala Glu Leu Leu Val Leu Leu
450                 455                 460

Glu Asn Glu Arg Thr Leu Asp Tyr His Asp Ser Asn Val Lys Asn Leu
465                 470                 475                 480

Tyr Glu Lys Val Arg Ser Gln Leu Lys Asn Asn Ala Lys Glu Ile Gly
                485                 490                 495

Asn Gly Cys Phe Glu Phe Tyr His Lys Cys Asp Asn Thr Cys Met Glu
            500                 505                 510

Ser Val Lys Asn Gly Thr Tyr Asp Tyr Pro Lys Tyr Ser Glu Glu Ala
        515                 520                 525

Lys Leu Asn Arg Glu Glu Ile Asp Gly Val Lys Leu Glu Ser Thr Arg
530                 535                 540

Ile Tyr Gln Ile Leu Ala Ile Tyr Ser Thr Val Ala Ser Ser Leu Val
545                 550                 555                 560

Leu Val Val Ser Leu Gly Ala Ile Ser Phe Trp Met Cys Ser Asn Gly
                565                 570                 575

Ser Leu Gln Cys Arg Ile Cys Ile Tyr Pro Tyr Asp Val Pro Asp Tyr
            580                 585                 590

Ala

<210> SEQ ID NO 5
<211> LENGTH: 4739
<212> TYPE: DNA
<213> ORGANISM: Artificial Sequence
<220> FEATURE:
<223> OTHER INFORMATION: pGX2009 HS09 DNA sequence

<400> SEQUENCE: 5

| | |
|---|---|
| gctgcttcgc gatgtacggg ccagatatac gcgttgacat tgattattga ctagttatta | 60 |
| atagtaatca attacggggt cattagttca tagcccatat atggagttcc gcgttacata | 120 |
| acttacggta atggcccgc ctggctgacc gcccaacgac ccccgcccat tgacgtcaat | 180 |
| aatgacgtat gttcccatag taacgccaat agggactttc cattgacgtc aatgggtgga | 240 |
| gtatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc tctggctaac tagagaaccc actgcttact ggcttatcga | 660 |
| aattaatacg actcactata gggagaccca agctggctag cgtttaaact taagcttggt | 720 |
| accgagctcg gatccgccac catgactgg acctggattc tgttcctggt ggctgctgcc | 780 |
| actagagtgc acagcatgaa ggctatcctc gtcgtgctgc tgtacacctt cgccaccgcc | 840 |
| aacgccgata ccctgtgcat cggctaccac gccaacaaca gcaccgacac cgtggatacc | 900 |
| gtgctggaaa agaacgtgac cgtgacccac agcgtgaacc tgctggaaga taagcacaac | 960 |
| ggcaagctgt gcaagctgag aggcgtggcc cctctgcacc tggcaagtg caatatcgcc | 1020 |
| ggctggattc tgggcaaccc cgagtgcgag agcctgtcta ccgctagctc ctggtcctac | 1080 |
| atcgtggaga caagcagcag cgacaacggc acctgttacc ccggcgactt catcgactac | 1140 |
| gaggaactgc gggagcagct gagcagcgtg tccagcttcg agcggttcga gatcttcccc | 1200 |
| aagaccagct cctggcccaa ccacgacagc aacaagggcg tgaccgccgc ctgtcctcac | 1260 |
| gctggcgcca gagcttcta caagaacctg atctggctgg tcaagaaggg caacagctac | 1320 |
| cccaagctga gcaagagcta catcaacgac aagggcaaag aggtcctcgt cctctggggc | 1380 |
| atccaccacc ctagcaccag cgccgaccag cagagcctgt accagaacgc cgacgcctac | 1440 |
| gtgttcgtgg gctcatctcg gtacagcaag aagttcaagc ccgagatcgc catcagaccc | 1500 |
| aaagtgcggg accaggaagg ccggatgaac tactactgga ccctggtgga gcccggcgac | 1560 |
| aagatcacct tcgaggccac cggcaatctg gtggtgccca tacgccttc gccatggaa | 1620 |
| agaaacgccg gcagcggcat catcatcagc gacacccccg tgcacgactg caacaccacc | 1680 |
| tgtcagaccc ccaagggcgc catcaacacc agcctgccct tccagaacat ccaccccatc | 1740 |
| accatcggca gtgccctaa gtacgtgaag tccactaagc tcagactggc caccggcctg | 1800 |
| agaaacgtgc cagcatcca gagcagaggc ctgtttggcg ccattgccgg ctttatcgag | 1860 |
| ggcggctgga ccggaatggt ggacgggtgg tacggctacc accaccagaa tgagcagggc | 1920 |
| agcggctacg ccgccgacct gaagtccaca cagaacgcca tcgacgagat caccaacaaa | 1980 |
| gtgaacagcg tgatcgagaa gatgaacacc cagttcaccg ccgtgggcaa agagttcaac | 2040 |

```
cacctggaaa agcggatcga gaacctgaac aagaaggtgg acgacggctt cctggacatc    2100
tggacctaca acgccgagct gctggtgctg ctggaaaacg agcggaccct ggactaccac    2160
gactccaacg tgaagaatct gtacgagaaa gtgcggagcc agctgaagaa caacgccaaa    2220
gagatcggca acggctgctt cgagttctac cacaagtgcg acaacacctg tatggaaagc    2280
gtgaagaacg gcacctacga ctaccccaag tacagcgagg aagccaagct gaaccgggaa    2340
gagatcgacg gcgtgaagct ggaaaagcac cggatctacc agatcctggc catctactct    2400
actgtgggca gctcactggt gctggtggtg tccctgggcg ccatctcctt ttggatgtgc    2460
tccaacggca gcctgcagtg ccggatctgc atctacccct acgacgtgcc cgactacgcc    2520
tgatgactcg agtctagagg gcccgtttaa acccgctgat cagcctcgac tgtgccttct    2580
agttgccagc catctgttgt ttgcccctcc ccgtgccttc cttgaccct ggaaggtgcc    2640 actcccactg tccttttccta ataaaatgag gaaattgcat cgcattgtct gagtaggtgt    2700
cattctattc tggggggtgg ggtggggcag gacagcaagg gggaggattg gaagacaat    2760 agcaggcatg ctgggatgc ggtgggctct atggcttcta ctgggcggtt ttatggacag    2820
caagcgaacc ggaattgcca gctggggcgc cctctggtaa ggttgggaag ccctgcaaag    2880
taaactggat ggctttcttg ccgccaagga tctgatggcg caggggatca agctctgatc    2940
aagagacagg atgaggatcg tttcgcatga ttgaacaaga tggattgcac gcaggttctc    3000
cggccgcttg ggtggagagg ctattcggct atgactgggc acaacagaca atcggctgct    3060
ctgatgccgc cgtgttccgg ctgtcagcgc aggggcgccc ggttcttttt gtcaagaccg    3120
acctgtccgg tgccctgaat gaactgcaag acgaggcagc gcggctatcg tggctggcca    3180
cgacgggcgt tccttgcgca gctgtgctcg acgttgtcac tgaagcggga agggactggc    3240
tgctattggg cgaagtgccg gggcaggatc tcctgtcatc tcaccttgct cctgccgaga    3300
aagtatccat catggctgat gcaatgcggc ggctgcatac gcttgatccg gctacctgcc    3360
cattcgacca ccaagcgaaa catcgcatcg agcgagcacg tactcggatg aagccggtc    3420 ttgtcgatca ggatgatctg gacgaagagc atcaggggct cgcgccagcc gaactgttcg    3480
ccaggctcaa ggcgagcatg cccgacggcg aggatctcgt cgtgacccat ggcgatgcct    3540
gcttgccgaa tatcatggtg gaaaatggcc gcttttctgg attcatcgac tgtggccggc    3600
tgggtgtggc ggaccgctat caggacatag cgttggctac ccgtgatatt gctgaagagc    3660
ttggcggcga atgggctgac cgcttcctcg tgctttacgg tatcgccgct cccgattcgc    3720
agcgcatcgc cttctatcgc cttcttgacg agttcttctg aattattaac gcttacaatt    3780
tcctgatgcg gtattttctc cttacgcatc tgtgcggtat ttcacaccgc atcaggtggc    3840
acttttcggg gaaatgtgcg cggaacccct atttgtttat ttttctaaat acattcaaat    3900
atgtatccgc tcatgagaca ataaccctga taaatgcttc aataatagca cgtgctaaaa    3960
cttcattttt aatttaaaag gatctaggtg aagatccttt ttgataatct catgaccaaa    4020
atcccttaac gtgagttttc gttccactga gcgtcagacc ccgtagaaaa gatcaaagga    4080
tcttcttgag atcctttttt tctgcgcgta atctgctgct tgcaaacaaa aaaaccaccg    4140
ctaccagcgg tggtttgttt gccggatcaa gagctaccaa ctctttttcc gaaggtaact    4200
ggcttcagca gagcgcagat accaaatact gttcttctag tgtagccgta gttaggccac    4260
cacttcaaga actctgtagc accgcctaca tacctcgctc tgctaatcct gttaccagtg    4320
gctgctgcca gtggcgataa gtcgtgtctt accgggttgg actcaagacg atagttaccg    4380
gataaggcgc agcggtcggg ctgaacgggg ggttcgtgca cacagcccag cttggagcga    4440
```

| | | | |
|---|---|---|---|
| acgacctaca | ccgaactgag | atacctacag cgtgagctat gagaaagcgc cacgcttccc | 4500 |
| gaagggagaa | aggcggacag | gtatccggta agcggcaggg tcggaacagg agagcgcacg | 4560 |
| agggagcttc | cagggggaaa | cgcctggtat ctttatagtc ctgtcgggtt cgccacctc | 4620 |
| tgacttgagc | gtcgattttt | gtgatgctcg tcagggggc ggagcctatg gaaaaacgcc | 4680 |
| agcaacgcgg | ccttttacg | gttcctggcc ttttgctggc cttttgctca catgttctt | 4739 |

<210> SEQ ID NO 6
<211> LENGTH: 1719
<212> TYPE: DNA
<213> ORGANISM: Artificial Sequence
<220> FEATURE:
<223> OTHER INFORMATION: Influenza H2 antigen DNA sequence

<400> SEQUENCE: 6

| | | | |
|---|---|---|---|
| ggtaccaagc | ttgccaccat | ggccatcatc tacctgatcc tgctgttcac cgccgtgcgg | 60 |
| ggcgaccaga | tctgcatcgg | ctaccacgcc aacaacagca ccgagaaggt ggacaccatc | 120 |
| ctggaacgga | acgtgaccgt | gacccacgcc aaggacatcc tggaaaagac ccacaacggc | 180 |
| aagctgtgca | agctgaacgg | catcccccc ctggaactgg cgactgcag cattgccggc | 240 |
| tggctgctgg | gcaaccccga | gtgcgaccgg ctgctgtccg tgcccgagtg gagctacatc | 300 |
| atggaaaaag | agaaccccg | ggacggcctg tgctacccg gcagcttcaa cgactacgag | 360 |
| gaactgaagc | acctgctgtc | cagcgtgaag cacttcgaga aggtgaaaat cctgcccaag | 420 |
| gaccggtgga | cccagcacac | caccaccggc ggcagcagag cctgtgccgt gagcggcaac | 480 |
| cccagcttct | tccggaacat | ggtgtggctg accaagaagg gcagcaacta ccccgtggcc | 540 |
| aagggcagct | acaacaacac | ctccggagaa cagatgctga tcatctgggg cgtgcaccac | 600 |
| cccaacgacg | agacagagca | gcggaccctg taccagaacg tgggcaccta cgtgagcgtg | 660 |
| ggcaccagca | ccctgaacaa | gcggagcacc cccgagatcg ccacccgcc aaggtgaac | 720 |
| ggcctgggca | gccggatgga | attcagctgg accctgctgg acatgtggga caccatcaac | 780 |
| ttcgagagca | ccggcaacct | gatcgccccc gagtacggct tcaagatcag caagcggggc | 840 |
| agcagcggca | tcatgaaaac | cgagggcacc ctggaaaact gcgagacaaa gtgccagacc | 900 |
| cccctgggcg | ccatcaacac | caccctgccc ttccacaacg tgcacccct gaccatcggc | 960 |
| gagtgcccca | gtacgtgaa | gagcgagaag ctggtgctgg ccaccggcct gcggaacgtg | 1020 |
| ccccagatcg | agagcagggg | cctgttcggc gccattgccg gattcatcga gggcggctgg | 1080 |
| cagggcatgg | tggacgggtg | gtacggctac caccacagca acgaccaggg cagcggctac | 1140 |
| gccgccgaca | agagagcac | ccagaaggcc ttcgacggca tcaccaacaa ggtgaacagc | 1200 |
| gtgatcgaga | gatgaacac | ccagttcgag gccgtgggca agagttcag caacctggaa | 1260 |
| cggcggctgg | aaaacctgaa | caagaaaatg gaagatggct tcctggacgt gtggaccta c | 1320 |
| aacgccagc | tgctggtgct | gatggaaaac gagaggaccc tggacttcca cgacagcaac | 1380 |
| gtgaagaacc | tgtacgacaa | agtgcggatg cagctgcggg acaacgtgaa agagctgggc | 1440 |
| aacggctgct | tcgagttcta | ccacaagtgc gacgacgagt gcatgaactc cgtgaagaac | 1500 |
| ggcacctacg | actaccctaa | gtacgaggaa gagtccaagc tgaaccggaa cgagatcaag | 1560 |
| ggcgtgaagc | tgtccagcat | gggcgtgtac cagatcctgg ccatctacgc caccgtggcc | 1620 |
| ggcagcctga | gctggctat | tatgatggct ggcatcagct tttggatgtg cagcaacggc | 1680 |
| agcctgcagt | gccggatctg | catctgatga ctcgagctc | 1719 |

<210> SEQ ID NO 7
<211> LENGTH: 562
<212> TYPE: PRT
<213> ORGANISM: Artificial Sequence
<220> FEATURE:
<223> OTHER INFORMATION: Influenza H2 amino acid sequence

<400> SEQUENCE: 7
```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365
```

```
Asp Gln Gly Ser Gly Tyr Ala Ala Asp Lys Glu Ser Thr Gln Lys Ala
    370             375                 380
Phe Asp Gly Ile Thr Asn Lys Val Asn Ser Val Ile Glu Lys Met Asn
385                 390                 395                 400
Thr Gln Phe Glu Ala Val Gly Lys Glu Phe Ser Asn Leu Glu Arg Arg
                405                 410                 415
Leu Glu Asn Leu Asn Lys Lys Met Glu Asp Gly Phe Leu Asp Val Trp
            420                 425                 430
Thr Tyr Asn Ala Glu Leu Leu Val Leu Met Glu Asn Glu Arg Thr Leu
        435                 440                 445
Asp Phe His Asp Ser Asn Val Lys Asn Leu Tyr Asp Lys Val Arg Met
    450                 455                 460
Gln Leu Arg Asp Asn Val Lys Glu Leu Gly Asn Gly Cys Phe Glu Phe
465                 470                 475                 480
Tyr His Lys Cys Asp Asp Glu Cys Met Asn Ser Val Lys Asn Gly Thr
                485                 490                 495
Tyr Asp Tyr Pro Lys Tyr Glu Glu Ser Lys Leu Asn Arg Asn Glu
            500                 505                 510
Ile Lys Gly Val Lys Leu Ser Ser Met Gly Val Tyr Gln Ile Leu Ala
        515                 520                 525
Ile Tyr Ala Thr Val Ala Gly Ser Leu Ser Leu Ala Ile Met Met Ala
    530                 535                 540
Gly Ile Ser Phe Trp Met Cys Ser Asn Gly Ser Leu Gln Cys Arg Ile
545                 550                 555                 560
Cys Ile
```

<210> SEQ ID NO 8
<211> LENGTH: 4628
<212> TYPE: DNA
<213> ORGANISM: Artificial Sequence
<220> FEATURE:
<223> OTHER INFORMATION: pGX2006 H2HA DNA sequence

<400> SEQUENCE: 8

```
gactcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttgcc     720
accatggcca tcatctacct gatcctgctg ttcaccgccg tgcggggcga ccagatctgc     780
atcggctacc acgccaacaa cagcaccgag aaggtggaca ccatcctgga acggaacgtg     840
accgtgaccc acgccaagga catcctggaa aagacccaca acggcaagct gtgcaagctg     900
aacggcatcc ccccctggga actgggcgac tgcagcattg ccggctggct gctgggcaac     960
```

```
cccgagtgcg accggctgct gtccgtgccc gagtggagct acatcatgga aaaagagaac   1020
ccccgggacg gcctgtgcta ccccggcagc ttcaacgact acgaggaact gaagcacctg   1080
ctgtccagcg tgaagcactt cgagaaggtg aaaatcctgc ccaaggaccg gtggacccag   1140
cacaccacca ccggcggcag cagagcctgt gccgtgagcg gcaacccag cttcttccgg    1200
aacatggtgt ggctgaccaa gagggcagc aactaccccg tggccaaggg cagctacaac    1260
aacacctccg gagaacagat gctgatcatc tggggcgtgc accacccaa cgacgagaca    1320
gagcagcgga ccctgtacca gaacgtgggc acctacgtga gcgtgggcac cagcaccctg    1380
aacaagcgga gcaccccga gatcgccacc cggcccaagg tgaacggcct gggcagccgg    1440
atggaattca gctggaccct gctggacatg tgggacacca tcaacttcga gagcaccggc    1500
aacctgatcg cccccgagta cggcttcaag atcagcaagc ggggcagcag cggcatcatg    1560
aaaaccgagg gcaccctgga aaactgcgag acaaagtgcc agaccccct gggcgccatc    1620
aacaccaccc tgcccttcca caacgtgcac cccctgacca tcggcgagtg ccccaagtac    1680
gtgaagagcg agaagctggt gctggccacc ggcctgcgga acgtgcccca gatcgagagc    1740
aggggcctgt tcggcgccat tgccggattc atcgagggcg gctggcaggg catggtggac    1800
gggtggtacg gctaccacca cagcaacgac cagggcagcg gctacgccgc cgacaaagag    1860
agcacccaga aggccttcga cggcatcacc aacaaggtga acagcgtgat cgagaagatg    1920
aacacccagt tcgaggccgt gggcaaagag ttcagcaacc tggaacggcg gctggaaaac    1980
ctgaacaaga aaatggaaga tggcttcctg gacgtgtgga cctacaacgc cgagctgctg    2040
gtgctgatgg aaaacgagag gaccctggac ttccacgaca gcaacgtgaa gaacctgtac    2100
gacaaagtgc ggatgcagct gcgggacaac gtgaaagagc tggcaacgg ctgcttcgag    2160
ttctaccaca gtgcgacga cgagtgcatg aactccgtga agaacggcac ctacgactac    2220
cctaagtacg aggaagagtc caagctgaac cggaacgaga tcaagggcgt gaagctgtcc    2280
agcatgggcg tgtaccagat cctggccatc tacgccaccg tggccggcag cctgagcctg    2340
gctattatga tggctggcat cagctttttgg atgtgcagca acggcagcct gcagtgccgg    2400
atctgcatct gatgactcga gtctagaggg cccgtttaaa cccgctgatc agcctcgact    2460
gtgccttcta gttgccagcc atctgttgtt tgcccctccc ccgtgccttc cttgaccctg    2520
gaaggtgcca ctcccactgt cctttcctaa taaaatgagg aaattgcatc gcattgtctg    2580
agtaggtgtc attctattct ggggggtggg gtggggcagg acagcaaggg gaggattgg     2640
gaagacaata gcaggcatgc tggggatgcg gtgggctcta tggcttctac tgggcggttt    2700
tatggacagc aagcgaaccg gaattgccag ctggggcgcc ctctggtaag gttgggaagc    2760
cctgcaaagt aaactggatg gctttcttgc cgccaaggat ctgatggcgc aggggatcaa    2820
gctctgatca agagacagga tgaggatcgt ttcgcatgat tgaacaagat ggattgcacg    2880
caggttctcc ggccgcttgg gtggagaggc tattcggcta tgactgggca acagacaa     2940
tcggctgctc tgatgccgcc gtgttccggc tgtcagcgca ggggcgcccg gttctttttg    3000
tcaagaccga cctgtccggt gccctgaatg aactgcaaga cgaggcagcg cggctatcgt    3060
ggctggccac gacgggcgtt ccttgcgcag ctgtgctcga cgttgtcact gaagcgggaa    3120
gggactggct gctattgggc gaagtgccgg ggcaggatct cctgtcatct caccttgctc    3180
ctgccgagaa agtatccatc atggctgatg caatgcggcg gctgcatacg cttgatccgg    3240
ctacctgccc attcgaccac caagcgaaac atcgcatcga gcgagcacgt actcggatgg    3300
```

```
aagccggtct tgtcgatcag gatgatctgg acgaagagca tcaggggctc gcgccagccg   3360
aactgttcgc caggctcaag gcgagcatgc ccgacggcga ggatctcgtc gtgacccatg   3420
gcgatgcctg cttgccgaat atcatggtgg aaaatggccg ctttctgga ttcatcgact    3480 gtggccggct gggtgtggcg gaccgctatc aggacatagc gttggctacc cgtgatattg   3540
ctgaagagct tggcggcgaa tgggctgacc gcttcctcgt gctttacggt atcgccgctc   3600
ccgattcgca gcgcatcgcc ttctatcgcc ttcttgacga gttcttctga attattaacg   3660
cttacaattt cctgatgcgg tatttctcc ttacgcatct gtgcggtatt tcacaccgca    3720
tcaggtggca ctttcggggg aaatgtgcgc ggaaccccta tttgtttatt tttctaaata   3780
cattcaaata tgtatccgct catgagacaa taaccctgat aaatgcttca ataatagcac   3840
gtgctaaaac ttcattttta atttaaaagg atctaggtga agatccttt tgataatctc    3900 atgaccaaaa tcccttaacg tgagttttcg ttccactgag cgtcagaccc cgtagaaaag   3960
atcaaaggat cttcttgaga tcctttttt ctgcgcgtaa tctgctgctt gcaaacaaaa    4020
aaaccaccgc taccagcggt ggtttgtttg ccggatcaag agctaccaac tcttttccg    4080 aaggtaactg gcttcagcag agcgcagata ccaaatactg ttcttctagt gtagccgtag   4140
ttaggccacc acttcaagaa ctctgtagca ccgcctacat acctcgctct gctaatcctg   4200
ttaccagtgg ctgctgccag tggcgataag tcgtgtctta ccgggttgga ctcaagacga   4260
tagttaccgg ataaggcgca gcggtcgggc tgaacggggg gttcgtgcac acagcccagc   4320
ttggagcgaa cgacctacac cgaactgaga tacctacagc gtgagctatg agaaagcgcc   4380
acgcttcccg aagggagaaa ggcggacagg tatccggtaa gcggcagggt cggaacagga   4440
gagcgcacga gggagcttcc agggggaaac gcctggtatc tttatagtcc tgtcgggttt   4500
cgccacctct gacttgagcg tcgatttttg tgatgctcgt caggggggcg gagcctatgg   4560
aaaaacgcca gcaacgcggc ctttttacgg ttcctggcct tttgctggcc ttttgctcac   4620
atgttctt                                                           4628

<210> SEQ ID NO 9
<211> LENGTH: 1695
<212> TYPE: DNA
<213> ORGANISM: Artificial Sequence
<220> FEATURE:
<223> OTHER INFORMATION: Influenza U2 DNA sequence

<400> SEQUENCE: 9
aaggccaagc tgctggtgct gctgtgcacc ttcgccgcca ccaacgccga caccatctgc     60
atcggctacc acgccaacaa cagcaccgac accgtggata ccgtgctgga aaagaacgtg    120
accgtgaccc acagcgtgaa cctgctggaa gataagcaca acggcaagct gtgcaagctg    180
aagggaatcg cccccctgca gctgggcaag tgcaatatcg ccggctggat tctgggcaac    240
cccgagtgcg agagcctgag cagcaagagc agctggtcct acatcgtgga acccccaac     300 agcgagaacg gcacctgtta ccccggcgac ttcgccgact acgaggaact gcgcgagcag    360
ctgagcagcg tgtccagctt cgagagattc gagatcttcc ccaagaccag cagctggccc    420
aaccacgacg tgaccaaggg cgtgaccgct agctgtagcc acgcaggcgc cagcagcttc    480
tacaagaacc tgctgtggct gaccaagaag aacggcagct accccaagct gagcaagagc    540
tacatcaaca acaaagaaaa agaggtgctg gtcctctggg gcgtccacca ccccagcaca    600
atcgccgacc agcagagcct gtaccagaac gagaacgcct acgtgtccgt gggcagcagc    660
cactacagcc ggaagttcac ccccgagatc gccaagcggc ccaaagtgcg ggaccaggaa    720
```

```
ggccggatca actactactg gaccctgctg aacccggcg acaccatcat cttcgaggcc      780
aacggcaacc tgatcgcccc cagatacgcc ttcgccctga gcagaggctt cggcagcggc      840
atcatcatca gcaacgcccc catgcacgac tgcgacacca gtgccagac ccctcagggc       900 gccatcaaca gcagcctgcc cttccagaac atccaccccg tgaccatcgg cgagtgcccc      960
aaatacgtgc ggagcaccaa gctgcggatg gccaccggcc tgcggaacat ccccagcatc     1020
cagagcagag gcctgttcgg cgccattgcc ggcttcatcg agggcggctg gaccggaatg     1080
gtggacgggt ggtacggcta ccaccaccag aatgagcagg gcagcggcta cgccgccgac     1140
cagaagtcca cccagaacgc catcgacggc atcaccaaca agtgaacag cgtgatcgag      1200 aagatgaaca cccagttcac cgccgtgggc aaagagttca acaagctgga aaagcggatg     1260
gaaaacctga caagaaggt ggacgacggc ttcctggaca tctggaccta caacgccgaa      1320
ctgctcgtgc tgctggaaaa cgagcggacc ctggacttcc acgacagcaa cgtgaagaac     1380
ctgtacgaga agtgaagtc ccagctgaag aacaacgcca agagatcgg caacggctgc       1440 ttcgagttct accacaagtg caacaacgag tgcatggaaa gcgtgaagaa cggaacctac     1500
gactacccca gtacagcga ggaaagcaag ctgaaccggg aagagatcga cggcgtgaag      1560
ctggaatcca tgggcgtgta ccagatcctg gccatctaca gcaccgtggc tagcagcctg     1620
gtgctgctgg tgtccctggg cgccatctcc ttttggatgt gctccaacgg cagcctgcag    1680
tgccggatct gcatc                                                    1695
```

<210> SEQ ID NO 10
<211> LENGTH: 565
<212> TYPE: PRT
<213> ORGANISM: Artificial Sequence
<220> FEATURE:
<223> OTHER INFORMATION: Influenza U2 amino acid sequence

<400> SEQUENCE: 10

```
Lys Ala Lys Leu Leu Val Leu Leu Cys Thr Phe Ala Ala Thr Asn Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45

Leu Glu Asp Lys His Asn Gly Lys Leu Cys Lys Leu Lys Gly Ile Ala
    50                  55                  60

Pro Leu Gln Leu Gly Lys Cys Asn Ile Ala Gly Trp Ile Leu Gly Asn
65                  70                  75                  80

Pro Glu Cys Glu Ser Leu Ser Ser Lys Ser Ser Trp Ser Tyr Ile Val
                85                  90                  95

Glu Thr Pro Asn Ser Glu Asn Gly Thr Cys Tyr Pro Gly Asp Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Thr Ser Ser Trp Pro Asn His Asp Val
    130                 135                 140

Thr Lys Gly Val Thr Ala Ser Cys Ser His Ala Gly Ala Ser Ser Phe
145                 150                 155                 160

Tyr Lys Asn Leu Leu Trp Leu Thr Lys Lys Asn Gly Ser Tyr Pro Lys
                165                 170                 175

Leu Ser Lys Ser Tyr Ile Asn Asn Lys Glu Lys Glu Val Leu Val Leu
```

```
                180             185             190
Trp Gly Val His His Pro Ser Thr Ile Ala Asp Gln Gln Ser Leu Tyr
            195                 200                 205
Gln Asn Glu Asn Ala Tyr Val Ser Val Gly Ser Ser His Tyr Ser Arg
        210                 215                 220
Lys Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Ala
            260                 265                 270
Leu Ser Arg Gly Phe Gly Ser Gly Ile Ile Ile Ser Asn Ala Pro Met
        275                 280                 285
His Asp Cys Asp Thr Lys Cys Gln Thr Pro Gln Gly Ala Ile Asn Ser
        290                 295                 300
Ser Leu Pro Phe Gln Asn Ile His Pro Val Thr Ile Gly Glu Cys Pro
305                 310                 315                 320
Lys Tyr Val Arg Ser Thr Lys Leu Arg Met Ala Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Gln Lys Ser Thr
        370                 375                 380
Gln Asn Ala Ile Asp Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Lys Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
        450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asn Glu Cys Met Glu Ser Val Lys
                485                 490                 495
Asn Gly Thr Tyr Asp Tyr Pro Lys Tyr Ser Glu Glu Ser Lys Leu Asn
            500                 505                 510
Arg Glu Glu Ile Asp Gly Val Lys Leu Glu Ser Met Gly Val Tyr Gln
        515                 520                 525
Ile Leu Ala Ile Tyr Ser Thr Val Ala Ser Ser Leu Val Leu Leu Val
        530                 535                 540
Ser Leu Gly Ala Ile Ser Phe Trp Met Cys Ser Asn Gly Ser Leu Gln
545                 550                 555                 560
Cys Arg Ile Cys Ile
                565

<210> SEQ ID NO 11
<211> LENGTH: 1809
<212> TYPE: DNA
<213> ORGANISM: Artificial Sequence
```

-continued

<220> FEATURE:
<223> OTHER INFORMATION: IgE-U2-HATAntigen DNA Sequence

<400> SEQUENCE: 11

```
ggtaccggat ccgccaccat ggactggacc tggattctgt tcctggtcgc cgctgctacc     60
cgggtgcact ctaaggccaa gctgctggtg ctgctgtgca ccttcgccgc caccaacgcc    120
gacaccatct gcatcggcta ccacgccaac aacagcaccg acaccgtgga taccgtgctg    180
gaaaagaacg tgaccgtgac ccacagcgtg aacctgctgg aagataagca caacggcaag    240
ctgtgcaagc tgaagggaat cgccccccctg cagctgggca agtgcaatat cgccggctgg    300
attctgggca accccgagtg cgagagcctg agcagcaaga gcagctggtc ctacatcgtg    360
gaaaccccca acagcgagaa cggcacctgt taccccggcg acttcgccga ctacgaggaa    420
ctgcgcgagc agctgagcag cgtgtccagc ttcgagagat tcgagatctt ccccaagacc    480
agcagctggc ccaaccacga cgtgaccaag ggcgtgaccg ctagctgtag ccacgcaggc    540
gccagcagct tctacaagaa cctgctgtgg ctgaccaaga agaacggcag ctaccccaag    600
ctgagcaaga gctacatcaa caacaaagaa aaagaggtgc tggtcctctg gggcgtccac    660
caccccagca caatcgccga ccagcagagc ctgtaccaga acgagaacgc ctacgtgtcc    720
gtgggcagca gccactacag ccggaagttc acccccgaga tcgccaagcg gcccaaagtg    780
cgggaccagg aaggccggat caactactac tggaccctgc tggaacccgg cgacaccatc    840
atcttcgagg ccaacggcaa cctgatcgcc cccagatacg ccttcgccct gagcagaggc    900
ttcggcagcg gcatcatcat cagcaacgcc cccatgcacg actgcgacac caagtgccag    960
acccctcagg gcgccatcaa cagcagcctg cccttccaga acatccaccc cgtgaccatc   1020
ggcgagtgcc ccaaatacgt gcggagcacc aagctgcgga tggccaccgg cctgcggaac   1080
atccccagca tccagagcag aggcctgttc ggcgccattg ccggcttcat cgagggcggc   1140
tggaccggaa tggtggacgg gtggtacggc taccaccacc agaatgagca gggcagcggc   1200
tacgccgccg accagaagtc cacccagaac gccatcgacg gcatcaccaa caaagtgaac   1260
agcgtgatcg agaagatgaa cacccagttc accgccgtgg gcaaagagtt caacaagctg   1320
gaaaagcgga tggaaaacct gaacaagaag gtggacgacg gcttcctgga catctggacc   1380
tacaacgccg aactgctcgt gctgctggaa aacgagcgga ccctggactt ccacgacagc   1440
aacgtgaaga acctgtacga gaaagtgaag tcccagctga agaacaacgc caaagagatc   1500
ggcaacggct gcttcgagtt ctaccacaag tgcaacaacg agtgcatgga aagcgtgaag   1560
aacggaacct acgactaccc caagtacagc gaggaaagca agctgaaccg ggaagagatc   1620
gacggcgtga agctggaatc catgggcgtg taccagatcc tggccatcta cagcaccgtg   1680
gctagcagcc tggtgctgct ggtgtccctg ggcgccatct ccttttggat gtgctccaac   1740
ggcagcctgc agtgccggat ctgcatctac ccctacgacg tgcccgacta cgcctgatga   1800
ctcgagctc                                                           1809
```

<210> SEQ ID NO 12
<211> LENGTH: 592
<212> TYPE: PRT
<213> ORGANISM: Artificial Sequence
<220> FEATURE:
<223> OTHER INFORMATION: IgE-U2-HATantigen amino acid Sequence

<400> SEQUENCE: 12

```
Met Asp Trp Thr Trp Ile Leu Phe Leu Val Ala Ala Ala Thr Arg Val
1               5                   10                  15
```

His Ser Lys Ala Lys Leu Leu Val Leu Leu Cys Thr Phe Ala Ala Thr
            20                  25                  30

Asn Ala Asp Thr Ile Cys Ile Gly Tyr His Ala Asn Asn Ser Thr Asp
        35                  40                  45

Thr Val Asp Thr Val Leu Glu Lys Asn Val Thr Val Thr His Ser Val
    50                  55                  60

Asn Leu Leu Glu Asp Lys His Asn Gly Lys Leu Cys Lys Leu Lys Gly
65                  70                  75                  80

Ile Ala Pro Leu Gln Leu Gly Lys Cys Asn Ile Ala Gly Trp Ile Leu
                85                  90                  95

Gly Asn Pro Glu Cys Glu Ser Leu Ser Ser Lys Ser Ser Trp Ser Tyr
            100                 105                 110

Ile Val Glu Thr Pro Asn Ser Glu Asn Gly Thr Cys Tyr Pro Gly Asp
        115                 120                 125

Phe Ala Asp Tyr Glu Glu Leu Arg Glu Gln Leu Ser Ser Val Ser Ser
    130                 135                 140

Phe Glu Arg Phe Glu Ile Phe Pro Lys Thr Ser Ser Trp Pro Asn His
145                 150                 155                 160

Asp Val Thr Lys Gly Val Thr Ala Ser Cys Ser His Ala Gly Ala Ser
                165                 170                 175

Ser Phe Tyr Lys Asn Leu Leu Trp Leu Thr Lys Lys Asn Gly Ser Tyr
            180                 185                 190

Pro Lys Leu Ser Lys Ser Tyr Ile Asn Asn Lys Glu Lys Glu Val Leu
        195                 200                 205

Val Leu Trp Gly Val His His Pro Ser Thr Ile Ala Asp Gln Gln Ser
    210                 215                 220

Leu Tyr Gln Asn Glu Asn Ala Tyr Val Ser Val Gly Ser Ser His Tyr
225                 230                 235                 240

Ser Arg Lys Phe Thr Pro Glu Ile Ala Lys Arg Pro Lys Val Arg Asp
                245                 250                 255

Gln Glu Gly Arg Ile Asn Tyr Tyr Trp Thr Leu Leu Glu Pro Gly Asp
            260                 265                 270

Thr Ile Ile Phe Glu Ala Asn Gly Asn Leu Ile Ala Pro Arg Tyr Ala
        275                 280                 285

Phe Ala Leu Ser Arg Gly Phe Gly Ser Gly Ile Ile Ser Asn Ala
    290                 295                 300

Pro Met His Asp Cys Asp Thr Lys Cys Gln Thr Pro Gln Gly Ala Ile
305                 310                 315                 320

Asn Ser Ser Leu Pro Phe Gln Asn Ile His Pro Val Thr Ile Gly Glu
                325                 330                 335

Cys Pro Lys Tyr Val Arg Ser Thr Lys Leu Arg Met Ala Thr Gly Leu
            340                 345                 350

Arg Asn Ile Pro Ser Ile Gln Ser Arg Gly Leu Phe Gly Ala Ile Ala
        355                 360                 365

Gly Phe Ile Glu Gly Gly Trp Thr Gly Met Val Asp Gly Trp Tyr Gly
    370                 375                 380

Tyr His His Gln Asn Glu Gln Gly Ser Gly Tyr Ala Ala Asp Gln Lys
385                 390                 395                 400

Ser Thr Gln Asn Ala Ile Asp Gly Ile Thr Asn Lys Val Asn Ser Val
                405                 410                 415

Ile Glu Lys Met Asn Thr Gln Phe Thr Ala Val Gly Lys Glu Phe Asn
            420                 425                 430

```
Lys Leu Glu Lys Arg Met Glu Asn Leu Asn Lys Lys Val Asp Asp Gly
            435                 440                 445

Phe Leu Asp Ile Trp Thr Tyr Asn Ala Glu Leu Leu Val Leu Leu Glu
    450                 455                 460

Asn Glu Arg Thr Leu Asp Phe His Asp Ser Asn Val Lys Asn Leu Tyr
465                 470                 475                 480

Glu Lys Val Lys Ser Gln Leu Lys Asn Asn Ala Lys Glu Ile Gly Asn
                485                 490                 495

Gly Cys Phe Glu Phe Tyr His Lys Cys Asn Asn Glu Cys Met Glu Ser
            500                 505                 510

Val Lys Asn Gly Thr Tyr Asp Tyr Pro Lys Tyr Ser Glu Glu Ser Lys
        515                 520                 525

Leu Asn Arg Glu Glu Ile Asp Gly Val Lys Leu Glu Ser Met Gly Val
    530                 535                 540

Tyr Gln Ile Leu Ala Ile Tyr Ser Thr Val Ala Ser Ser Leu Val Leu
545                 550                 555                 560

Leu Val Ser Leu Gly Ala Ile Ser Phe Trp Met Cys Ser Asn Gly Ser
                565                 570                 575

Leu Gln Cys Arg Ile Cys Ile Tyr Pro Tyr Asp Val Pro Asp Tyr Ala
            580                 585                 590
```

<210> SEQ ID NO 13
<211> LENGTH: 1749
<212> TYPE: DNA
<213> ORGANISM: Artificial Sequence
<220> FEATURE:
<223> OTHER INFORMATION: BHA DNA Sequence

<400> SEQUENCE: 13

```
aaggccatca tcgtgctgct gatggtggtc acaagcaacg ccgaccggat ctgcaccggc      60
atcaccagca gcaacagccc ccacgtggtc aaaaccgcca cccagggcga agtgaacgtg     120
accggcgtga tccccctgac caccaccccc accaagagcc acttcgccaa cctgaagggc     180
accaagaccc ggggaaagct gtgccccaag tgcctgaact gcaccgacct ggacgtggcc     240
ctgggcagac ctatgtgcgt gggcaccacc cctagcgcca aggccagcat cctgcacgaa     300
gtgcggcccg tgaccagcgg ctgcttcccc atcatgcacg accggaccaa gatccggcag     360
ctccccaacc tgctgcgggg ctacgagaac atccggctga gcacccagaa cgtgatcaac     420
gccgagaagg cccctggcgg cccttacaga ctgggcacaa gcggctcttg ccccaacgcc     480
accagcaaga gcggctttttt cgccacaatg gcctggcccg tgcccaagga caacaacaag     540
accgccacca cccccctgac cgtggaagtg ccctacatct gcaccgaggg cgaggaccag     600
atcaccgtgt ggggcttcca cagcgataac aagacccaga tgaagaacct gtacggcgac     660
agcaaccccc agaagttcac cagctccgcc aacggcgtga ccacccacta cgtgtcccag     720
atcggcggct cccccgacca gacagaggat ggcggcctgc cccagagcgg cagaatcgtg     780
gtggactaca tggtgcagaa gcccggcaag accggcacca tcgtgtacca gcggggcatc     840
ctgctgcccc agaaagtgtg gtgcgccagc ggccggtcca agtgatcaa gggcagcctg     900
cctctgatcg gcgaggccga ttgcctgcac gagaagtacg gcggcctgaa caagagcaag     960
ccctactaca ccggcgagca cgccaaagcc atcggcaact gccccatctg gtcaaaaacc    1020
cccctgaagc tggccaacgg caccaagtac ggcctcccg ccaagctgct gaaagagcgg    1080
ggcttcttcg gcgctatcgc cggctttctg gaaggcggct gggagggcat gatcgccggc    1140
tggcacggct acacatctca cggcgctcat ggcgtggccg tggccgctga tctgaagtcc    1200
```

```
acccaggaag ccatcaacaa gatcaccaag aacctgaaca gcctgagcga gctggaagtg    1260
aagaatctgc agcggctgag cggcgccatg acgagctgc acaacgagat cctggaactg    1320
gacgagaagg tggacgacct gcgggccgac accatctcca gccagatcga gctggccgtg    1380
ctgctgtcca acgagggcat catcaacagc gaggacgagc atctgctggc cctgaacgg    1440 aagctgaaga agatgctggg ccctagcgcc gtggacatcg caacggctg cttcgagaca    1500 aagcacaagt gcaaccagac ctgcctggac cggatcgctg ccggcacctt caacgccggc    1560
gagttcagcc tgcccacctt cgacagcctg aacatcaccg ccgccagcct gaacgacgac    1620
ggcctggaca ccacaccat cctgctgtac tacagcaccg cagcctccag cctggccgtg    1680
accctgatga tcgccatctt catcgtgtac atggtgtctc gggacaacgt gtcctgcagc    1740
atctgcctg                                                           1749
```

<210> SEQ ID NO 14
<211> LENGTH: 583
<212> TYPE: PRT
<213> ORGANISM: Artificial Sequence
<220> FEATURE:
<223> OTHER INFORMATION: BHA Amino Acid Sequence

<400> SEQUENCE: 14

```
Lys Ala Ile Ile Val Leu Leu Met Val Val Thr Ser Asn Ala Asp Arg
1               5                   10                  15

Ile Cys Thr Gly Ile Thr Ser Ser Asn Ser Pro His Val Val Lys Thr
            20                  25                  30

Ala Thr Gln Gly Glu Val Asn Val Thr Gly Val Ile Pro Leu Thr Thr
        35                  40                  45

Thr Pro Thr Lys Ser His Phe Ala Asn Leu Lys Gly Thr Lys Thr Arg
    50                  55                  60

Gly Lys Leu Cys Pro Lys Cys Leu Asn Cys Thr Asp Leu Asp Val Ala
65                  70                  75                  80

Leu Gly Arg Pro Met Cys Val Gly Thr Thr Pro Ser Ala Lys Ala Ser
                85                  90                  95

Ile Leu His Glu Val Arg Pro Val Thr Ser Gly Cys Phe Pro Ile Met
            100                 105                 110

His Asp Arg Thr Lys Ile Arg Gln Leu Pro Asn Leu Leu Arg Gly Tyr
        115                 120                 125

Glu Asn Ile Arg Leu Ser Thr Gln Asn Val Ile Asn Ala Glu Lys Ala
    130                 135                 140

Pro Gly Gly Pro Tyr Arg Leu Gly Thr Ser Gly Ser Cys Pro Asn Ala
145                 150                 155                 160

Thr Ser Lys Ser Gly Phe Phe Ala Thr Met Ala Trp Ala Val Pro Lys
                165                 170                 175

Asp Asn Asn Lys Thr Ala Thr Asn Pro Leu Thr Val Glu Val Pro Tyr
            180                 185                 190

Ile Cys Thr Glu Gly Glu Asp Gln Ile Thr Val Trp Gly Phe His Ser
        195                 200                 205

Asp Asn Lys Thr Gln Met Lys Asn Leu Tyr Gly Asp Ser Asn Pro Gln
    210                 215                 220

Lys Phe Thr Ser Ser Ala Asn Gly Val Thr Thr His Tyr Val Ser Gln
225                 230                 235                 240

Ile Gly Gly Phe Pro Asp Gln Thr Glu Asp Gly Gly Leu Pro Gln Ser
                245                 250                 255
```

```
Gly Arg Ile Val Val Asp Tyr Met Val Gln Lys Pro Gly Lys Thr Gly
            260                 265                 270

Thr Ile Val Tyr Gln Arg Gly Ile Leu Leu Pro Gln Lys Val Trp Cys
        275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
        355                 360                 365

Phe Leu Glu Gly Gly Trp Glu Gly Met Ile Ala Gly Trp His Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580
```

<210> SEQ ID NO 15
<211> LENGTH: 1865
<212> TYPE: DNA
<213> ORGANISM: Artificial Sequence
<220> FEATURE:
<223> OTHER INFORMATION: IgE-BHA-HATantigen DNA Sequence

<400> SEQUENCE: 15

```
ggtaccggat ccgccaccat ggactggacc tggattctgt tcctggtggc cgctgccaca      60
cgggtgcaca gcaaggccat catcgtgctg ctgatggtgg tcacaagcaa cgccgaccgg     120
atctgcaccg gcatcaccag cagcaacagc ccccacgtgg tcaaaaccgc cacccagggc     180
```

-continued

```
gaagtgaacg tgaccggcgt gatccccctg accaccaccc ccaccaagag ccacttcgcc    240
aacctgaagg gcaccaagac ccggggaaag ctgtgcccca agtgcctgaa ctgcaccgac    300
ctggacgtgg ccctgggcag acctatgtgc gtgggcacca cccctagcgc caaggccagc    360
atcctgcacg aagtgcggcc cgtgaccagc ggctgcttcc ccatcatgca cgaccggacc    420
aagatccggc agctccccaa cctgctgcgg ggctacgaga acatccggct gagcacccag    480
aacgtgatca acgccgagaa ggcccctggc ggcccttaca gactgggcac aagcggctct    540
tgccccaacg ccaccagcaa gagcggcttt ttcgccacaa tggcctgggc cgtgcccaag    600
gacaacaaca agaccgccac caacccctg accgtggaag tgccctacat ctgcaccgag    660
ggcgaggacc agatcaccgt gtggggcttc cacagcgata acaagaccca gatgaagaac    720
ctgtacggcg acagcaaccc ccagaagttc accagctccg ccaacggcgt gaccacccac    780
tacgtgtccc agatcggcgg cttccccgac cagacagagg atggcggcct gccccagagc    840
ggcagaatcg tggtggacta catggtgcag aagcccggca agaccggcac catcgtgtac    900
cagcggggca tcctgctgcc ccagaaagtg tggtgcgcca gcggccggtc caaagtgatc    960
aagggcagcc tgcctctgat cggcgaggcc gattgcctgc acgagaagta cggcggcctg   1020
aacaagagca agccctacta caccggcgag cacgccaaag ccatcggcaa ctgccccatc   1080
tgggtcaaaa cccccctgaa gctggccaac ggcaccaagt accggcctcc cgccaagctg   1140
ctgaaagagc ggggcttctt cggcgctatc gccggctttc tggaaggcgg ctgggagggc   1200
atgatcgccg gctggcacgg ctacacatct cacggcgctc atggcgtggc cgtggccgct   1260
gatctgaagt ccacccagga agccatcaac aagatcacca agaacctgaa cagcctgagc   1320
gagctggaag tgaagaatct gcagcggctg agcggcgcca tggacgagct gcacaacgag   1380
atcctggaac tggacgagaa ggtggacgac ctgcgggccg acaccatctc cagccagatc   1440
gagctggccg tgctgctgtc caacgagggc atcatcaaca gcgaggacga gcatctgctg   1500
gccctggaac ggaagctgaa gaagatgctg ggccctagcg ccgtggacat cggcaacggc   1560
tgcttcgaga caaagcacaa gtgcaaccag acctgcctgg accggatcgc tgccggcacc   1620
ttcaacgccg gcgagttcag cctgcccacc ttcgacagcc tgaacatcac cgccgccagc   1680
ctgaacgacg acggcctgga caaccacacc atcctgctgt actacagcac cgcagcctcc   1740
agcctggccg tgaccctgat gatcgccatc ttcatcgtgt acatggtgtc tcgggacaac   1800
gtgtcctgca gcatctgcct gtacccctac gacgtgcccg actacgctga tgactcgagc   1860
tcctc                                                                1865
```

```

<210> SEQ ID NO 16
<211> LENGTH: 610
<212> TYPE: PRT
<213> ORGANISM: Artificial Sequence
<220> FEATURE:
<223> OTHER INFORMATION: IgE-BHA-HATantigen Amino Acid Sequence

<400> SEQUENCE: 16

Met Asp Trp Thr Trp Ile Leu Phe Leu Val Ala Ala Ala Thr Arg Val
1               5                   10                  15

His Ser Lys Ala Ile Ile Val Leu Leu Met Val Val Thr Ser Asn Ala
            20                  25                  30

Asp Arg Ile Cys Thr Gly Ile Thr Ser Ser Asn Ser Pro His Val Val
        35                  40                  45

Lys Thr Ala Thr Gln Gly Glu Val Asn Val Thr Gly Val Ile Pro Leu
    50                  55                  60
```

```
Thr Thr Thr Pro Thr Lys Ser His Phe Ala Asn Leu Lys Gly Thr Lys
 65                  70                  75                  80

Thr Arg Gly Lys Leu Cys Pro Lys Cys Leu Asn Cys Thr Asp Leu Asp
                 85                  90                  95

Val Ala Leu Gly Arg Pro Met Cys Val Gly Thr Thr Pro Ser Ala Lys
                100                 105                 110

Ala Ser Ile Leu His Glu Val Arg Pro Val Thr Ser Gly Cys Phe Pro
            115                 120                 125

Ile Met His Asp Arg Thr Lys Ile Arg Gln Leu Pro Asn Leu Leu Arg
        130                 135                 140

Gly Tyr Glu Asn Ile Arg Leu Ser Thr Gln Asn Val Ile Asn Ala Glu
145                 150                 155                 160

Lys Ala Pro Gly Gly Pro Tyr Arg Leu Gly Thr Ser Gly Ser Cys Pro
                165                 170                 175

Asn Ala Thr Ser Lys Ser Gly Phe Phe Ala Thr Met Ala Trp Ala Val
            180                 185                 190

Pro Lys Asp Asn Asn Lys Thr Ala Thr Asn Pro Leu Thr Val Glu Val
        195                 200                 205

Pro Tyr Ile Cys Thr Glu Gly Glu Asp Gln Ile Thr Val Trp Gly Phe
        210                 215                 220

His Ser Asp Asn Lys Thr Gln Met Lys Asn Leu Tyr Gly Asp Ser Asn
225                 230                 235                 240

Pro Gln Lys Phe Thr Ser Ser Ala Asn Gly Val Thr Thr His Tyr Val
                245                 250                 255

Ser Gln Ile Gly Gly Phe Pro Asp Gln Thr Glu Asp Gly Gly Leu Pro
            260                 265                 270

Gln Ser Gly Arg Ile Val Val Asp Tyr Met Val Gln Lys Pro Gly Lys
            275                 280                 285

Thr Gly Thr Ile Val Tyr Gln Arg Gly Ile Leu Leu Pro Gln Lys Val
        290                 295                 300

Trp Cys Ala Ser Gly Arg Ser Lys Val Ile Lys Gly Ser Leu Pro Leu
305                 310                 315                 320

Ile Gly Glu Ala Asp Cys Leu His Glu Lys Tyr Gly Gly Leu Asn Lys
                325                 330                 335

Ser Lys Pro Tyr Tyr Thr Gly Glu His Ala Lys Ala Ile Gly Asn Cys
            340                 345                 350

Pro Ile Trp Val Lys Thr Pro Leu Lys Leu Ala Asn Gly Thr Lys Tyr
        355                 360                 365

Arg Pro Pro Ala Lys Leu Leu Lys Glu Arg Gly Phe Phe Gly Ala Ile
        370                 375                 380

Ala Gly Phe Leu Glu Gly Gly Trp Glu Gly Met Ile Ala Gly Trp His
385                 390                 395                 400

Gly Tyr Thr Ser His Gly Ala His Gly Val Ala Val Ala Ala Asp Leu
                405                 410                 415

Lys Ser Thr Gln Glu Ala Ile Asn Lys Ile Thr Lys Asn Leu Asn Ser
            420                 425                 430

Leu Ser Glu Leu Glu Val Lys Asn Leu Gln Arg Leu Ser Gly Ala Met
        435                 440                 445

Asp Glu Leu His Asn Glu Ile Leu Glu Leu Asp Glu Lys Val Asp Asp
        450                 455                 460

Leu Arg Ala Asp Thr Ile Ser Ser Gln Ile Glu Leu Ala Val Leu Leu
465                 470                 475                 480
```

```
Ser Asn Glu Gly Ile Ile Asn Ser Glu Asp Glu His Leu Leu Ala Leu
            485                 490                 495

Glu Arg Lys Leu Lys Lys Met Leu Gly Pro Ser Ala Val Asp Ile Gly
        500                 505                 510

Asn Gly Cys Phe Glu Thr Lys His Lys Cys Asn Gln Thr Cys Leu Asp
        515                 520                 525

Arg Ile Ala Ala Gly Thr Phe Asn Ala Gly Glu Phe Ser Leu Pro Thr
    530                 535                 540

Phe Asp Ser Leu Asn Ile Thr Ala Ala Ser Leu Asn Asp Asp Gly Leu
545                 550                 555                 560

Asp Asn His Thr Ile Leu Leu Tyr Tyr Ser Thr Ala Ala Ser Ser Leu
                565                 570                 575

Ala Val Thr Leu Met Ile Ala Ile Phe Ile Val Tyr Met Val Ser Arg
            580                 585                 590

Asp Asn Val Ser Cys Ser Ile Cys Leu Tyr Pro Tyr Asp Val Pro Asp
                595                 600                 605

Tyr Ala
    610

<210> SEQ ID NO 17
<211> LENGTH: 18
<212> TYPE: PRT
<213> ORGANISM: Artificial Sequence
<220> FEATURE:
<223> OTHER INFORMATION: IgE Leader Amino Acid Sequence

<400> SEQUENCE: 17

Met Asp Trp Thr Trp Ile Leu Phe Leu Val Ala Ala Thr Arg Val
1               5                   10                  15

His Ser

<210> SEQ ID NO 18
<211> LENGTH: 9
<212> TYPE: PRT
<213> ORGANISM: Artificial Sequence
<220> FEATURE:
<223> OTHER INFORMATION: HA tag amino acid sequence

<400> SEQUENCE: 18

Tyr Pro Tyr Asp Val Pro Asp Tyr Ala
1               5

<210> SEQ ID NO 19
<211> LENGTH: 1698
<212> TYPE: DNA
<213> ORGANISM: Artificial Sequence
<220> FEATURE:
<223> OTHER INFORMATION: pGX2012 H1HA-ConBris DNA Sequence

<400> SEQUENCE: 19
atgaaggtga aactgctggt gctgctgtgc accttcaccg ccacctacgc cgacaccatc      60
tgcatcggct accacgccaa caacagcacc gacaccgtgg ataccgtgct ggaaaagaac     120
gtgaccgtga cccacagcgt gaacctgctg gaaaacagcc acaacggcaa gctgtgcctg     180
ctgaagggaa tcgcccccct gcagctgggc aattgcagcg tggccggctg gattctgggc     240
aaccccgagt gcgagctgct gatcagcaaa gagtcctggt cctacatcgt ggaaaagccc     300
aaccccgaga cggcacctg ttaccccggc cacttcgccg actacgagga actgcgcgag     360
cagctgagca gcgtgtccag cttcgagaga ttcgagatct cccccaaaga gtctagctgg     420
```

-continued

```
cccaaccaca ccgtgacagg cgtgtccgcc agctgctccc acaacggcga gagcagcttc    480
taccggaacc tgctgtggct gaccggcaag aacggcctgt accccaacct gagcaagagc    540
tatgccaaca acaaagaaaa agaggtgctg gtgctgtggg gcgtgcacca cccccccaac    600
atcggcgacc agaaggccct gtaccacacc gagaacgcct acgtgtccgt ggtgtccagc    660
cactacagcc ggaagttcac ccccgagatc gccaagcggc ccaaagtgcg ggaccaggaa    720
ggccggatca actactactg gaccctgctg gaacccggcg acaccatcat cttcgaggcc    780
aacggcaacc tgatcgcccc cagatacgcc ttcgccctga gcagaggctt cggcagcggc    840
atcatcaaca gcaacgcccc catggacaag tgcgacgcca agtgccagac cccccagggc    900
gccatcaaca gctccctgcc cttccagaac gtgcaccccg tgaccatcgg cgagtgcccc    960
aaatacgtgc ggagcgccaa gctgcggatg gtgacaggcc tgcggaacat ccccagcatc   1020
cagagcagag gcctgttcgg cgccattgcc ggcttcatcg agggcggctg gaccggaatg   1080
gtggacgggt ggtacggcta ccaccaccag aacgagcagg gcagcggcta cgccgccgac   1140
cagaagtcca cccagaacgc catcaacggc atcaccaaca aagtgaacag cgtgatcgag   1200
aagatgaaca cccagttcac cgccgtgggc aaagagttca acaagctgga acggcggatg   1260
gaaaacctga acaagaaggt ggacgacggc tttatcgaca tctggaccta caacgccgag   1320
ctgctggtcc tgctggaaaa cgagcggacc ctggacttcc acgacagcaa cgtgaagaac   1380
ctgtacgaga aagtgaagtc ccagctgaag aacaacgcca aagagatcgg caacggctgc   1440
ttcgagttct accacaagtg caacgacgag tgcatggaaa gcgtgaagaa tggcacctac   1500
gactacccca agtacagcga ggaaagcaag ctgaaccgcg agaagatcga cggcgtgaag   1560
ctggaatcca tgggcgtgta ccagatcctg gccatctaca gcaccgtggc cagcagcctg   1620
gtcctgctgg tgtccctggg cgccatctcc ttttggatgt gctccaacgg cagcctgcag   1680
tgccggatct gcatctga                                                 1698
```

```

<210> SEQ ID NO 20
<211> LENGTH: 565
<212> TYPE: PRT
<213> ORGANISM: Artificial Sequence
<220> FEATURE:
<223> OTHER INFORMATION: pGX2012 H1HA-ConBris Protein Sequence

<400> SEQUENCE: 20

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
```

```
                130                 135                 140
Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
                180                 185                 190

Trp Gly Val His His Pro Pro Asn Ile Gly Asp Gln Lys Ala Leu Tyr
                195                 200                 205

His Thr Glu Asn Ala Tyr Val Ser Val Val Ser Ser His Tyr Ser Arg
                210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
                260                 265                 270

Leu Ser Arg Gly Phe Gly Ser Gly Ile Ile Asn Ser Asn Ala Pro Met
                275                 280                 285

Asp Lys Cys Asp Ala Lys Cys Gln Thr Pro Gln Gly Ala Ile Asn Ser
                290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
                355                 360                 365

His Gln Asn Glu Gln Gly Ser Gly Tyr Ala Ala Asp Gln Lys Ser Thr
                370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
                420                 425                 430

Asp Ile Trp Thr Tyr Asn Ala Glu Leu Leu Val Leu Leu Glu Asn Glu
                435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
                515                 520                 525

Ile Leu Ala Ile Tyr Ser Thr Val Ala Ser Ser Leu Val Leu Leu Val
                530                 535                 540

Ser Leu Gly Ala Ile Ser Phe Trp Met Cys Ser Asn Gly Ser Leu Gln
545                 550                 555                 560
```

Cys Arg Ile Cys Ile
              565

<210> SEQ ID NO 21
<211> LENGTH: 1701
<212> TYPE: DNA
<213> ORGANISM: Artificial Sequence
<220> FEATURE:
<223> OTHER INFORMATION: pGX2015 H1HA-ConTT DNA Sequence

<400> SEQUENCE: 21

| | | | | | |
|---|---|---|---|---|---|
| aaggcaaaac | tgctggtgct | gctgtgcgca | ttcaccgcca | catacgctga | cacaatctgc | 60 |
| attggctatc | acgccaacaa | ttccactgac | accgtggata | ctgtcctgga | agaagaacgtg | 120 |
| acagtcactc | acagcgtgaa | cctgctggaa | gattcccata | atggaaagct | gtgccggctg | 180 |
| aaaggcatcg | ctcctctgca | gctggggaac | tgctctgtgg | cagggtggat | tctgggaaat | 240 |
| ccagagtgtg | aaagcctgtt | ttccaaggag | tcatggagct | acatcgccga | gacccccaac | 300 |
| cctgaaaatg | gcacatgcta | ccctgggtat | ttcgctgact | atgaggaact | gcgggagcag | 360 |
| ctgagctccg | tgtctagttt | cgagagattt | gaaatcttcc | caaggaatc | aagctggccc | 420 |
| aaccacaccg | tgacaaaggg | agtcactgcc | tcctgttctc | ataacggcaa | atcctctttt | 480 |
| taccgaaatc | tgctgtggct | gacagagaaa | acggcctgt | acccaaatct | gagtaagtca | 540 |
| tacgtgaaca | ataaggagaa | agaagtgctg | gtcctgtggg | gggtccacca | tcctccaac | 600 |
| atcggagacc | agcgcgccat | ctaccacacc | gagaatgctt | acgtgagcgt | ggtcagttca | 660 |
| cattacagcc | ggcggttcac | ccctgagatc | gccaagcgac | aaaagtgcg | ggaccaggaa | 720 |
| ggcaggatta | actactattg | gactctgctg | gagccagggg | ataccatcat | tttcgaagca | 780 |
| aacggaaatc | tgatcgcccc | ctggtatgca | tttgccctga | gtcgcggatt | cggctcaggg | 840 |
| atcattacct | ctaatgcaag | tatgggcgag | tgcgatgcca | agtgtcagac | accacagggg | 900 |
| gctatcaaca | gctccctgcc | cttccagaat | gtgcaccctg | tcaccattgg | agagtgcccc | 960 |
| aaatacgtga | agcacaaa | gctgaggatg | gtcactggcc | tgcgcaacat | cccttcaatt | 1020 |
| cagagccgag | gcctgtttgg | ggctatcgca | ggcttcattg | agggcgggtg | gacccgggatg | 1080 |
| atcgacggat | ggtacggcta | tcaccatcag | aatgaacagg | gatcaggcta | cgccgctgat | 1140 |
| cagaagagca | cacagaacgc | aatcaatggg | attactaaca | aagtgaatag | cgtcatcgag | 1200 |
| aagatgaaca | ctcagtttac | cgccgtggga | aaggagttca | acaagctgga | gaggcgcatg | 1260 |
| gaaaacctga | ataagaaagt | ggacgatggc | tttctggata | tttggactta | caacgctgag | 1320 |
| ctgctggtgc | tgctggagaa | tgaaagaacc | ctggacttcc | acgattccaa | cgtgaagaat | 1380 |
| ctgtatgaaa | aggtcaaatc | tcagctgaag | aacaatgcaa | aagagatcgg | aacggatgt | 1440 |
| ttcgagttct | accataaatg | caacaatgag | tgtatggaat | ctgtgaaaaa | cgggacctac | 1500 |
| gactatccca | gtattccga | ggaatctaag | ctgaataggg | agaaaatcga | tggagtgaag | 1560 |
| ctggaaagta | tgggcgtcta | ccagatcctg | gctatctaca | gcacagtggc | atctagtctg | 1620 |
| gtgctgctgg | tcagcctggg | cgctatctcc | ttctggatgt | gctcaaatgg | gtctctgcag | 1680 |
| tgccgcatct | gtatctaatg | a | | | | 1701 |

<210> SEQ ID NO 22
<211> LENGTH: 565
<212> TYPE: PRT
<213> ORGANISM: Artificial Sequence
<220> FEATURE:
<223> OTHER INFORMATION: pGX2015 H1HA-ConTT Protein Sequence

<400> SEQUENCE: 22

```
Lys Ala Lys Leu Leu Val Leu Leu Cys Ala Phe Thr Ala Thr Tyr Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45

Leu Glu Asp Ser His Asn Gly Lys Leu Cys Arg Leu Lys Gly Ile Ala
    50                  55                  60

Pro Leu Gln Leu Gly Asn Cys Ser Val Ala Gly Trp Ile Leu Gly Asn
65                  70                  75                  80

Pro Glu Cys Glu Ser Leu Phe Ser Lys Glu Ser Trp Ser Tyr Ile Ala
                85                  90                  95

Glu Thr Pro Asn Pro Glu Asn Gly Thr Cys Tyr Pro Gly Tyr Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Glu Ser Ser Trp Pro Asn His Thr Val
    130                 135                 140

Thr Lys Gly Val Thr Ala Ser Cys Ser His Asn Gly Lys Ser Ser Phe
145                 150                 155                 160

Tyr Arg Asn Leu Leu Trp Leu Thr Glu Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Ser Asn Ile Gly Asp Gln Arg Ala Ile Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Ser Met
        275                 280                 285

Gly Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
```

```
                    405                 410                 415
Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 23
<211> LENGTH: 1701
<212> TYPE: DNA
<213> ORGANISM: Artificial Sequence
<220> FEATURE:
<223> OTHER INFORMATION: pGX2016 H3HA-V2 DNA Sequence

<400> SEQUENCE: 23
atgaagacca tcattgccct gagctacatc ctgtgcctgg tgttcgccca gaagctgccc       60
ggcaacgaca cagcaccgc caccctgtgt ctgggccacc acgccgtgcc aacggcacc       120 ctggtgaaaa ccatcaccaa cgaccagatc gaagtgacca acgccaccga gctggtgcag       180
agcagcagca ccggcagaat ctgcgacagc ccccacagaa tcctggacgg cgagaactgc       240
accctgatcg acgccctgct gggcgatccc cactgcgacg gcttccagaa caaagaatgg       300
gacctgttcg tggaacggtc caaggcctac agcaactgct accccacga cgtgcccgac       360 tacgccagcc tgagaagcct ggtggccagc agcggcacac tggaattcaa caacgagagc       420
ttcaactgga ccggcgtggc ccagaacggc accagcagcg cctgcaagcg gcggagcgtg       480
aagtccttct ctcccggct gaactggctg caccagctga agtacaagta ccccgccctg       540
aacgtgacca tgcccaacaa tgagaagttc gacaagctgt acatctgggg cgtgcaccac       600
cctagcaccg acagcgacca gaccagcctg tacgcccagg ccagcggcag agtgaccgtg       660
tccaccaagc ggagccagca gaccgtgatc cccaacatcg gcagcagacc ttgggtccgc       720
ggcgtgtcca gccggatcag catctactgg accatcgtga gcccggcga catcctgctg       780 atcaactcca ccggcaacct gatcgccccc agaggctact tcaagatcag aagcggcaag       840
agcagcatca tgagaagcga cgcccccatc ggcaagtgca cagcgagtg catcaccccc       900 aacggcagca tccccaacga caagcccttc cagaacgtga accggatcac ctacggcgcc       960
tgccccagat acgtgaagca gaacaccctg aagctggcca ccggcatgcg aacgtgccc      1020 gagaagcaga cccggggcat ctttggcgcc attgccggct tcatcgagaa cggctgggag      1080
ggcatggtgg acgggtggta cggcttccgg caccagaata gcgagggcac aggccaggcc      1140
```

```
gccgacctga aaagcaccca ggccgccatc aaccagatca acggcaagct gaaccggctg    1200
atcgaaaaga ccaacgagaa gttccaccag atcgagaaag aattcagcga ggtggaaggc    1260
agaatccagg acctggaaaa gtacgtggaa gataccaaga tcgacctgtg gtcctacaac    1320
gccgagctgc tggtggccct ggaaaaccag cacaccatcg acctgaccga ctccgagatg    1380
aacaagctgt tcgagcggac ccggaagcag ctgcgcgaga cgccgagga catgggcaac    1440 ggctgcttta agatctacca caagtgcgac aacgcctgca tcggctccat ccggaacggc    1500
acctacgacc acgacgtgta ccgggacgag gccctgaaca accggttcca gatcaagggc    1560
gtggaactga agtccggcta caaggactgg attctgtgga tcagcttcgc catcagctgc    1620
tttctgctgt gcgtggtgct gctgggcttc atcatgtggg cctgccagaa gggcaacatc    1680
cgctgcaaca tctgcatctg a                                              1701
```

<210> SEQ ID NO 24
<211> LENGTH: 566
<212> TYPE: PRT
<213> ORGANISM: Artificial Sequence
<220> FEATURE:
<223> OTHER INFORMATION: pGX2016 H3HA-V2 Protein Sequence

<400> SEQUENCE: 24

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Ser Ala Cys Lys Arg Arg Ser Val
145                 150                 155                 160

Lys Ser Phe Phe Ser Arg Leu Asn Trp Leu His Gln Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Ser Thr Asp Ser Asp Gln Thr
        195                 200                 205

Ser Leu Tyr Ala Gln Ala Ser Gly Arg Val Thr Val Ser Thr Lys Arg
    210                 215                 220

Ser Gln Gln Thr Val Ile Pro Asn Ile Gly Ser Arg Pro Trp Val Arg
225                 230                 235                 240

Gly Val Ser Ser Arg Ile Ser Ile Tyr Trp Thr Ile Val Lys Pro Gly
                245                 250                 255
```

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
        290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 25
<211> LENGTH: 1758
<212> TYPE: DNA
<213> ORGANISM: Artificial Sequence
<220> FEATURE:
<223> OTHER INFORMATION: pGX2014 B-HA-V2 DNA Sequence

<400> SEQUENCE: 25
atgaaggcca tcatcgtgct gctgatggtg gtgacaagca acgccgaccg gatctgcacc      60
ggcatcacca gcagcaacag ccccccacgtg gtgaaaaccg ccacccaggg cgaagtgaac     120
gtgaccggcg tgatccccct gaccaccacc cccaccaaga gccacttcgc caacctgaag     180
ggcaccgaga cacggggcaa gctgtgtccc aagtgcctga actgcaccga cctggacgtg     240
gccctgggca gacccaagtg caccggcaac atccccagcg ccagagtgtc catcctgcac     300

```
gaagtgcggc ccgtgacctc cggctgcttc cctatcatgc acgaccggac caagatcaga    360
cagctgccta acctgctgcg gggctacgag cacatccggc tgagcaccca caacgtgatc    420
aacgccgaga acgcccctgg cggcccttac aagatcggca ccagcggaag ctgccccaac    480
gtgacaaacg gcaacggctt cttcgccacc atggcctggg ccgtgcccaa gaacgacaac    540
aacaagacag ccaccaacag cctgaccatc gaggtgccct acatctgcac cgagggcgag    600
gaccagatca ccgtgtgggg cttccacagc gacaacgaga cacagatggc caagctgtac    660
ggcgacagca agccccagaa gttcaccagc tccgccaacg gcgtgaccac ccactacgtg    720
tcccagatcg gcggcttccc caaccagacc gaggatggcg gcctgcccca gagcggcaga    780
atcgtggtgg actacatggt gcagaagtcc ggcaagaccg gcaccatcac ctaccagcgg    840
ggcatcctgc tgccccagaa agtgtggtgc gccagcggcc ggtccaaagt gatcaaggga    900
agcctgcccc tgatcggcga ggccgattgc ctgcacgaga agtacggcgg cctgaacaag    960
agcaagccct actacaccgg cgagcacgcc aaggccatcg gcaactgccc catctgggtg   1020
aaaacccccc tgaagctggc caacggcacc aagtaccggc ctcccgccaa gctgctgaaa   1080
gagcggggct tcttcggcgc tatcgccggc tttctggaag gcggctggga gggcatgatc   1140
gccggctggc acggctacac atctcacggc gctcatggcg tggccgtggc cgccgatctg   1200
aagtccaccc aggaagccat caacaagatc accaagaacc tgaacagcct gagcgagctg   1260
gaagtgaaga acctgcagcg gctgagcggc gccatggacg agctgcacaa cgagatcctg   1320
gaactggacg agaaggtgga cgacctgcgg gccgacacca tctccagcca gatcgagctg   1380
gccgtgctgc tgtccaacga gggcatcatc aacagcgagg acgagcatct gctggccctg   1440
gaacggaagc tgaagaagat gctgggcccc tccgccgtgg aaatcggcaa tggctgcttc   1500
gagacaaagc acaagtgcaa ccagacctgc ctggaccgga tcgctgccgg caccttcgat   1560
gccggcgagt tcagcctgcc caccttcgac agcctgaaca tcaccgccgc cagcctgaac   1620
gacgacggcc tggacaacca caccatcctg ctgtactaca gcaccgccgc ctccagcctg   1680
gccgtgaccc tgatgatcgc catcttcgtg gtgtacatgg tgtccagaga caacgtgtcc   1740
tgcagcatct gcctgtga                                                 1758
```

```

<210> SEQ ID NO 26
<211> LENGTH: 585
<212> TYPE: PRT
<213> ORGANISM: Artificial Sequence
<220> FEATURE:
<223> OTHER INFORMATION: pGX2014 B-HA-V2 protein Sequence

<400> SEQUENCE: 26

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Arg Val
                85                  90                  95
```

-continued

```
Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120             125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
```

```
                515                 520                 525
Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585
```

<210> SEQ ID NO 27
<211> LENGTH: 1704
<212> TYPE: DNA
<213> ORGANISM: Artificial Sequence
<220> FEATURE:
<223> OTHER INFORMATION: H3HA-V3 DNA Sequence

<400> SEQUENCE: 27

```
atgaaaacaa tcatcgccct gtcctacatc ctgtgcctgg tctttgccca gaaactgccc    60
gggaacgaca actcaactgc tacactgtgt ctgggccacc atgccgtgcc taacgggacc   120
ctggtcaaga ccattacaaa cgaccagatc gaagtgacta atgctaccga actggtccag   180
agctcctcta ccggacgcat ttgcgacagc ccacaccgaa tcctggatgg caaaaattgt   240
acactgatcg acgcactgct gggagacccc cattgcgatg gcttccagaa caggagtggg   300
gatctgtttg tggaacgcag taaagcttac tcaaattgtt accccctatg cgtgcctgat   360
tatgcatccc tgcgatctct ggtcgccagt tcagggactc tggagttcat caacgaagac   420
tttaattgga ccggagtggc tcaggatggc gggtcctacg catgcaagag aggcagtgtc   480
aactcattct ttagcaggct gaattggctg cacaagctgg agtacaaata tcccgccctg   540
aacgtgacta tgcctaacaa tgggaagttc gacaaactgt acatctgggg agtgcaccat   600
ccctccactg actctgatca gacctcactg tatgtccggg ccagcggcag agtgacagtc   660
agcactaagc ggtcccagca cagtgatc cctaatattg aagtaggcc atgggtccgc       720
ggcctgagct ccagaatctc aatctactgg acaatcgtga acctggcga tatcctgctg     780
attaacagca ctgggaatct gattgctcca agaggatatt tcaagattag gaccggcaaa    840
tctagtatca tgcggagcga cgcaccaatt ggcaactgct caagcgagtg tattactccc    900
aacgggtcca tcccaaatga taagcccttt cagaacgtga ataggatcac ctacggggcc    960
tgtccccgct atgtcaagca gaacacactg aaactggcta ctggaatgcg aaatgtgcct   1020
gagaaacaga cccggggcat cttcggggct attgcaggct ttatcgagaa cggatgggaa   1080
ggcatggtgg acgggtggta cggattcaga caccagaatt ccgagggaac cggacaggca   1140
gctgacctga gtctacaca ggcagccatc gatcagatta acgcaaact gaataggctg     1200
atcgagaaga caaacgaaaa attccatcag attgagaagg agttcagcga ggtgaaggg    1260
cgcatccagg atctggagaa gtacgtcgaa gacactaaaa ttgatctgtg gtcttataac   1320
gccgagctgc tggtggctct ggaaaatcag cacaccatcg acctgacaga tagtgagatg   1380
aataagctgt tcgaaaagac ccgaaaacag ctgcgggaga acgcagaaga catggggaat   1440
ggatgcttta agatctacca caaatgcgat aacgcctgta tcggctctat taggaatggg   1500
acatacgacc atgacgtgta ccgggacgag gccctgaaca atagatttca gatcaagggg   1560
gtggaactga gagcggata caaggattgg attctgtgga tctctttcgc cattagttgc    1620
tttctgctgt gcgtggtcct gctgggattc attatgtggg cttgtcagaa aggaaatatt   1680
```
cggtgtaaca tctgcatttg ataa    1704

<210> SEQ ID NO 28
<211> LENGTH: 566
<212> TYPE: PRT
<213> ORGANISM: Artificial Sequence
<220> FEATURE:
<223> OTHER INFORMATION: H3HA-V3 protein Sequence

<400> SEQUENCE: 28

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Asp Phe Asn Trp Thr
    130                 135                 140

Gly Val Ala Gln Asp Gly Gly Ser Tyr Ala Cys Lys Arg Gly Ser Val
145                 150                 155                 160

Asn Ser Phe Phe Ser Arg Leu Asn Trp Leu His Lys Leu Glu Tyr Lys
                165                 170                 175

Tyr Pro Ala Leu Asn Val Thr Met Pro Asn Asn Gly Lys Phe Asp Lys
            180                 185                 190

Leu Tyr Ile Trp Gly Val His His Pro Ser Thr Asp Ser Asp Gln Thr
        195                 200                 205

Ser Leu Tyr Val Arg Ala Ser Gly Arg Val Thr Val Ser Thr Lys Arg
    210                 215                 220

Ser Gln Gln Thr Val Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Thr Gly Lys Ser Ser Ile Met Arg Ser Asp Ala
        275                 280                 285

Pro Ile Gly Asn Cys Ser Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350
```

```
Gly Phe Ile Glu Asn Gly Trp Glu Gly Met Val Asp Gly Trp Tyr Gly
            355                 360                 365
Phe Arg His Gln Asn Ser Glu Gly Thr Gly Gln Ala Ala Asp Leu Lys
        370                 375                 380
Ser Thr Gln Ala Ala Ile Asp Gln Ile Asn Gly Lys Leu Asn Arg Leu
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
    450                 455                 460
Glu Lys Thr Arg Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
    530                 535                 540
Val Val Leu Leu Gly Phe Ile Met Trp Ala Cys Gln Lys Gly Asn Ile
545                 550                 555                 560
Arg Cys Asn Ile Cys Ile
                565
```

<210> SEQ ID NO 29
<211> LENGTH: 1704
<212> TYPE: DNA
<213> ORGANISM: Artificial Sequence
<220> FEATURE:
<223> OTHER INFORMATION: H3HA-V4 DNA Sequence

<400> SEQUENCE: 29

```
atgaaaacaa tcatcgccct gtcctacatc ctgtgcctgg tctttgctca gaaactgcct        60
ggaaatgaca actctactgc tacactgtgt ctgggacacc atgcagtgcc aaacggcacc       120
atcgtcaaaa ccattacaaa cgaccagatc gaagtgacta atgctaccga actggtccag       180
agctcctcta caggagagat tgcgacagc ccccaccaga tcctggatgg cgaaaattgt       240
actctgattg acgcactgct gggggaccct cagtgcgatg gattccagaa caagaaatgg       300
gatctgtttg tggagcggtc caaggcctac tctaattgtt accctatga cgtgcctgat       360
tatgcttcac tgagaagcct ggtcgcaagt tcaggcaccc tggagttcaa caatgaatcc       420
tttaactgga cagggtgac tcagaatgga acaagctccg cctgcatccg agatccaac       480
aattcttct ttagtcgcct gaactggctg acccatctga agttcaaata ccctgccctg       540
aatgtgacaa tgccaaacaa tgagcagttt gacaagctgt atatctgggg cgtccaccat       600
ccaggaaccg acaacgatca gatcttcctg tacgctcaag caagtggcag gattaccgtg       660
agtacaaaac gctcacagca gacagtcatc cctaacattg gtcaaggcc acgcgtgcga       720
aatatcccct caagaatcag catctactgg actattgtca agccaggcga tatcctgctg       780
attaacagca ccgggaatct gatcgccccc agaggatact tcaagattag atctggcaaa       840
```

-continued

```
tctagtatca tgaggagtga cgctcccatt ggcaagtgca actcagagtg tattactcct      900
aacgggagca tcccaaatga taaacccttt cagaacgtga atagaatcac ctacggggca      960
tgtcctagat atgtcaagca gaacacactg aaactggcca ctggaatgcg caatgtgcca     1020
gagaagcaga cccgagggat cttcggagcc attgctggct ttatcgagaa cggctgggaa     1080
gggatggtgg acggatggta cggcttccgg caccagaatt ccgagggaat cggacaggca     1140
gctgacctga agtctacaca ggcagccatc gatcagatta cgggaaaact gaataggctg     1200
atcggaaaga ctaacgaaaa gttccatcag atcgagaagg aatttccga ggtggaaggc      1260 cgcatccagg atctggagaa gtacgtcgaa gacaccaaaa ttgatctgtg gtcttataac     1320
gcagagctgc tggtggccct ggaaaatcag cacactatcg acctgaccga tagtgagatg     1380
aataagctgt cgaaaagac taagaaacag ctgcgagaga cgctgaaga catgggaaat       1440 ggctgcttta agatctacca caaatgcgat aacgcatgta tcggatctat tcggaatggc     1500
acatacgacc atgacgtgta ccgagacgag gccctgaaca atcggtttca gatcaagggc     1560
gtcgaactga agtccgggta caaagattgg attctgtgga ttagcttcgc catttcctgc    1620
tttctgctgt gcgtggctct gctgggattc attatgtggg cctgtcagaa aggaaatatt     1680
cggtgtaaca tttgcatctg ataa                                            1704
```

<210> SEQ ID NO 30
<211> LENGTH: 566
<212> TYPE: PRT
<213> ORGANISM: Artificial Sequence
<220> FEATURE:
<223> OTHER INFORMATION: H3HA-V4 protein Sequence

<400> SEQUENCE: 30

```
Met Lys Thr Ile Ile Ala Leu Ser Tyr Ile Leu Cys Leu Val Phe Ala
 1               5                  10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Asn Asp Gln Ile
        195                 200                 205
```

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
            355                 360                 365

Phe Arg His Gln Asn Ser Glu Gly Ile Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 31
<211> LENGTH: 1755
<212> TYPE: DNA
<213> ORGANISM: Artificial Sequence
<220> FEATURE:
<223> OTHER INFORMATION: B-HA-V3 DNA Sequence

<400> SEQUENCE: 31

```
atgaaggcta ttattgtcct gctgatggtc gtcacatcta acgctgatcg catctgcacc    60
ggaattacct cctctaactc tcctcacgtg gtcaagacag ccactcaggg agaagtgaat   120
gtcaccggcg tgatccctct gaccacaact ccaacaaagt cccactttgc taacctgaag   180
gggaccaaaa caaggggaaa actgtgcccc aactgtctga attgcaccga cctggatgtg   240
gccctggggc gccctatgtg catcggaacc acaccatcag caaaagccag cattctgcac   300
gaggtgcgac ccgtcacttc tggctgcttc cctatcatgc atgaccggac caagattaga   360
cagctgccta atctgctgag ggggtacgaa aacatccgcc tgtccactca taacgtgatt   420
aatgctgagc gagcaccagg cgggccatat cgactgggca cttccggatc ttgtcccaac   480
gtgaccagtc gctcaggctt ctttgccaca atggcttggg cagtccctcg agacaacaag   540
actgctacca atcccctgac agtggaagtc ccttacatct gcaccaaagg ggaggaccag   600
attacagtgt ggggatttca cagcgataac aagacacaga tgaaaaatct gtacggggat   660
tccaaccccc agaagttcac cagctccgcc aatggagtga ctaccattta tgtctcccag   720
atcggaggct tcccaaacca gaccgaggac ggggactgc cacagtctgg ccgcatcgtg    780
gtcgattaca tggtgcagaa gcctggaaaa acaggcacta tcgtgtacca gcggggagtc   840
ctgctgccac agaaagtgtg gtgtgcttct ggcagaagta aggtcatcaa aggcagtctg   900
ccactgattg gggaagcaga ctgcctgcac gagaagtatg gcgggctgaa taagtccaaa   960
ccctactata ccggagaaca tgccaaagct atcggcaatt gtccaatttg ggtgaagact  1020
cccctgaaac tggcaaacgg caccaagtac agacccctg ccaagctgct gaaagagagg   1080
gggttctttg gagcaatcgc cggctttctg aaggaggct gggagggat gattgccggc    1140
tggcacgggt atacatctca cggagcacat ggagtggctg tcgcagctga cctgaagagt  1200
acacaggaag ctatcaacaa gatcactaag aacctgaata gcctgtccga gctggaagtg  1260
aaaaatctgc agcgcctgag cggcgccatg gatgagctgc ataacgagat cctgaactg   1320
gacgagaagg tggacgatct gcgggctgat accatctcta gtcagattga actggcagtc  1380
ctgctgagta cgagggaat cattaattca gaggatgaac acctgctggc actgaaaga    1440
aagctgaaga aaatgctggg gcctagcgcc gtggacatcg gaatggatg cttcgagact   1500
aagcataaat gtaaccagac ctgcctggat aggattgcag ccggcacctt caatgccggg  1560
gagttttccc tgccaacatt cgactctctg aacatcactc tgcatcact gaatgacgat   1620
ggcctggata ccacaccat tctgctgtac tatagcacag ccgcttcaag cctggccgtg  1680
acactgatga tcgctatttt catcgtgtat atggtgtcca gagataatgt ctcctgtagt  1740
atttgcctgt gataa                                                  1755
```

<210> SEQ ID NO 32
<211> LENGTH: 583
<212> TYPE: PRT
<213> ORGANISM: Artificial Sequence
<220> FEATURE:
<223> OTHER INFORMATION: B-HA-V3 protein Sequence

<400> SEQUENCE: 32

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45
```

-continued

Thr Thr Pro Thr Lys Ser His Phe Ala Asn Leu Lys Gly Thr Lys Thr
      50                  55                  60

Arg Gly Lys Leu Cys Pro Asn Cys Leu Asn Cys Thr Asp Leu Asp Val
65                  70                  75                  80

Ala Leu Gly Arg Pro Met Cys Ile Gly Thr Thr Pro Ser Ala Lys Ala
                    85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu Asn Ile Arg Leu Ser Thr His Asn Val Ile Asn Ala Glu Arg
            130                 135                 140

Ala Pro Gly Gly Pro Tyr Arg Leu Gly Thr Ser Gly Ser Cys Pro Asn
145                 150                 155                 160

Val Thr Ser Arg Ser Gly Phe Phe Ala Thr Met Ala Trp Ala Val Pro
                165                 170                 175

Arg Asp Asn Lys Thr Ala Thr Asn Pro Leu Thr Val Glu Val Pro Tyr
                180                 185                 190

Ile Cys Thr Lys Gly Glu Asp Gln Ile Thr Val Trp Gly Phe His Ser
            195                 200                 205

Asp Asn Lys Thr Gln Met Lys Asn Leu Tyr Gly Asp Ser Asn Pro Gln
            210                 215                 220

Lys Phe Thr Ser Ser Ala Asn Gly Val Thr Thr His Tyr Val Ser Gln
225                 230                 235                 240

Ile Gly Gly Phe Pro Asn Gln Thr Glu Asp Gly Gly Leu Pro Gln Ser
                245                 250                 255

Gly Arg Ile Val Val Asp Tyr Met Val Gln Lys Pro Gly Lys Thr Gly
                260                 265                 270

Thr Ile Val Tyr Gln Arg Gly Val Leu Leu Pro Gln Lys Val Trp Cys
            275                 280                 285

Ala Ser Gly Arg Ser Lys Val Ile Lys Gly Ser Leu Pro Leu Ile Gly
            290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
                340                 345                 350

Pro Ala Lys Leu Leu Lys Glu Arg Gly Phe Phe Gly Ala Ile Ala Gly
            355                 360                 365

Phe Leu Glu Gly Gly Trp Glu Gly Met Ile Ala Gly Trp His Gly Tyr
            370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
                420                 425                 430

Leu His Asn Glu Ile Leu Glu Leu Asp Glu Lys Val Asp Asp Leu Arg
            435                 440                 445

Ala Asp Thr Ile Ser Ser Gln Ile Glu Leu Ala Val Leu Leu Ser Asn
450                 455                 460

```
Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580

<210> SEQ ID NO 33
<211> LENGTH: 1761
<212> TYPE: DNA
<213> ORGANISM: Artificial Sequence
<220> FEATURE:
<223> OTHER INFORMATION: B-HA-V4 DNA Sequence

<400> SEQUENCE: 33
atgaaggcaa ttatcgtcct gctgatggtg gtgacctcaa acgccgacag aatctgcaca     60
ggcattacct cctcaaatag tccccatgtg gtcaagactg ccacccaggg ggaagtgaat    120
gtcactggag tgatccctct gaccacaact ccaaccaaat cccactttgc taacctgaag    180
ggcacaaaaa ctcgcgggaa gctgtgcccc aaatgtctga attgcaccga cctggatgtg    240
gctctgggcc gaccaaagtg tacagggaac atcccctctg caaaagtcag tattctgcac    300
gaggtgaggc ctgtcacaag tggatgcttc ccaatcatgc atgaccggac taagattaga    360
cagctgccta atctgctgag ggctacgaa cacatccgcc tgtccacaca taacgtgatt    420
aatgcagaga aggccccagg cgggccctat aaaatcggaa catccggctc ttgtccaaac    480
gtgactaacg ggaatggatt ctttgcaacc atggcatggg ccgtccccaa gaacgacaac    540
aacaagaccg ccacaaattc tctgaccatc gaagtgcctt acatttgcac tgagggcgaa    600
gaccagatca ccgtctgggg gtttcacagc gataacgaga ctcagatggc taagctgtac    660
ggcgattcca agccacagaa gttcaccagc agcgccaacg gggtgaccac acattatgtc    720
tcccagatcg gaggcttccc caatcagacc gaggacgggg gactgcctca gagtggacgg    780
attgtggtcg attacatggt gcagaagtca gggaaaactg gaaccatcac atatcagaga    840
gggattctgc tgccacagaa agtgtggtgt gccagcggaa ggtccaaggt catcaaagga    900
tccctgcccc tgattggcga agctgattgc ctgcacgaga agtatggcgg gctgaataag    960
tctaaaccct actatacagg ggaacatgct aaagcaatcg gaaactgtcc catttgggtg   1020
aagacacctc tgaaactggc caatggcact aagtaccgac cccctgctaa gctgctgaaa   1080
gagcggggct tctttggggc catcgctgga tttctggaag gaggctggga gggcatgatt   1140
gccggatggc acggctatac ctctcacggg gctcatggag tggcagtcgc cgctgacctg   1200
aagagtaccc aggaagccat caacaagatc acaaagaacc tgaatagtct gtcagagctg   1260
gaagtgaaaa acctgcagcg cctgagcggc gccatggatg agctgcataa tgagatcctg   1320
gaactggacg agaaggtgga cgatctgcgg gcagatacca tctctagtca gattgaactg   1380
```

```
gccgtgctgc tgtccaacga ggggatcatt aattctgagg acgaacacct gctggccctg   1440
gaaagaaagc tgaagaaaat gctgggccct agcgccgtgg aaatcggcaa cgggtgcttc   1500
gagacaaagc ataaatgtaa tcagacttgc ctggatagga ttgcagccgg aacattcaac   1560
gccggcgagt tttcactgcc aaccttcgac agcctgaata tcacagctgc atcactgaac   1620
gacgatggcc tggataatca cactattctg ctgtactata gcaccgccgc ttcaagcctg   1680
gccgtgactc tgatgatcgc catctttgtg gtgtatatgg tgtccaggga taacgtgtct   1740
tgtagcattt gtctgtgata a                                              1761
```

<210> SEQ ID NO 34
<211> LENGTH: 585
<212> TYPE: PRT
<213> ORGANISM: Artificial Sequence
<220> FEATURE:
<223> OTHER INFORMATION: B-HA-V4 protein Sequence

<400> SEQUENCE: 34

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Lys Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Lys
    130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285
```

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp His
370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asn Ala Gly Glu Phe Ser Leu Pro Thr
                515                 520                 525

Phe Asp Ser Leu Asn Ile Thr Ala Ala Ser Leu Asn Asp Asp Gly Leu
530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
                580                 585

<210> SEQ ID NO 35
<211> LENGTH: 1728
<212> TYPE: DNA
<213> ORGANISM: Artificial Sequence
<220> FEATURE:
<223> OTHER INFORMATION: H1U consensus DNA sequence

<400> SEQUENCE: 35
ggtaccaagc ttgccaccat gaaggtgaaa ctgctggtgc tgctgtgcac cttcaccgcc      60
acctacgccg acaccatctg catcggctac cacgccaaca acagcaccga caccgtggat     120
accgtgctgg aaaagaacgt gaccgtgacc cacagcgtga acctgctgga agatagccac     180
aacggcaagc tgtgcctgct gaaaggcatc gcccccctgc agctgggcaa ctgcagcgtg     240
gccggctgga tcctgggcaa ccccgagtgc gagctgctga tttccaaaga aagctggtcc     300
tacatcgtgg agacccccaa ccccgagaac ggcacctgct accccggcta cttcgccgac     360

-continued

```
tacgaggaac tgcgggagca gctgtccagc gtgagcagct cgagcggtt cgagatcttc      420 cccaaagaga gcagctggcc caaccacacc gtgaccggcg tgagcgccag ctgctcccac      480
aatggcaaga gcagcttcta ccggaacctg ctgtggctga ccggcaagaa cggcctgtac      540
cccaacctga gcaagagcta cgccaataac aaagaaaagg aagtgctggt gctgtggggc      600
gtgcaccacc ccccaacat cggcgaccag cgggccctgt accacaccga gaacgcctac       660
gtgagcgtgg tgtccagcca ctacagccgg cggttcaccc cgagatcgc caagcggccc       720 aaagtgcggg accaggaagg ccggatcaac tactactgga ccctgctgga acccggcgac      780
accatcatct cgaggccaa cggcaacctg atcgccccca gatacgcctt cgccctgagc       840
cggggcttcg gcagcggcat catcaccagc aacgccccca tggacgagtg cgacgccaag      900
tgccagaccc ctcagggagc tattaacagc agcctgccct tccagaacgt gcaccccgtg      960
accatcggcg agtgccccaa gtacgtgcgg agcgccaagc tgcggatggt gaccggcctg     1020
cggaacatcc ccagcatcca gagcaggggc ctgttcggcg ccatcgccgg cttcatcgag     1080
ggcggctgga ccggcatggt ggacgggtgg tacggctacc accaccagaa cgagcagggc     1140
agcggctacg ccgccgacca gaagagcacc cagaacgcca tcaacggcat caccaacaag     1200
gtgaacagcg tgatcgagaa gatgaacacc cagttcaccg ccgtgggcaa agagttcaac     1260
aagctggaac ggcggatgga aaacctgaac aagaaggtgg acgacggctt cctggacatc     1320
tggacctaca cgccgagct gctggtgctg ctggaaaacg agcggaccct ggacttccac      1380
gacagcaacg tgaagaacct gtacgagaag gtgaaaagcc agctgaagaa caacgccaaa     1440
gagatcggca acggctgctt cgagttctac cacaagtgca acgacgagtg catggaaagc     1500
gtgaagaatg gcacctacga ctaccccaag tacagcgagg aaagcaagct gaaccgggag     1560
aagatcgacg gcgtgaagct ggaaagcatg ggcgtgtacc agatcctggc catctacagc     1620
accgtcgctt ccagcctcgt cctgctcgtg tccctgggcg ccatctcctt ttggatgtgc     1680
agcaacggca gcctgcagtg ccggatctgc atctgatgac tcgagctc                 1728
```

<210> SEQ ID NO 36
<211> LENGTH: 565
<212> TYPE: PRT
<213> ORGANISM: Artificial Sequence
<220> FEATURE:
<223> OTHER INFORMATION: H1U consensus protein sequence

<400> SEQUENCE: 36

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125
```

```
Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540
```

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 37
<211> LENGTH: 1731
<212> TYPE: DNA
<213> ORGANISM: Artificial Sequence
<220> FEATURE:
<223> OTHER INFORMATION: H3HA1 consensus DNA sequence

<400> SEQUENCE: 37

| | |
|---|---:|
| ggtaccaagc ttgccaccat gaaaaccatc atcgccctga ctacatcct gtgcctggtg | 60 |
| ttcgcccaga gctgcccgg caacgacaac agcaccgcca ccctgtgtct gggccaccac | 120 |
| gccgtgccca acggcaccat cgtgaaaaca atcaccaacg accagatcga ggtgaccaac | 180 |
| gccaccgagc tggtgcagag cagcagcacc ggcggcatct gcacagccc ccaccagatc | 240 |
| ctggacggcg agaactgcac cctgatcgac gccctgctgg cgaccctca gtgcgacggc | 300 |
| ttccagaaca aaaagtggga cctgttcgtg gagcggagca aggcctacag caactgctac | 360 |
| ccctacgacg tgcccgacta cgccagcctg cggagcctgg tggccagcag cggcaccctg | 420 |
| gaattcaaca acgagagctt caactggacc ggcgtgaccc agaacggcac cagcagcgcc | 480 |
| tgcaagcggc ggagcaacaa cagcttcttt tccagactga actggctgac ccacctgaag | 540 |
| ttcaagtacc ccgccctgaa cgtgaccatg cccaacaatg agaagttcga caagctgtac | 600 |
| atctggggcg tgcaccaccc cggcaccgac aatgaccaga tcagcctgta cgcccaggcc | 660 |
| agcggccgga tcaccgtgag caccaagcgg agccagcaga ccgtgatccc caacatcggc | 720 |
| agccggccca gagtgagaga catccccagc cggatcagca tctactggac aatcgtgaag | 780 |
| cccggcgaca tcctgctgat caactccacc ggcaacctga tcgcccccag gggctacttc | 840 |
| aagatcagaa gcggcaagag cagcatcatg cggagcgacg cccccatcgg caagtgcaac | 900 |
| agcgagtgca tcacccccaa tggcagcatc cccaacgaca gcccttcca gaacgtgaac | 960 |
| cggatcacct acgccgcctg ccccagatac gtgaagcaga caccctgaa gctggccacc | 1020 |
| ggcatgcgga acgtgcccga gaagcagacc cggggcatct tcggcgccat cgccggcttc | 1080 |
| atcgagaacg gctgggaggg catggtggac ggtggtacg gcttccggca ccagaactcc | 1140 |
| gagggcatcg gccaggccgc cgacctgaag agcacccagg ccgccatcaa ccagatcaac | 1200 |
| ggcaagctga accggctgat cggcaagacc aacgagaagt ccaccagat cgaaaaagaa | 1260 |
| ttcagcgagg tggagggccg gatccaggac ctggaaaagt acgtggagga caccaagatc | 1320 |
| gacctgtgga gctacaacgc cgagctgctg gtcgccctgg aaaaccagca caccatcgac | 1380 |
| ctgaccgaca gcgagatgaa caagctgttc gagcggacca gaagcagct gcgggagaac | 1440 |
| gccgaggaca tgggcaacgg ctgctttaag atctaccaca gtgcgacaa cgcctgcatc | 1500 |
| ggcagcatcc ggaacggcac ctacgaccac gacgtgtacc gggacgaggc cctgaacaac | 1560 |
| cggttccaga tcaagggcgt ggagctgaag agcggctaca aggactggat cctgtggatc | 1620 |
| agcttcgcca tcagctgctt tctgctgtgc gtggccctgc tgggattcat catgtgggcc | 1680 |
| tgccagaagg gcaacatccg ctgcaacatc tgcatctgat gactcgagct c | 1731 |

<210> SEQ ID NO 38
<211> LENGTH: 566
<212> TYPE: PRT
<213> ORGANISM: Artificial Sequence
<220> FEATURE:
<223> OTHER INFORMATION: H3HA1 consensus protein sequence

<400> SEQUENCE: 38

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

```
Ile Gly Lys Thr Asn Glu Lys Phe His Gln Ile Glu Lys Glu Phe Ser
            405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
        450                 455                 460
Glu Arg Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
            485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
        530                 535                 540
Val Ala Leu Leu Gly Phe Ile Met Trp Ala Cys Gln Lys Gly Asn Ile
545                 550                 555                 560
Arg Cys Asn Ile Cys Ile
                565
```

INFLUENZA NUCLEIC ACID MOLECULES AND VACCINES MADE THEREFROM

CROSS-REFERENCE TO RELATED APPLICATIONS

This application is the U.S. national stage application filed under 35 U.S.C. § 371 claiming benefit to International Patent Application No. PCT/US14/024363, filed Mar. 12, 2014, which is entitled to priority under 35 U.S.C. § 119(e) to U.S. Provisional Application No. 61/787,182, filed Mar. 15, 2013, each of which is hereby incorporated by reference in its entirety.

FIELD OF THE INVENTION

The present invention relates to improved influenza viral vaccines, improved methods for inducing immune responses against influenza, improved methods for diagnosing vaccinated vs. infected influenza mammalian hosts and for prophylactically and/or therapeutically immunizing individuals against influenza.

BACKGROUND OF THE INVENTION

Influenza, commonly referred to as the flu, is an infectious disease caused by RNA viruses of the family Orthomyxoviridae. Influenza or flu viruses infect birds and mammals. Three of the five genera of Orthomyxoviridae are influenza viruses: Influenza A, Influenza B and Influenza C. Of these, Influenza A is the most common.

Influenza is typically transmitted through the air in aerosols produced by coughs or sneezes and by direct contact with body fluids containing the virus or contaminated surfaces. Seasonal epidemics of influenza occur worldwide and result in hundreds of thousands of deaths annually. In some years, pandemics occur and cause millions of deaths. In addition, livestock, particularly poultry and swine, are also susceptible to annual epidemics and occasional pandemics which cause large numbers of animal deaths and monetary losses.

Structurally, influenza viruses are similar, having generally spherical or filamentous virus particles of about 80-120 nm made up of similar molecular component. A central core comprising viral proteins and viral RNA is covered by a viral envelope made up of two different glycoproteins and a lipid coat derived from the cell that the viral particle is produced in. Two additional different glycoproteins are anchored within the viral envelope and include portions which project outward on the surface.

The influenza virus RNA genome is typically provided as eight different single stranded, negative sense RNA segments that together make up the genome's eleven viral genes which encode the eleven proteins (HA, NA, NP, M1, M2, NS1, NEP, PA, PB1, PB1-F2, PB2). The eight RNA segments are: 1) HA, which encodes hemagglutinin (about 500 molecules of hemagglutinin are needed to make one virion); 2) NA, which encodes neuraminidase (about 100 molecules of neuraminidase are needed to make one virion); 3) NP, which encodes nucleoprotein; 4) M, which encodes two matrix proteins (the M1 and the M2) by using different reading frames from the same RNA segment (about 3000 matrix protein molecules are needed to make one virion); 5) NS, which encodes two distinct non-structural proteins (NS1 and NEP) by using different reading frames from the same RNA segment; 6) PA, which encodes an RNA polymerase; 7) PB1, which encodes an RNA polymerase and PB1-F2 protein (induces apoptosis) by using different reading frames from the same RNA segment; and 8) PB2, which encodes an RNA polymerase.

Of these eleven proteins, hemagglutinin (HA) and neuraminidase (NA) are two large glycoproteins anchored in the viral envelope and present on the outer surface of the viral particles. These proteins serve as immunogens for immune responses against influenza. HA, which is a lectin that mediates binding of the virus to target cells and entry of the viral genome into the target cell, is expressed as a single gene product, HA0, and later processed by host proteases to produce two subunits, HA1 and HA2, which together form a complex on the surface of influenza viral particles. NA is involved in the release of newly produced mature viral particles produced in infected cells.

There are sixteen known HA serotypes and nine known NA serotypes for Influenza A viruses. The identity of the different serotypes present in a viral particle typically is used to describe a virus. For example, H1N1 is an influenza virus with HA serotype H1 and NA serotype N1; H5N1 is an influenza virus with HA serotype H5 and NA serotype N1. Only H1, H2 and H3 serotypes, and N1 and N2 serotypes usually infect humans.

Influenza strains are generally species or genus specific; i.e. an influenza strain which can infect pigs (a swine influenza virus) typically does not infect humans or birds; an influenza strain which can infect birds (an avian influenza virus) does not infect humans or pigs; and an influenza strain which can infect humans (a human influenza virus) does not infect birds or pigs. Influenza strains, however, can mutate and become infective from one species to another. For example, a strain which only infects pigs, a swine influenza, can mutate or recombine to become a strain that can infect humans only or both pigs and humans. A flu virus commonly referred to as "swine flu" is an influenza virus strain, such as an H1N1 strain, which can infect humans and which was derived from a strain that was previously specific for pigs (i.e. a swine flu virus is a swine origin human influenza or swine derived human influenza). A flu virus commonly referred to as "bird flu" is an influenza virus strain, such as an H5N1 strain, which can infect humans and which was derived from a strain that was previously specific for birds (i.e. a bird flu virus avian origin human influenza or avian derived human influenza).

Vaccinations against influenza are provided seasonally to many humans in developed countries and sometime to livestock. The vaccines used are limited in their protective results because the immune responses induced by the vaccines are specific for certain subtypes of virus. Different influenza vaccines are developed and administered annually based upon international surveillance and scientists' estimations of which types and strains of viruses will circulate in a given year. The virus changes significantly by mutation, recombination and reassortment of the segments. Thus, vaccines given in one year are not considered protective against the seasonal strains that are widely transmitted the following year.

The "flu shot" commonly promoted U.S. Centers for Disease Control and Prevention usually contains three killed/inactivated influenza viruses: one A (H3N2) virus, one A (H1N1) virus, and one B virus. Thus, it is apparent that vaccinations are limited to predictions of subtypes, and the availability of a specific vaccine to that subtype.

The direct administration of nucleic acid sequences to vaccinate against animal and human diseases has been studied and much effort has focused on effective and efficient means of nucleic acid delivery in order to yield necessary expression of the desired antigens, resulting immunogenic response and ultimately the success of this technique.

DNA vaccines have many conceptual advantages over more traditional vaccination methods, such as live attenuated viruses and recombinant protein-based vaccines. DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome. Ann N Y Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platform's immunogenicity when moving to larger animals [Liu, M. A. and J. B. Ulmer, Human clinical trials of plasmid DNA vaccines. Adv Genet, 2005. 55: p. 25-40]. Recent technological advances in the engineering of DNA vaccine immunogen, such has codon optimization, RNA optimization and the addition of immunoglobulin leader sequences have improved expression and immunogenicity of DNA vaccines [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al, Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. In addition, studies have suggested that the use of consensus immunogens can be able to increase the breadth of the cellular immune response as compared to native antigens alone [Yan, J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14].

One method for delivering nucleic acid sequences such as plasmid DNA is the electroporation (EP) technique. The technique has been used in human clinical trials to deliver anti-cancer drugs, such as bleomycin, and in many preclinical studies on a large number of animal species.

There remains a need for an immunogenic influenza consensus hemagglutinin protein, for nucleic acid constructs that encode such a protein and for compositions useful to induce immune responses in mammals that are broadly cross reactive against multiple strains of influenza. There remains a need for effective vaccines against influenza that are economical and effective across numerous influenza subtypes for treating individuals, including ability to cross protect against multiple strains of influenza.

SUMMARY OF THE INVENTION

The invention provides a multiple consensus subtype vaccine wherein the vaccine provides cross-reactivity against a variety of influenza strains. In one embodiment, the vaccine comprising at least one consensus hemagglutinin antigen.

In one embodiment, the consensus hemagglutinin antigen is selected from the group consisting of H1 hemagglutinin, H2 hemagluttinin, H3 hemagglutinin, and influenza B hemagglutinin, and any combination thereof.

In one embodiment, the H1 hemagglutinin is selected from the group consisting of HS09, H1Bris, H1TT, H1U, and any combination thereof.

In one embodiment, the H3 hemagglutinin is selected from the group consisting of H3HA-1, H3HA-2, and any combination thereof.

In one embodiment, the influenza B hemagglutinin is selected from the group consisting of BHA-1, BHA-2, and any combination thereof In one embodiment, HS09 comprises a nucleic acid sequence selected from the group consisting of a nucleic acid sequence encoding SEQ ID NO:2, a nucleic acid sequence that is at least 95% homologous to nucleic acid sequences encoding SEQ ID NO:2; a fragment of nucleic acid sequences encoding SEQ ID NO:2; a nucleic acid sequence that is at least 95% homologous to a fragment of nucleic acid sequences encoding SEQ ID NO:2.

In one embodiment, H1Bris comprises a nucleic acid sequence selected from the group consisting of a nucleic acid sequence encoding SEQ ID NO:20, a nucleic acid sequence that is at least 95% homologous to nucleic acid sequences encoding SEQ ID NO:20; a fragment of nucleic acid sequences encoding SEQ ID NO:20; a nucleic acid sequence that is at least 95% homologous to a fragment of nucleic acid sequences encoding SEQ ID NO:20.

In one embodiment, H1TT comprises a nucleic acid sequence selected from the group consisting of a nucleic acid sequence encoding SEQ ID NO:22, a nucleic acid sequence that is at least 95% homologous to nucleic acid sequences encoding SEQ ID NO:22; a fragment of nucleic acid sequences encoding SEQ ID NO:22; a nucleic acid sequence that is at least 95% homologous to a fragment of nucleic acid sequences encoding SEQ ID NO:22.

In one embodiment, H1U comprises a nucleic acid sequence selected from the group consisting of a nucleic acid sequence encoding SEQ ID NO:36, a nucleic acid sequence that is at least 95% homologous to nucleic acid sequences encoding SEQ ID NO:36; a fragment of nucleic acid sequences encoding SEQ ID NO:36; a nucleic acid sequence that is at least 95% homologous to a fragment of nucleic acid sequences encoding SEQ ID NO:36.

In one embodiment, HS09 comprises a nucleic acid sequence selected from the group consisting of SEQ ID NO:1, a nucleic acid sequence that is at least 95% homologous to SEQ ID NO:1; a fragment of SEQ ID NO:1; a nucleic acid sequence that is at least 95% homologous to a fragment of SEQ ID NO:1.

In one embodiment, H1Bris comprises a nucleic acid sequence selected from the group consisting of SEQ ID NO:19, a nucleic acid sequence that is at least 95% homologous to SEQ ID NO:19; a fragment of SEQ ID NO:19; a nucleic acid sequence that is at least 95% homologous to a fragment of SEQ ID NO:19.

In one embodiment, H1TT comprises a nucleic acid sequence selected from the group consisting of SEQ ID NO:21, a nucleic acid sequence that is at least 95% homologous to SEQ ID NO:21; a fragment of SEQ ID NO:21; a nucleic acid sequence that is at least 95% homologous to a fragment of SEQ ID NO:21

In one embodiment, H1U comprises a nucleic acid sequence selected from the group consisting of SEQ ID NO:35, a nucleic acid sequence that is at least 95% homologous to SEQ ID NO:35; a fragment of SEQ ID NO:35; a nucleic acid sequence that is at least 95% homologous to a fragment of SEQ ID NO:35.

In one embodiment, H3HA-1 comprises a nucleic acid sequence selected from the group consisting of a nucleic acid sequence encoding SEQ ID NO:38, a nucleic acid sequence that is at least 95% homologous to nucleic acid sequences encoding SEQ ID NO:38; a fragment of nucleic acid sequences encoding SEQ ID NO:38; a nucleic acid sequence that is at least 95% homologous to a fragment of nucleic acid sequences encoding SEQ ID NO:38.

In one embodiment, H3HA-2 comprises a nucleic acid sequence selected from the group consisting of a nucleic acid sequence encoding SEQ ID NO:24, a nucleic acid sequence that is at least 95% homologous to nucleic acid sequences encoding SEQ ID NO:24; a fragment of nucleic acid sequences encoding SEQ ID NO:24; a nucleic acid sequence that is at least 95% homologous to a fragment of nucleic acid sequences encoding SEQ ID NO:24.

In one embodiment, H3HA-1 comprises a nucleic acid sequence selected from the group consisting of SEQ ID NO:37, a nucleic acid sequence that is at least 95% homologous to SEQ ID NO:37; a fragment of SEQ ID NO:37; a nucleic acid sequence that is at least 95% homologous to a fragment of SEQ ID NO:37.

In one embodiment, H3HA-2 comprises a nucleic acid sequence selected from the group consisting of SEQ ID NO:23, a nucleic acid sequence that is at least 95% homologous to SEQ ID NO:23; a fragment of SEQ ID NO:23; a nucleic acid sequence that is at least 95% homologous to a fragment of SEQ ID NO:23.

In one embodiment, BHA-1 comprises a nucleic acid sequence selected from the group consisting of a nucleic acid sequence encoding SEQ ID NO:14, a nucleic acid sequence that is at least 95% homologous to nucleic acid sequences encoding SEQ ID NO:14; a fragment of nucleic acid sequences encoding SEQ ID NO:14; a nucleic acid sequence that is at least 95% homologous to a fragment of nucleic acid sequences encoding SEQ ID NO:14.

In one embodiment, BHA-2 comprises a nucleic acid sequence selected from the group consisting of a nucleic acid sequence encoding SEQ ID NO:26, a nucleic acid sequence that is at least 95% homologous to nucleic acid sequences encoding SEQ ID NO:26; a fragment of nucleic acid sequences encoding SEQ ID NO:26; a nucleic acid sequence that is at least 95% homologous to a fragment of nucleic acid sequences encoding SEQ ID NO:26.

In one embodiment, BHA-1 comprises a nucleic acid sequence selected from the group consisting of SEQ ID NO:13, a nucleic acid sequence that is at least 95% homologous to SEQ ID NO:13; a fragment of SEQ ID NO:13; a nucleic acid sequence that is at least 95% homologous to a fragment of SEQ ID NO:13.

In one embodiment, BHA-2 comprises a nucleic acid sequence selected from the group consisting of SEQ ID NO:25, a nucleic acid sequence that is at least 95% homologous to SEQ ID NO:25; a fragment of SEQ ID NO:25; a nucleic acid sequence that is at least 95% homologous to a fragment of SEQ ID NO:25.

The invention also provides a method of inducing cross-reactivity against a variety of influenza strains in a mammal. In one embodiment, the method comprises administering to the mammal in need thereof a vaccine of the invention. In one embodiment, the vaccine of the invention comprises at least one consensus hemagglutinin antigen.

In one embodiment, each of the consensus hemagglutinin antigen is administered to the mammal separately. In one embodiment, each of the consensus hemagglutinin antigen is administered to the mammal simultaneously.

Provided herein are isolated nucleic acid molecules comprising a nucleic acid sequence selected from the group consisting of: SEQ ID NO:1, a nucleic acid sequence that is at least 95% homologous to SEQ ID NO:1; a fragment of SEQ ID NO:1; a nucleic acid sequence that is at least 95% homologous to a fragment of SEQ ID NO:1; SEQ ID NO:6; a nucleic acid sequence that is at least 95% homologous to SEQ ID NO:6; a fragment of SEQ ID NO:6; a nucleic acid sequence that is at least 95% homologous to a fragment of SEQ ID NO:6; SEQ ID NO:9, a nucleic acid sequence that is at least 95% homologous to SEQ ID NO:9; a fragment of SEQ ID NO:9; a nucleic acid sequence that is at least 95% homologous to a fragment of SEQ ID NO:9; SEQ ID NO:13; a nucleic acid sequence that is at least 95% homologous to SEQ ID NO:13; a fragment of SEQ ID NO:13; a nucleic acid sequence that is at least 95% homologous to a fragment of SEQ ID NO:13; SEQ ID NO:19; a nucleic acid sequence that is at least 95% homologous to SEQ ID NO:19; a fragment of SEQ ID NO:19; a nucleic acid sequence that is at least 95% homologous to a fragment of SEQ ID NO:19; SEQ ID NO:21; a nucleic acid sequence that is at least 95% homologous to SEQ ID NO:21; a fragment of SEQ ID NO:21; a nucleic acid sequence that is at least 95% homologous to a fragment of SEQ ID NO:21; SEQ ID NO:23; a nucleic acid sequence that is at least 95% homologous to SEQ ID NO:23; a fragment of SEQ ID NO:23; a nucleic acid sequence that is at least 95% homologous to a fragment of SEQ ID NO:23; SEQ ID NO:25; a nucleic acid sequence that is at least 95% homologous to SEQ ID NO:25; a fragment of SEQ ID NO:25; a nucleic acid sequence that is at least 95% homologous to a fragment of SEQ ID NO:25; SEQ ID NO:27; a nucleic acid sequence that is at least 95% homologous to SEQ ID NO:27; a fragment of SEQ ID NO:27; a nucleic acid sequence that is at least 95% homologous to a fragment of SEQ ID NO:27; SEQ ID NO:29; a nucleic acid sequence that is at least 95% homologous to SEQ ID NO:29; a fragment of SEQ ID NO:29; a nucleic acid sequence that is at least 95% homologous to a fragment of SEQ ID NO:29; SEQ ID NO:31; a nucleic acid sequence that is at least 95% homologous to SEQ ID NO:31; a fragment of SEQ ID NO:31; a nucleic acid sequence that is at least 95% homologous to a fragment of SEQ ID NO:31; SEQ ID NO:33; a nucleic acid sequence that is at least 95% homologous to SEQ ID NO:33; a fragment of SEQ ID NO:33; a nucleic acid sequence that is at least 95% homologous to a fragment of SEQ ID NO:33; SEQ ID NO:35; a nucleic acid sequence that is at least 95% homologous to SEQ ID NO:35; a fragment of SEQ ID NO:35; a nucleic acid sequence that is at least 95% homologous to a fragment of SEQ ID NO:35; and SEQ ID NO:37; a nucleic acid sequence that is at least 95% homologous to SEQ ID NO:37; a fragment of SEQ ID NO:37; a nucleic acid sequence that is at least 95% homologous to a fragment of SEQ ID NO:37.

In some aspects of the invention, there are isolated nucleic acid molecules selected from the group consisting of: nucleic acid sequences encoding SEQ ID NO:2, a nucleic acid sequence that is at least 95% homologous to nucleic acid sequences encoding SEQ ID NO:2; a fragment of nucleic acid sequences encoding SEQ ID NO:2; a nucleic acid sequence that is at least 95% homologous to a fragment of nucleic acid sequences encoding SEQ ID NO:2; nucleic acid sequences encoding SEQ ID NO:7; a nucleic acid sequence that is at least 95% homologous to nucleic acid sequences encoding SEQ ID NO:7; a fragment of nucleic acid sequences encoding SEQ ID NO:7; a nucleic acid sequence that is at least 95% homologous to a fragment of nucleic acid sequences encoding SEQ ID NO:7; nucleic acid sequences encoding SEQ ID NO:10, a nucleic acid sequence that is at least 95% homologous to nucleic acid sequences encoding SEQ ID NO:10; a fragment of nucleic acid sequences encoding SEQ ID NO:10; a nucleic acid sequence that is at least 95% homologous to a fragment of nucleic acid sequences encoding SEQ ID NO:10; nucleic acid sequences encoding SEQ ID NO:14; a nucleic acid sequence that is at least 95% homologous to nucleic acid sequences encoding SEQ ID NO:14; a fragment of nucleic acid sequences encoding SEQ ID NO:14; a nucleic acid sequence that is at least 95% homologous to a fragment of nucleic acid sequences encoding SEQ ID NO:14; nucleic acid sequences encoding SEQ ID NO:20; a nucleic acid sequence that is at least 95% homologous to nucleic acid sequences encoding SEQ ID NO:20; a fragment of nucleic acid sequences encoding SEQ ID NO:20; a nucleic acid sequence that is at least 95% homologous to a fragment of nucleic acid sequences encoding SEQ ID NO:20; nucleic acid sequences encoding SEQ ID NO:22; a nucleic acid sequence that is at least 95% homologous to nucleic acid sequences encoding SEQ ID NO:22; a fragment of nucleic acid sequences encoding SEQ ID NO:22; a nucleic acid sequence that is at least 95% homologous to a fragment of nucleic acid sequences encoding SEQ ID NO:22; nucleic acid sequences encoding SEQ ID NO:24; a nucleic acid sequence that is at least 95% homologous to nucleic acid sequences encoding SEQ ID NO:24; a fragment of nucleic acid sequences encoding SEQ ID NO:24; a nucleic acid sequence that is at least 95% homologous to a fragment of nucleic acid sequences encoding SEQ ID NO:24; nucleic acid sequences encoding SEQ ID NO:26; a nucleic acid sequence that is at least 95% homologous to nucleic acid sequences encoding SEQ ID NO:26; a fragment of nucleic acid sequences encoding SEQ ID NO:26; a nucleic acid sequence that is at least 95% homologous to a fragment of nucleic acid sequences encoding SEQ ID NO:26; nucleic acid sequences encoding SEQ ID NO:28; a nucleic acid sequence that is at least 95% homologous to nucleic acid sequences encoding SEQ ID NO:28; a fragment of nucleic acid sequences encoding SEQ ID NO:28; a nucleic acid sequence that is at least 95% homologous to a fragment of nucleic acid sequences encoding SEQ ID NO:28; nucleic acid sequences encoding SEQ ID NO:30; a nucleic acid sequence that is at least 95% homologous to nucleic acid sequences encoding SEQ ID NO:30; a fragment of nucleic acid sequences encoding SEQ ID NO:30; a nucleic acid sequence that is at least 95% homologous to a fragment of nucleic acid sequences encoding SEQ ID NO:30; nucleic acid sequences encoding SEQ ID NO:32; a nucleic acid sequence that is at least 95% homologous to nucleic acid sequences encoding SEQ ID NO:32; a fragment of nucleic acid sequences encoding SEQ ID NO:32; a nucleic acid sequence that is at least 95% homologous to a fragment of nucleic acid sequences encoding SEQ ID NO:32; nucleic acid sequences encoding SEQ ID NO:34; a nucleic acid sequence that is at least 95% homologous to nucleic acid sequences encoding SEQ ID NO:34; a fragment of nucleic acid sequences encoding SEQ ID NO:34; a nucleic acid sequence that is at least 95% homologous to a fragment of nucleic acid sequences encoding SEQ ID NO:34; nucleic acid sequences encoding SEQ ID NO:36; a nucleic acid sequence that is at least 95% homologous to nucleic acid sequences encoding SEQ ID NO:36; a fragment of nucleic acid sequences encoding SEQ ID NO:36; a nucleic acid sequence that is at least 95% homologous to a fragment of nucleic acid sequences encoding SEQ ID NO:36; and nucleic acid sequences encoding SEQ ID NO:38; a nucleic acid sequence that is at least 95% homologous to nucleic acid sequences encoding SEQ ID NO:38; a fragment of nucleic acid sequences encoding SEQ ID NO:38; a nucleic acid sequence that is at least 95% homologous to a fragment of nucleic acid sequences encoding SEQ ID NO:38.

Also provided are compositions comprising: a) one or more of a first nucleic acid sequence selected from the group consisting of one or more of: SEQ ID NO:1, a nucleic acid sequence that is at least 95% homologous to SEQ ID NO:1; a fragment of SEQ ID NO:1; a nucleic acid sequence that is at least 95% homologous to a fragment of SEQ ID NO:1; SEQ ID NO:6; a nucleic acid sequence that is at least 95% homologous to SEQ ID NO:6; a fragment of SEQ ID NO:6; a nucleic acid sequence that is at least 95% homologous to a fragment of SEQ ID NO:6; SEQ ID NO:9, a nucleic acid sequence that is at least 95% homologous to SEQ ID NO:9; a fragment of SEQ ID NO:9; a nucleic acid sequence that is at least 95% homologous to a fragment of SEQ ID NO:9; SEQ ID NO:13; a nucleic acid sequence that is at least 95% homologous to SEQ ID NO:13; a fragment of SEQ ID NO:13; a nucleic acid sequence that is at least 95% homologous to a fragment of SEQ ID NO:13; SEQ ID NO:19; a nucleic acid sequence that is at least 95% homologous to SEQ ID NO:19; a fragment of SEQ ID NO:19; a nucleic acid sequence that is at least 95% homologous to a fragment of SEQ ID NO:19; SEQ ID NO:21; a nucleic acid sequence that is at least 95% homologous to SEQ ID NO:21; a fragment of SEQ ID NO:21; a nucleic acid sequence that is at least 95% homologous to a fragment of SEQ ID NO:21; SEQ ID NO:23; a nucleic acid sequence that is at least 95% homologous to SEQ ID NO:23; a fragment of SEQ ID NO:23; a nucleic acid sequence that is at least 95% homologous to a fragment of SEQ ID NO:23; SEQ ID NO:25; a nucleic acid sequence that is at least 95% homologous to SEQ ID NO:25; a fragment of SEQ ID NO:25; a nucleic acid sequence that is at least 95% homologous to a fragment of SEQ ID NO:25; SEQ ID NO:27; a nucleic acid sequence that is at least 95% homologous to SEQ ID NO:27; a fragment of SEQ ID NO:27; a nucleic acid sequence that is at least 95% homologous to a fragment of SEQ ID NO:27; SEQ ID NO:29; a nucleic acid sequence that is at least 95% homologous to SEQ ID NO:29; a fragment of SEQ ID NO:29; a nucleic acid sequence that is at least 95% homologous to a fragment of SEQ ID NO:29; SEQ ID NO:31; a nucleic acid sequence that is at least 95% homologous to SEQ ID NO:31; a fragment of SEQ ID NO:31; a nucleic acid sequence that is at least 95% homologous to a fragment of SEQ ID NO:31; SEQ ID NO:33; a nucleic acid sequence that is at least 95% homologous to SEQ ID NO:33; a fragment of SEQ ID NO:33; a nucleic acid sequence that is at least 95% homologous to a fragment of SEQ ID NO:33; SEQ ID NO:35; a nucleic acid sequence that is at least 95% homologous to SEQ ID NO:35; a fragment of SEQ ID NO:35; a nucleic acid sequence that is at least 95% homologous to a fragment of SEQ ID NO:35; and SEQ ID NO:37; a nucleic acid sequence that is at least 95% homologous to SEQ ID NO:37; a fragment of SEQ ID NO:37; a nucleic acid sequence that is at least 95% homologous to a fragment of SEQ ID NO:37; and b) one or more of a second nucleic acid sequence that encodes a protein selected from the group consisting of one or more of: influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin, or neuraminidase, or fragments thereof.

Also provided are compositions comprising: a) one or more of a first nucleic acid sequence selected from the group consisting of one or more of: nucleic acid sequences encoding SEQ ID NO:2, a nucleic acid sequence that is at least 95% homologous to nucleic acid sequences encoding SEQ ID NO:2; a fragment of nucleic acid sequences encoding SEQ ID NO:2; a nucleic acid sequence that is at least 95% homologous to a fragment of nucleic acid sequences encoding SEQ ID NO:2; nucleic acid sequences encoding SEQ ID NO:7; a nucleic acid sequence that is at least 95% homologous to nucleic acid sequences encoding SEQ ID NO:7; a fragment of nucleic acid sequences encoding SEQ ID NO:7; a nucleic acid sequence that is at least 95% homologous to a fragment of nucleic acid sequences encoding SEQ ID NO:7; nucleic acid sequences encoding SEQ ID NO:10, a nucleic acid sequence that is at least 95% homologous to nucleic acid sequences encoding SEQ ID NO:10; a fragment of nucleic acid sequences encoding SEQ ID NO:10; a nucleic acid sequence that is at least 95% homologous to a fragment of nucleic acid sequences encoding SEQ ID NO:10; nucleic acid sequences encoding SEQ ID NO:14; a nucleic acid sequence that is at least 95% homologous to nucleic acid sequences encoding SEQ ID NO:14; a fragment of nucleic acid sequences encoding SEQ ID NO:14; a nucleic acid sequence that is at least 95% homologous to a fragment of nucleic acid sequences encoding SEQ ID NO:14; nucleic acid sequences encoding SEQ ID NO:20; a nucleic acid sequence that is at least 95% homologous to nucleic acid sequences encoding SEQ ID NO:20; a fragment of nucleic acid sequences encoding SEQ ID NO:20; a nucleic acid sequence that is at least 95% homologous to a fragment of nucleic acid sequences encoding SEQ ID NO:20; nucleic acid sequences encoding SEQ ID NO:22; a nucleic acid sequence that is at least 95% homologous to nucleic acid sequences encoding SEQ ID NO:22; a fragment of nucleic acid sequences encoding SEQ ID NO:22; a nucleic acid sequence that is at least 95% homologous to a fragment of nucleic acid sequences encoding SEQ ID NO:22; nucleic acid sequences encoding SEQ ID NO:24; a nucleic acid sequence that is at least 95% homologous to nucleic acid sequences encoding SEQ ID NO:24; a fragment of nucleic acid sequences encoding SEQ ID NO:24; a nucleic acid sequence that is at least 95% homologous to a fragment of nucleic acid sequences encoding SEQ ID NO:24; nucleic acid sequences encoding SEQ ID NO:26; a nucleic acid sequence that is at least 95% homologous to nucleic acid sequences encoding SEQ ID NO:26; a fragment of nucleic acid sequences encoding SEQ ID NO:26; a nucleic acid sequence that is at least 95% homologous to a fragment of nucleic acid sequences encoding SEQ ID NO:26; nucleic acid sequences encoding SEQ ID NO:28; a nucleic acid sequence that is at least 95% homologous to nucleic acid sequences encoding SEQ ID NO:28; a fragment of nucleic acid sequences encoding SEQ ID NO:28; a nucleic acid sequence that is at least 95% homologous to a fragment of nucleic acid sequences encoding SEQ ID NO:28; nucleic acid sequences encoding SEQ ID NO:30; a nucleic acid sequence that is at least 95% homologous to nucleic acid sequences encoding SEQ ID NO:30; a fragment of nucleic acid sequences encoding SEQ ID NO:30; a nucleic acid sequence that is at least 95% homologous to a fragment of nucleic acid sequences encoding SEQ ID NO:30; nucleic acid sequences encoding SEQ ID NO:32; a nucleic acid sequence that is at least 95% homologous to nucleic acid sequences encoding SEQ ID NO:32; a fragment of nucleic acid sequences encoding SEQ ID NO:32; a nucleic acid sequence that is at least 95% homologous to a fragment of nucleic acid sequences encoding SEQ ID NO:32; nucleic acid sequences encoding SEQ ID NO:34; a nucleic acid sequence that is at least 95% homologous to nucleic acid sequences encoding SEQ ID NO:34; a fragment of nucleic acid sequences encoding SEQ ID NO:34; a nucleic acid sequence that is at least 95% homologous to a fragment of nucleic acid sequences encoding SEQ ID NO:34; nucleic acid sequences encoding SEQ ID NO:36; a nucleic acid sequence that is at least 95% homologous to nucleic acid sequences encoding SEQ ID NO:36; a fragment of nucleic acid sequences encoding SEQ ID NO:36; a nucleic acid sequence that is at least 95% homologous to a fragment of nucleic acid sequences encoding SEQ ID NO:36; and nucleic acid sequences encoding SEQ ID NO:38; a nucleic acid sequence that is at least 95% homologous to nucleic acid sequences encoding SEQ ID NO:38; a fragment of nucleic acid sequences encoding SEQ ID NO:38; a nucleic acid sequence that is at least 95% homologous to a fragment of nucleic acid sequences encoding SEQ ID NO:38; and b) a second nucleic acid sequence that encodes a protein selected from the group consisting of one or more of: influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin, or neuraminidase, or fragments thereof.

In some aspects, there are vaccines that can have a combination as such:

a) one or more of a first influenza nucleic acid sequence H1 hemagglutinin capable of generating broadly cross reactive immune response in mammals against multiple strains of influenza virus, which is/are selected from the following:

a nucleic acid sequence selected from the group consisting of: SEQ ID NO:1, a nucleic acid sequence that is at least 95% homologous to SEQ ID NO:1; a fragment of SEQ ID NO:1; a nucleic acid sequence that is at least 95% homologous to a fragment of SEQ ID NO:1; SEQ ID NO:9, a nucleic acid sequence that is at least 95% homologous to SEQ ID NO:9; a fragment of SEQ ID NO:9; a nucleic acid sequence that is at least 95% homologous to a fragment of SEQ ID NO:9; SEQ ID NO:19; a nucleic acid sequence that is at least 95% homologous to SEQ ID NO:19; a fragment of SEQ ID NO:19; a nucleic acid sequence that is at least 95% homologous to a fragment of SEQ ID NO:19; SEQ ID NO:21; a nucleic acid sequence that is at least 95% homologous to SEQ ID NO:21; a fragment of SEQ ID NO:21; a nucleic acid sequence that is at least 95% homologous to a fragment of SEQ ID NO:21; SEQ ID NO:35; a nucleic acid sequence that is at least 95% homologous to SEQ ID NO:35; a fragment of SEQ ID NO:35; a nucleic acid sequence that is at least 95% homologous to a fragment of SEQ ID NO:35; nucleic acid sequences encoding SEQ ID NO:2, a nucleic acid sequence that is at least 95% homologous to nucleic acid sequences encoding SEQ ID NO:2; a fragment of nucleic acid sequences encoding SEQ ID NO:2; a nucleic acid sequence that is at least 95% homologous to a fragment of nucleic acid sequences encoding SEQ ID NO:2; nucleic acid sequences encoding SEQ ID NO:10, a nucleic acid sequence that is at least 95% homologous to nucleic acid sequences encoding SEQ ID NO:10; a fragment of nucleic acid sequences encoding SEQ ID NO:10; a nucleic acid sequence that is at least 95% homologous to a fragment of nucleic acid sequences encoding SEQ ID NO:10; nucleic acid sequences encoding SEQ ID NO:20; a nucleic acid sequence that is at least 95% homologous to nucleic acid sequences encoding SEQ ID NO:20; a fragment of nucleic acid sequences encoding SEQ ID NO:20; a nucleic acid sequence that is at least 95% homologous to a fragment of nucleic acid sequences encoding SEQ ID NO:20; nucleic acid sequences encoding SEQ ID NO:22; a nucleic acid sequence that is at least 95% homologous to nucleic acid sequences encoding SEQ ID NO:22; a fragment of nucleic acid sequences encoding SEQ ID NO:22; a nucleic acid sequence that is at least 95% homologous to a fragment of nucleic acid sequences encoding SEQ ID NO:22; nucleic acid sequences encoding SEQ ID NO:36; a nucleic acid sequence that is at least 95% homologous to nucleic acid sequences encoding SEQ ID NO:36; a fragment of nucleic acid sequences encoding SEQ ID NO:36; and a nucleic acid sequence that is at least 95% homologous to a fragment of nucleic acid sequences encoding SEQ ID NO:36.

b) one or more of a first influenza nucleic acid sequence H3 hemagglutinin capable of generating broadly cross reactive immune response in mammals against multiple strains of influenza virus, which is/are selected from the following:

a nucleic acid sequence selected from the group consisting of: SEQ ID NO:23, a nucleic acid sequence that is at least 95% homologous to SEQ ID NO:23; a fragment of SEQ ID NO:23; a nucleic acid sequence that is at least 95% homologous to a fragment of SEQ ID NO:23; SEQ ID NO:27, a nucleic acid sequence that is at least 95% homologous to SEQ ID NO:27; a fragment of SEQ ID NO:27; a nucleic acid sequence that is at least 95% homologous to a fragment of SEQ ID NO:27; SEQ ID NO:29; a nucleic acid sequence that is at least 95% homologous to SEQ ID NO:29; a fragment of SEQ ID NO:29; a nucleic acid sequence that is at least 95% homologous to a fragment of SEQ ID NO:29; SEQ ID NO:37; a nucleic acid sequence that is at least 95% homologous to SEQ ID NO:37; a fragment of SEQ ID NO:37; a nucleic acid sequence that is at least 95% homologous to a fragment of SEQ ID NO:37; nucleic acid sequences encoding SEQ ID NO:24, a nucleic acid sequence that is at least 95% homologous to nucleic acid sequences encoding SEQ ID NO:24; a fragment of nucleic acid sequences encoding SEQ ID NO:24; a nucleic acid sequence that is at least 95% homologous to a fragment of nucleic acid sequences encoding SEQ ID NO:24; nucleic acid sequences encoding SEQ ID NO:28; a nucleic acid sequence that is at least 95% homologous to nucleic acid sequences encoding SEQ ID NO: 28; a fragment of nucleic acid sequences encoding SEQ ID NO: 28; a nucleic acid sequence that is at least 95% homologous to a fragment of nucleic acid sequences encoding SEQ ID NO: 28; nucleic acid sequences encoding SEQ ID NO:30; a nucleic acid sequence that is at least 95% homologous to nucleic acid sequences encoding SEQ ID NO: 30; a fragment of nucleic acid sequences encoding SEQ ID NO: 30; a nucleic acid sequence that is at least 95% homologous to a fragment of nucleic acid sequences encoding SEQ ID NO: 30; nucleic acid sequences encoding SEQ ID NO:38; a nucleic acid sequence that is at least 95% homologous to nucleic acid sequences encoding SEQ ID NO: 38; a fragment of nucleic acid sequences encoding SEQ ID NO: 38; and a nucleic acid sequence that is at least 95% homologous to a fragment of nucleic acid sequences encoding SEQ ID NO: 38.

c) one or more of a first influenza nucleic acid sequence influenza B hemagglutinin capable of generating broadly cross reactive immune response in mammals against multiple strains of influenza virus, which is/are selected from the following:

a nucleic acid sequence selected from the group consisting of: SEQ ID NO:13, a nucleic acid sequence that is at least 95% homologous to SEQ ID NO: 13; a fragment of SEQ ID NO: 13; a nucleic acid sequence that is at least 95% homologous to a fragment of SEQ ID NO: 13; SEQ ID NO:25, a nucleic acid sequence that is at least 95% homologous to SEQ ID NO: 25; a fragment of SEQ ID NO: 25; a nucleic acid sequence that is at least 95% homologous to a fragment of SEQ ID NO: 25; SEQ ID NO:31; a nucleic acid sequence that is at least 95% homologous to SEQ ID NO: 31; a fragment of SEQ ID NO: 31; a nucleic acid sequence that is at least 95% homologous to a fragment of SEQ ID NO: 31; SEQ ID NO:33; a nucleic acid sequence that is at least 95% homologous to SEQ ID NO: 33; a fragment of SEQ ID NO: 33; a nucleic acid sequence that is at least 95% homologous to a fragment of SEQ ID NO: 33; nucleic acid sequences encoding SEQ ID NO:14, a nucleic acid sequence that is at least 95% homologous to nucleic acid sequences encoding SEQ ID NO: 14; a fragment of nucleic acid sequences encoding SEQ ID NO: 14; a nucleic acid sequence that is at least 95% homologous to a fragment of nucleic acid sequences encoding SEQ ID NO: 14; nucleic acid sequences encoding SEQ ID NO:26; a nucleic acid sequence that is at least 95% homologous to nucleic acid sequences encoding SEQ ID NO: 26; a fragment of nucleic acid sequences encoding SEQ ID NO: 26; a nucleic acid sequence that is at least 95% homologous to a fragment of nucleic acid sequences encoding SEQ ID NO: 26; nucleic acid sequences encoding SEQ ID NO:32; a nucleic acid sequence that is at least 95% homologous to nucleic acid sequences encoding SEQ ID NO: 32; a fragment of nucleic acid sequences encoding SEQ ID NO: 32; a nucleic acid sequence that is at least 95% homologous to a fragment of nucleic acid sequences encoding SEQ ID NO: 32; nucleic acid sequences encoding SEQ ID NO:34; a nucleic acid sequence that is at least 95% homologous to nucleic acid sequences encoding SEQ ID NO: 34; a fragment of nucleic acid sequences encoding SEQ ID NO: 34; and a nucleic acid sequence that is at least 95% homologous to a fragment of nucleic acid sequences encoding SEQ ID NO: 34.

Some aspects of the invention provide an expression vector comprising a nucleic acid sequence of the invention operably linked to a regulatory element.

Some aspects of the invention provide methods of inducing an immune response comprising the step of: administering to an individual such nucleic acid molecules and/or compositions.

Additional aspects of the invention provide methods of protecting an individual against infection. The methods comprise the step of: administering to said individual a prophylactically effective amount of a nucleic acid molecule comprising such nucleic acid sequence or compositions; wherein the nucleic acid sequence is expressed in cells of said individual and a protective immune response is induced against one or more strains of influenza. In some embodiment, the immune response is a protective immune response against swine origin human influenza.

In some aspects of the invention, methods are provided for treating an individual who has been infected by influenza. The methods comprise the step of: administering to said individual a therapeutically effective amount of such nucleic acid molecules and/or composition. In some embodiment, the immune response is broadly cross reactive against multiple strains of influenza.

BRIEF DESCRIPTION OF THE FIGURES

FIG. 1 is a map of the 2999 basepair backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1 that was used as the backbone for pGX2009:

C>G 241 in CMV promoter

C>T 1942 backbone, downstream of the bovine growth hormone polyadenylation signal (bGHpolyA)

A>- 2876 backbone, downstream of the Kanamycin gene

C>T 3277 in pUC origin of replication (Ori) high copy number mutation (see Nucleic Acid Research 1985)

G>C 3753 in very end of pUC Ori upstream of RNASeH site

Base pairs 2, 3 and 4 are changed from ACT to CTG in backbone, upstream of CMV promoter.

FIG. 2 shows two maps of the plasmid pGX2009, which is also referred to as pH1HA09. The nucleic acid sequence of the plasmid pGX2009 (SEQ ID NO:5) includes the coding sequence for the consensus H1 protein construct (amino acid SEQ ID NO:4 encoded by SEQ ID NO:3) which includes the IgE leader (amino acid SEQ ID NO:17) linked to the N terminal of the consensus H1 amino acid sequence (amino acid SEQ ID NO:2 encoded by SEQ ID NO:1) which is linked at its C terminal to the HA Tag (SEQ ID NO:18). The consensus H1 protein (amino acid SEQ ID NO:4 encoded by SEQ ID NO:3) is labeled SwiHum Con HA and H1HA09.

FIG. 3 shows a maps of the plasmid pGX2006. The nucleic acid sequence of the plasmid pGX2006 (SEQ ID NO:8) includes the coding sequence for consensus H2 protein (amino acid SEQ ID NO:7 encoded by SEQ ID NO:6) which is labeled H2HA.

FIG. 4 shows data from hemagglutination inhibition assays performed with sera from immunized ferrets.

FIG. 5 shows results of a challenge of immunized and unimmunized ferrets with a novel H1N1 strain.

FIG. 6 displays an influenza H1 hemagglutinin (H1HA) genetic tree of the genes of strains over the last 20 years, showing the genetic relationship between the various H1HA influenza strains.

FIGS. 7A-G displays a number of graphs of inhibition titers generated from hemagglutination inhibition assays performed with sera from immunized mice (naïve, H1U (SEQ ID NO: 35), HS09 (SEQ ID NO:1), ConBris (or H1Bris; SEQ ID NO:19), ConTT (or H1-TT; SEQ ID NO:21), Combo (all 4 H1U, HS09, ConBris, and ConTT)) against various seasonal viruses.

FIGS. 8A-C displays a number of graphs of inhibition titers generated from hemagglutination inhibition assays performed with sera from immunized mice (naïve, H1U (SEQ ID NO: 35), HS09 (SEQ ID NO:1), ConBris (or H1Bris; SEQ ID NO:19), ConTT (or H1-TT; SEQ ID NO:21), Combo (all 4 H1U, HS09, ConBris, and ConTT)) against various pandemic viruses.

FIGS. 9A-B displays a number of graphs of inhibition titers generated from hemagglutination inhibition assays performed with sera from immunized guinea pigs (Combo (all 4 H1U, HS09, ConBris, and ConTT)) against various seasonal viruses; 9A showing the data points; and 9B showing the mean and standard deviation.

FIGS. 10A-B displays a number of graphs of inhibition titers generated from hemagglutination inhibition assays performed with sera from immunized guinea pigs (Combo (all 4 H1U, HS09, ConBris, and ConTT)) against various pandemic viruses; 10A showing the data points; and 10B showing the mean and standard deviation.

FIGS. 11A-C shows titer graphs generated from humagglutination inhibition assays performed with sera from ferrets (immunized with combination of HS09 and H1U) against either 11A) A/Mexico/InDRE4108/2009 pandemic strain; and 11B) A/Mexico/InDRE4487/2009 pandemic strain; and a graph showing percent of ferrets survival when challenged with 2009 H1 Mexico strain of influenza.

FIG. 12 displays an influenza B hemagluttinin (BHA) genetic tree of the genes from strains of the last 20 years, showing the genetic relationship between the various BHA strains.

FIG. 13A-F displays a number of graphs of inhibition titers generated from hemagglutination inhibition assays performed with sera from immunized mice (naïve, BHA-1 (SEQ ID NO: 13), BHA-2 (SEQ ID NO:25), Combo (both BHA-1 and BHA-2) against various viruses.

FIG. 14A-C displays a number of graphs of inhibition titers generated from hemagglutination inhibition assays performed with sera from immunized mice (naïve, BHA-1 (SEQ ID NO: 13), BHA-2 (SEQ ID NO:25), Combo (both BHA-1 and BHA-2)) against various viruses.

FIG. 15A-D displays a number of graphs of inhibition titers generated from hemagglutination inhibition assays performed with sera from immunized guinea pigs pre-immunization ("pre"), post-dose 1 ("PD1"), post-dose 2 ("PD2"), or post-dose 3 ("PD3") (BHA-1 (SEQ ID NO: 13), BHA-2 (SEQ ID NO:25), Combo (both BHA-1 and BHA-2) against various viruses.

FIG. 16A-C displays a number of graphs of inhibition titers generated from hemagglutination inhibition assays performed with sera from immunized guinea pigs pre-immunization ("pre"), post-dose 1 ("PD1"), post-dose 2 ("PD2"), or post-dose 3 ("PD3") (BHA-1 (SEQ ID NO: 13), BHA-2 (SEQ ID NO:25), Combo (both BHA-1 and BHA-2) against various viruses.

FIG. 17A-C displays a number of graphs of inhibition titers generated from hemagglutination inhibition assays performed with sera from immunized guinea pigs pre-immunization ("pre"), post-dose 1 ("PD1"), post-dose 2 ("PD2"), or post-dose 3 ("PD3") (BHA-1 (SEQ ID NO: 13), BHA-2 (SEQ ID NO:25), Combo (both BHA-1 and BHA-2) against various viruses.

Note: for FIGS. 15A-D; 16A-C; and 17A-C "Combo" samples are guinea pigs that were immunized with combo separately (BHA-1 delivered separately from BHA-2); whereas with combo(mix) BHA-1 and BHA-2 were mixed and delivered simultaneously.

FIG. 18 displays an influenza H3 hemagluttinin (H3HA) genetic tree of the genes from strains of the last 20 years, showing the genetic relationship between the various H3HA strains.

FIG. 19A-E displays a number of graphs of inhibition titers generated from hemagglutination inhibition assays performed with sera from immunized mice (naïve, H3HA-1 (SEQ ID NO: 37), H3HA-2 (SEQ ID NO:23), Combo (both H3HA-1 and H3HA-2) against various viruses.

FIG. 20A-F displays a number of graphs of inhibition titers generated from hemagglutination inhibition assays performed with sera from immunized mice (naïve, H3HA-1 (SEQ ID NO: 37), H3HA-2 (SEQ ID NO:23), Combo (both H3HA-1 and H3HA-2) against various viruses.

DETAILED DESCRIPTION

Consensus amino acid sequences of each of influenza A H1 and H2 (referred to herein as "consensus H1S" or "HS09" (SEQ ID NO:2) and "consensus H2" or "H2HA" (SEQ ID NO:7), respectively), a synthetic hybrid consensus H1 influenza A hemagglutinin amino acid sequence (referred to herein as "consensus U2" or "H1U2" (SEQ ID NO:10)), a consensus amino acid sequence of influenza B hemagglutinin (referred to herein as "consensus BHA" or "BHA-1" (SEQ ID NO:14)), a consensus amino acid sequence H1Bris hemagluttinin "ConBris or "H1Bris" (SEQ ID NO:20), a consensus amino acid sequence H1TT hemagluttinin "ConTT" "H1TT" (SEQ ID NO:22), a consensus amino acid sequence H3 hemagluttinin or "H3HA-2" (SEQ ID NO:24), a consensus amino acid sequence influenza B hemagluttinin or "BHA-2" (SEQ ID NO:26), a consensus amino acid sequence H3 hemagluttinin or "H3HA-3" (SEQ ID NO:28), a consensus amino acid sequence H3 hemagluttinin or "H3HA-4" (SEQ ID NO:30), a consensus amino acid sequence influenza B hemagluttinin or "BHA-3" (SEQ ID NO:32), a consensus amino acid sequence influenza B hemagluttinin or "BHA-4" (SEQ ID NO:34), a synthetic hybrid consensus H1 influenza A hemagglutinin "consensus U" or "H1U" (SEQ ID NO:36), and a consensus amino acid sequence H3 hemagluttinin or "H3HA-1" (SEQ ID NO:38) are provided, which can provide protection of mammals against influenza. In addition, proteins are provided which comprise the consensus H1 amino acid sequence, the consensus H2 amino acid sequence, the consensus U2 amino acid sequence and/or the consensus BHA amino acid sequence. In some aspects, nucleic acid sequences are provided which encode proteins comprising the HS09 amino acid sequence (for example SEQ ID NO:1 or SEQ ID NO:3), the H2HA amino acid sequence (for example SEQ ID NO:6), the H1U2 amino acid sequence (for example SEQ ID NO:9 or SEQ ID NO:11), the BHA-1 amino acid sequence (for example SEQ ID NO:13 or SEQ ID NO:15), the H1Bris amino acid sequence (for example SEQ ID NO:19), the H1TT amino acid sequence (for example SEQ ID NO:21), the H3HA-2 amino acid sequence (for example SEQ ID NO:23), the BHA-2 amino acid sequence (for example SEQ ID NO:25), the H3HA-3 amino acid sequence (for example SEQ ID NO:27), the H3HA-4 amino acid sequence (for example SEQ ID NO:29), the BHA-3 amino acid sequence (for example SEQ ID NO:31), the BHA-4 amino acid sequence (for example SEQ ID NO:33), the H1U amino acid sequence (for example SEQ ID NO:35), and the H3HA-1 amino acid sequence (for example SEQ ID NO:37).

While not being bound by scientific theory, a vaccine that can be used to elicit an immune response (humeral, cellular, or both) broadly against multiple influenza subtypes may comprise one or more of the following: 1) a nucleic acid sequence that encodes a protein comprising the consensus H1HA amino acid sequence; 2) a protein comprising the consensus H1HA amino acid sequence; 3) a nucleic acid sequence that encodes a protein comprising the consensus H2HA amino acid sequence; 4) a protein comprising the consensus H2HA amino acid sequence; 5) a nucleic acid sequence that encodes a protein comprising the consensus H1U and/or H1U2 amino acid sequence; 6) a protein comprising the consensus H1U and/or H1U2 amino acid sequence; 7) a nucleic acid sequence that encodes a protein comprising the consensus BHA amino acid sequence; and 8) a protein comprising the consensus BHA amino acid sequence.

Immunization methods can be performed and vaccines can be prepared which use and/or combine two or more of the following components: 1) a nucleic acid sequence that encodes a protein comprising the consensus H1 amino acid sequence; 2) a protein comprising the consensus H1 amino acid sequence; 3) a nucleic acid sequence that encodes a protein comprising the consensus H2 amino acid sequence, 4) a protein comprising the consensus H2 amino acid sequence; 5) a nucleic acid sequence that encodes a protein comprising the consensus U2 amino acid sequence, 6) a protein comprising the consensus U2 amino acid sequence, 7) a nucleic acid sequence that encodes a protein comprising the consensus BHA amino acid sequence, and 8) a protein comprising the consensus BHA amino acid sequence. For more broad based treatments against influenza, immunization methods can be performed and vaccines can be prepared which use and/or combine one or more other influenza proteins such as influenza A H1-H16, influenza A N1-N9, influenza B hemagglutinin, influenza B neuraminidase and/or genes encoding these proteins together with one or more of the following components: 1) a nucleic acid sequence that encodes a protein comprising the consensus H1 amino acid sequence; 2) a protein comprising the consensus H1 amino acid sequence; 3) a nucleic acid sequence that encodes a protein comprising the consensus H2 amino acid sequence, 4) a protein comprising the consensus H2 amino acid sequence; 5) a nucleic acid sequence that encodes a protein comprising the consensus U2 amino acid sequence, 6) a protein comprising the consensus U2 amino acid sequence, 7) a nucleic acid sequence that encodes a protein comprising the consensus BHA amino acid sequence, and 8) a protein comprising the consensus BHA amino acid sequence.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein means any molecule added to the DNA plasmid vaccines described herein to enhance the immunogenicity of the antigens encoded by the DNA plasmids and the encoding nucleic acid sequences described hereinafter.

b. Antibody

"Antibody" as used herein means an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

d. Complement

"Complement" or "complementary" as used herein means a nucleic acid can mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein means a polypeptide sequence based on analysis of an alignment of multiple subtypes of a particular influenza antigen. Nucleic acid sequences that encode a consensus polypeptide sequence may be prepared. Vaccines comprising proteins that comprise consensus sequences and/or nucleic acid molecules that encode such proteins can be used to induce broad immunity against multiple subtypes or serotypes of a particular influenza antigen. Consensus influenza antigens can include influenza A consensus hemagglutinin amino acid sequences, including for example consensus H1, consensus H2, or influenza B consensus hemagglutinin amino acid sequences.

f. Constant Current

"Constant current" as used herein means a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

g. Current Feedback or Feedback

"Current feedback" or "feedback" can be used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback can be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop can be instantaneous as it is an analog closed-loop feedback.

h. Decentralized Current

"Decentralized current" as used herein means the pattern of electrical currents delivered from the various needle electrode arrays of the electroporation devices described herein, wherein the patterns minimize, or preferably eliminate, the occurrence of electroporation related heat stress on any area of tissue being electroporated.

i. Effective

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

j. Electroporation

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

k. Encoding

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

l. Feedback Mechanism

"Feedback mechanism" as used herein means a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism can be performed by an analog closed loop circuit.

m. Fragment

"Fragment" as used herein with respect to nucleic acid sequences means a nucleic acid sequence or a portion thereof, that encodes a polypeptide capable of eliciting an immune response in a mammal that cross reacts with a full length wild type strain influenza antigen, including, e.g., an influenza A H1 hemagglutinin, an influenza A H2 hemagglutinin or an influenza B hemagglutinin. The fragments can be DNA fragments selected from at least one of the various nucleotide sequences that encode the consensus amino acid sequences and constructs comprising such sequences, including SEQ ID NOS: 1, 6, 9, 13, 15, 19, 21, 23, 25, 27, 29, 31, 33, 35, and 37; and nucleotide sequences encoding SEQ ID NOs: 2, 7, 10, 14, 20, 22, 24, 26, 28, 30, 32, 34, 36, and 38. DNA fragments can comprise coding sequences for the immunoglobulin leader such as IgE or IgG sequences. The DNA fragments can be 30 or more nucleotides in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, 720 or more, 780 or more, 840 or more, 900 or more, 960 or more, 1020 or more, 1080 or more, 1140 or more, 1200 or more, 1260 or more, 1320 or more, 1380 or more, 1440 or more, 1500 or more, 1560 or more, 1620 or more, 1680 or more, 1740 or more, 1800 or more, 1860 or more, 1820 or more, 1880 or more, 1940 or more, 2000 or more, 2600 or more, 2700 or more, 2800 or more, 2900 or more, 2910 or more, 2920 or more, 2930 or more, 2931 or more, 2932 or more, 2933 or more, 2934 or more, 2935 or more, 2936 or more, 2937 or more, or 2938 or more in length. DNA fragments can be fewer than 10 nucleotides, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 720, fewer than 780, fewer than 840, fewer than 900, fewer than 960, fewer than 1020, fewer than 1080, fewer than 1140, fewer than 1200, fewer than 1260, fewer than 1320, fewer than 1380, fewer than 1440, fewer than 1500, fewer than 1560, fewer than 1620, fewer than 1680, or fewer than 1740 nucleotides, fewer than 1800, fewer than 1860, fewer than 1820, fewer than 1880, fewer than 1940, fewer than 2000, fewer than 2600, fewer than 2700, fewer than 2800, fewer than 2900, fewer than 2910, fewer than 2920, fewer than 2930, fewer than 2931, fewer than 2932, fewer than 2933, fewer than 2934, fewer than 2935, fewer than 2936, fewer than 2937, or fewer than 2938.

"Fragment" with respect to polypeptide sequences means a polypeptide capable of eliciting an immune response in a mammal that cross reacts with a full length wild type strain influenza antigen, including, e.g., an influenza A H1 hemagglutinin, an influenza A H2 hemagglutinin or an influenza B hemagglutinin. The fragment can be polypeptide fragment selected from at least one of the various polypeptide sequences of the present invention, including SEQ ID NOs: 2, 7, 10, 14, 20, 22, 24, 26, 28, 30, 32, 34, 36, and 38. Polypeptide fragments can be analyzed to contact at least one antigenic epitope as provided by a publicly available database such as the Los Alamos National Laboratory's HA Sequence Database. Polypeptides HA fragments can further comprise amino acid sequences for the immunoglobulin leader such as IgE or IgG. The polypeptide fragments can be 30 or more amino acids in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, or 710 amino acids or more in length. Polypeptide fragments can be fewer than 10 amino acids, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 700, fewer than 701, fewer than 702, fewer than 703, fewer than 704, fewer than 705, fewer than 706, fewer than 707, fewer than 708, fewer than 709, or fewer than 710 amino acids in length.

n. Genetic Construct

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

o. Identical

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

p. Impedance

"Impedance" can be used when discussing the feedback mechanism and can be converted to a current value according to Ohm's law, thus enabling comparisons with the preset current.

q. Immune Response

"Immune response" as used herein means the activation of a host's immune system, e.g., that of a mammal, in response to the introduction of antigen such as an influenza hemagglutinin consensus antigen. The immune response can be in the form of a cellular or humoral response, or both.

r. Nucleic Acid

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

s. Operably Linked "Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

t. Promoter

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

u. Stringent Hybridization Conditions

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

v. Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, 1440, 1530, 1620, 1710, 1800, 1890, 1980, 2070 or more nucleotides or amino acids, or that the two sequences hybridize under stringent hybridization conditions.

w. Substantially Identical

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, 1440, 1530, 1620, 1710, 1800, 1890, 1980, 2070 or more nucleotides or amino acids, or with respect to nucleic acids, if the first sequence is substantially complementary to the complement of the second sequence.

x. Subtype or Serotype

"Subtype" or "serotype": as used herein, interchangeably, and in reference to influenza virus, means genetic variants of an influenza virus such that one subtype is recognized by an immune system apart from a different subtype.

y. Variant

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

z. Vector

"Vector" as used herein means a nucleic acid sequence containing an origin of replication. A vector can be a vector, bacteriophage, bacterial artificial chromosome or yeast artificial chromosome. A vector can be a DNA or RNA vector. A vector can be a self-replicating extrachromosomal vector, and preferably, is a DNA plasmid.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

2. Influenza Antigen

Provided herein are antigens capable of eliciting an immune response in a mammal against one or more influenza serotypes. The antigen can be capable of eliciting an immune response in a mammal against one or more influenza serotypes, including against one or more pandemic strains, such as 2009 H1N1 swine originated influenza. The antigen can be capable of eliciting an immune response in a mammal against one or more influenza serotype, including against one or more strains of swine derived human influenza. The antigen can comprise epitopes that make them particularly effective as immunogens against which anti-influenza immune responses can be induced.

The antigen can comprise the full length translation product HA0, subunit HA1, subunit HA2, a variant thereof, a fragment thereof or a combination thereof. The influenza hemagglutinin antigen can be a consensus sequence derived from multiple strains of influenza A serotype H1, a consensus sequence derived from multiple strains of influenza A serotype H2, a hybrid sequence containing portions of two different consensus sequences derived from different sets of multiple strains of influenza A serotype H1 or a consensus sequence derived from multiple strains of influenza B. The influenza hemagglutinin antigen can be from influenza B. The antigen can contain at least one antigenic epitope that can be effective against particular influenza immunogens against which an immune response can be induced. The antigen may provide an entire repertoire of immunogenic sites and epitopes present in an intact influenza virus. The antigen may be a consensus hemagglutinin antigen sequence that can be derived from hemagglutinin antigen sequences from a plurality of influenza A virus strains of one serotype such as a plurality of influenza A virus strains of serotype H1 or of serotype H2. The antigen may be a hybrid consensus hemagglutinin antigen sequence that can be derived from combining two different consensus hemagglutinin antigen sequences or portions thereof. Each of two different consensus hemagglutinin antigen sequences may be derived from a different set of a plurality of influenza A virus strains of one serotype such as a plurality of influenza A virus strains of serotype H1. The antigen may be a consensus hemagglutinin antigen sequence that can be derived from hemagglutinin antigen sequences from a plurality of influenza B virus strains.

The consensus hemagglutinin antigen may be a protein comprising SEQ ID NO: 2 (the consensus H1 amino acid sequence) wherein amino acids 1-343 correspond to the HA1 subunit of the precursor HA0 consensus H1 amino acid sequence and amino acids 344-566 correspond to the HA2 subunit of the HA0 consensus H1 amino acid sequence. The consensus hemagglutinin antigen may also be a consensus hemagglutinin protein derived from hemagglutinin sequences from H1HA strains, such as a protein comprising SEQ ID NO: 20 (H1Bris) or SEQ ID NO:22 (H1TT). The consensus hemagglutinin antigen may be a protein comprising SEQ ID NO: 7 (H2HA). The consensus hemagglutinin antigen may be a consensus hemagglutinin protein derived from hemagglutinin sequences from H3HA strains, such as a protein comprising SEQ ID NO:24 (H3HA-2), SEQ ID NO:28 (H3HA-3), SEQ ID NO:30 (H3HA-4), or SEQ ID NO: 38 (H3HA-1). The consensus hemagglutinin antigen may be a synthetic hybrid consensus H1 sequences comprising portions of two different consensus H1 sequences which are each derived from a different set of sequences from the other. An example of a consensus HA antigen that is a synthetic hybrid consensus H1 protein is a protein comprising SEQ ID NO: 10 (H1U2) or SEQ ID NO:36 (H1U). The consensus hemagglutinin antigen may be a consensus hemagglutinin protein derived from hemagglutinin sequences from influenza B strains, such as a protein comprising SEQ ID NO: 14 (BHA-1), SEQ ID NO: 26 (BHA-2), SEQ ID NO: 32 (BHA-3), or SEQ ID NO: 34 (BHA-4).

The consensus hemagglutinin antigen may further comprise one or more additional amino acid sequence elements. The consensus hemagglutinin antigen may further comprise on its N-terminal an IgE or IgG leader amino acid sequence. The IgE leader amino acid sequence may be SEQ ID NO: 17. The consensus hemagglutinin antigen may further comprise an immunogenic tag which is a unique immunogenic epitope that can be detected by readily available antibodies. An example of such an immunogenic tag is the 9 amino acid influenza HA Tag which may be linked on the consensus hemagglutinin C terminus. The HA Tag amino acid sequence may be SEQ ID NO:18. In some embodiments, consensus hemagglutinin antigen may further comprise on its N-terminal an IgE or IgG leader amino acid sequence and on its C terminal an HA tag.

The consensus hemagglutinin antigen may be a consensus hemagglutinin protein that consists of consensus influenza amino acid sequences or fragments and variants thereof. The consensus hemagglutinin antigen may be a consensus hemagglutinin protein that comprises non-influenza protein sequences and influenza protein sequences or fragments and variants thereof.

Examples of a consensus H1 protein include those that may consist of the consensus H1 amino acid sequence (SEQ ID NO:2) or those that further comprise additional elements such as an IgE leader sequence, or an HA Tag or both an IgE leader sequence and an HA Tag. An example of the consensus H1 protein that includes both an IgE leader sequence and an HA Tag is SEQ ID NO: 4, which comprises the consensus H1 amino acid coding sequence (SEQ ID NO:2) linked to the IgE leader amino acid sequence (SEQ ID NO: 17) at its N terminal and linked to the HA Tag (SEQ ID NO:18) at its C terminal.

Examples of consensus H2 proteins include those that may consist of the consensus H2 amino acid sequence (SEQ ID NO:7) or those that further comprise an IgE leader sequence, or an HA Tag, or both an IgE leader sequence and an HA Tag.

Examples of hybrid consensus H1 proteins include those that may consist of the consensus U2 amino acid sequence (SEQ ID NO:10) or those that further comprise an IgE leader sequence, or an HA Tag, or both an IgE leader sequence and an HA Tag. An example of the consensus U2 protein is SEQ ID NO:12, which comprises the consensus U2 amino acid sequence (SEQ ID NO:10) linked to the IgE leader amino acid sequence (SEQ ID NO: 17) at its N terminal and linked to the HA Tag (SEQ ID NO:18) at its C terminal.

Examples of hybrid consensus influenza B hemagglutinin proteins include those that may consist of the consensus BHA amino acid sequence (SEQ ID NO:14) or it may comprise an IgE leader sequence, or a an HA Tag, or both an IgE leader sequence and an HA Tag. An example of the consensus BHA protein is SEQ ID NO:16 which comprises the consensus BHA amino acid sequence (SEQ ID NO:14) linked to the IgE leader amino acid sequence (SEQ ID NO: 17) at its N terminal and linked to the HA Tag (SEQ ID NO:18) at its C terminal.

The consensus hemagglutinin protein can be encoded by a consensus hemagglutinin nucleic acid, a variant thereof or a fragment thereof. Unlike the consensus hemagglutinin protein which may be a consensus sequence derived from a plurality of different hemagglutinin sequences from different strains and variants, the consensus hemagglutinin nucleic acid refers to a nucleic acid sequence that encodes a consensus protein sequence and the coding sequences used may differ from those used to encode the particular amino acid sequences in the plurality of different hemagglutinin sequences from which the consensus hemagglutinin protein sequence is derived. The consensus nucleic acid sequence may be codon optimized and/or RNA optimized. The consensus hemagglutinin nucleic acid sequence may comprise a Kozak's sequence in the 5' untranslated region. The consensus hemagglutinin nucleic acid sequence may comprise nucleic acid sequences that encode a leader sequence. The coding sequence of an N terminal leader sequence is 5' of the hemagglutinin coding sequence. The N-terminal leader can be facilitate secretion. The N-terminal leader can be an IgE leader or an IgG leader. The consensus hemagglutinin nucleic acid sequence can comprise nucleic acid sequences that encode an immunogenic tag. The immunogenic tag can be on the C terminus of the protein and the sequence encoding it is 3' of the HA coding sequence. The immunogenic tag provides a unique epitope for which there are readily available antibodies so that such antibodies can be used in assays to detect and confirm expression of the protein. The immunogenic tag can be an H Tag at the C-terminus of the protein.

Consensus hemagglutinin nucleic acid may have a polynucleotide sequence that encodes a protein that comprises the amino acid sequence of SEQ ID NO: 2, SEQ ID NO:7, SEQ ID NO:10, SEQ ID NO:14, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38. A consensus hemagglutinin nucleic acid that encodes SEQ ID NO: 2, SEQ ID NO:7, SEQ ID NO:10, SEQ ID NO:14, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38 can be SEQ ID NO:1, SEQ ID NO:6, SEQ ID NO:9, SEQ ID NO:13, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37 respectively. The consensus hemagglutinin nucleic acid can further comprise a polynucleotide sequence encoding the IgE leader amino acid sequence, or a polynucleotide sequence encoding an HA Tag amino acid sequence, or both. SEQ ID NO: 17 is an IgE leader polypeptide sequence. SEQ ID NO: 18 is an HA Tag polypeptide sequence. Examples of hemagglutinin consensus nucleic acids that further comprise polynucleotide sequences encoding an IgE leader sequence and an HA Tag include nucleic acid molecules that encode proteins that comprise the amino acid sequence of SEQ ID NO:4, SEQ ID NO:12 or SEQ ID NO:16. A consensus hemagglutinin nucleic acid that encodes SEQ ID NO:4, SEQ ID NO:12 or SEQ ID NO:16 may be SEQ ID NO:3, SEQ ID NO:11 or SEQ ID NO:15, respectively.

3. Genetic Constructs and Plasmids

Provided herein are genetic constructs that can comprise a nucleic acid sequence that encodes the hemagglutinin antigen. The genetic construct can be present in the cell as a functioning extrachromosomal molecule comprising the nucleic acid encoding the hemagglutinin antigen. The genetic construct comprising the nucleic acid encoding the hemagglutinin antigen can be linear minichromosome including centromere, telomers or plasmids or cosmids.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the hemagglutinin nucleic acid. The regulatory elements can be a promoter, an enhancer an initiation codon, a stop codon, or a polyadenylation signal.

Compositions can comprise nucleic acid sequences of one or more of: SEQ ID NO:1, SEQ ID NO:6, SEQ ID NO:9, SEQ ID NO:13, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37. Compositions can comprise a first nucleic acid sequence which encodes the hemagglutinin consensus antigen selected from the group consisting of one or more of: influenza A consensus hemagglutinin H1 antigen, influenza A consensus hemagglutinin H2 antigen, influenza A consensus hemagglutinin H1U and/or H1U2 antigen, and influenza B consensus hemagglutinin protein BHA, which can include SEQ ID NO:1, SEQ ID NO:6, SEQ ID NO:9, SEQ ID NO:13, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, or nucleic acid sequences that encode one or more of: SEQ ID NO:2, SEQ ID NO:7, SEQ ID NO:10, SEQ ID NO:14, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38; and can further comprise one or more additional nucleic acid sequence(s) that encodes one or more protein(s) selected from the group consisting of: influenza A hemagglutinin proteins H1, H2, H3, H4, H5, H6, H7, H8, H9, H10, H11, H12, H13, H14, H15, H16, influenza A neuraminidase N1, N2, N3, N4, N5, N6, N7, N8, N9, influenza B hemagglutinin (BHA) and influenza B neuraminidase (BNA), including one or more of the consensus sequences provided herein. The first and additional nucleic acid sequences may be present on the same nucleic acid molecule or different nucleic acid molecules. The first and additional nucleic acid sequences can be under the control of regulatory elements that function in a human cell. The additional coding sequence may encode one or more H1, H2, H3, H4, H5, H6, H7, H8, H9, H10, H11, H12, H13, H14, H15, H16, N1, N2, N3, N4, N5, N6, N7, N8, N9, BHA and BNA from one or more strains of influenza, or be a consensus derived from a plurality of strains having the serotype, or be a hybrid which includes sequences from two or more consensus sequences.

The nucleic acid sequences may make up a genetic construct that can be a vector. The vector can be capable of expressing a consensus hemagglutinin antigen in the cell of a mammal in a quantity effective to elicit an immune response in the mammal. The vector can be recombinant. The vector can comprise heterologous nucleic acid encoding the consensus hemagglutinin antigen. The vector can be a plasmid. The vector can be useful for transfecting cells with nucleic acid encoding a consensus hemagglutinin antigen, which the transformed host cell is cultured and maintained under conditions wherein expression of the consensus hemagglutinin antigen takes place.

The vector can comprise heterologous nucleic acid encoding a consensus hemagglutinin antigen and can further comprise an initiation codon, which can be upstream of the consensus hemagglutinin coding sequence, and a stop codon, which can be downstream of the consensus hemagglutinin coding sequence. The initiation and termination codon can be in frame with the consensus hemagglutinin coding sequence. The vector can also comprise a promoter that is operably linked to the consensus hemagglutinin coding sequence. The promoter operably linked to the consensus hemagglutinin coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the HA coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the consensus hemagglutinin coding. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1 (FIG. 1), pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 with changes such as those described in the paragraph referring to FIG. 1 in the Brief Description of the Figures section above. The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The consensus hemagglutinin coding sequence can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which can be used for protein production in mammalian cells such as Chinese hamster ovary (CHO) cells. The vector can be expression vectors or systems to produce protein by routine techniques and readily available starting materials including Sambrook et al., Molecular Cloning an Laboratory Manual, Second Ed., Cold Spring Harbor (1989), which is incorporated fully by reference.

Figure 2:
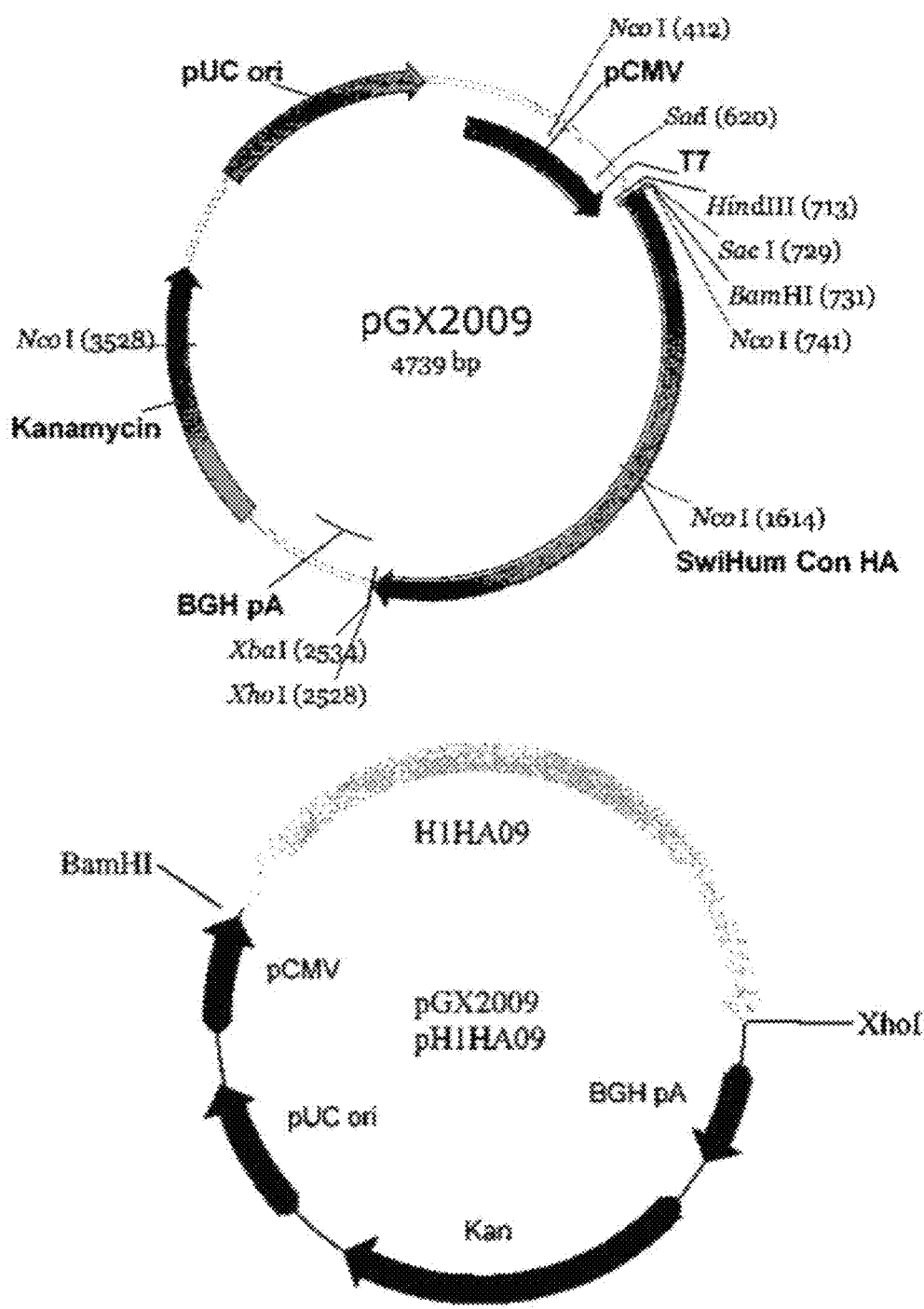
Figure 3:
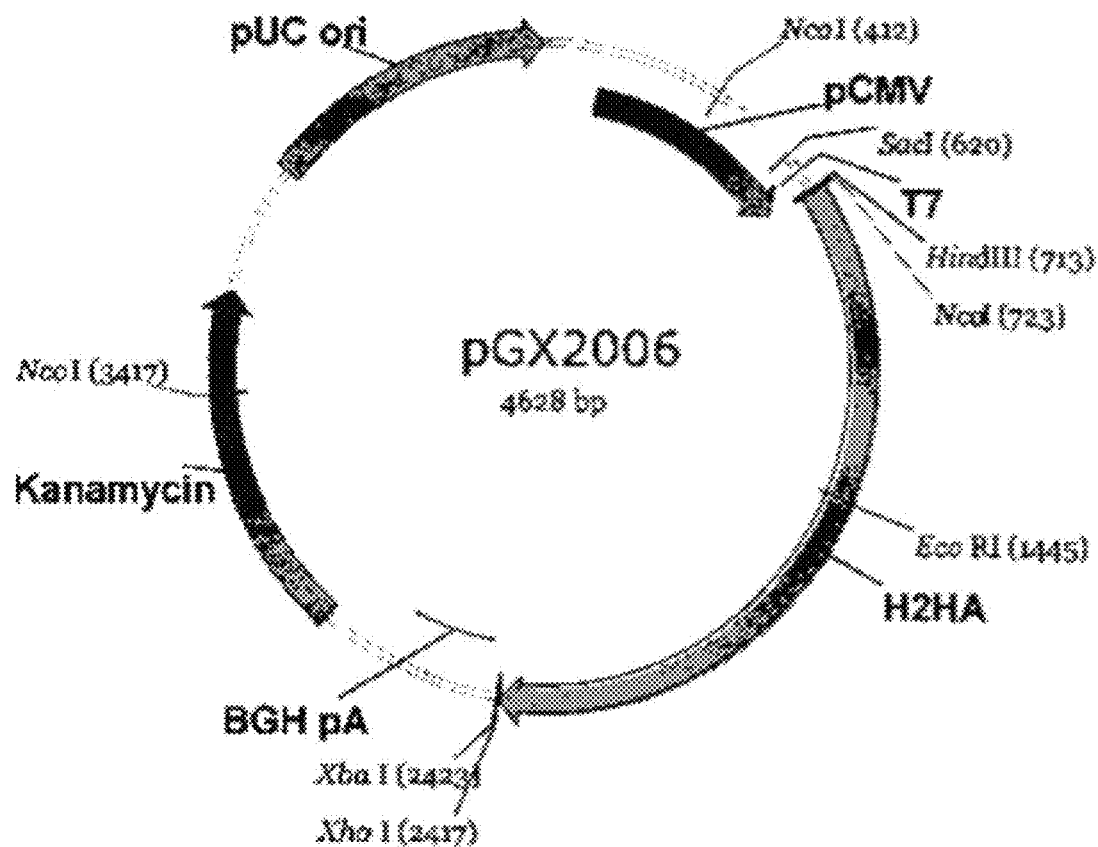

The vector can be pGX2009 or pGX2006, which can be used for expressing the consensus hemagglutinin antigen. The vector pGX2009 (4739 bp, FIG. 2; SEQ ID NO: 5) is a modified pVAX1 plasmid with a nucleic acid sequence that encodes a consensus H1 protein (amino acid SEQ ID NO:4 encoded by SEQ ID NO:3) that comprises an IgE leader sequence (amino acid SEQ ID NO:12 encoded by SEQ ID NO:11) linked to a consensus H1 amino acid sequence (amino acid SEQ ID NO:2 encoded by SEQ ID NO:1). The vector pGX2006 (4628 bp; FIG. 3, SEQ ID NO:8) is a pVAX1 plasmid with a nucleic acid sequence that encodes a consensus H2 protein (amino acid SEQ ID NO:7 encoded by SEQ ID NO:6). Alternatively, in a similar DNA plasmid backbone pVAX1 as pGX2006 (or pVAX (Invitrogen), a nucleic acid insert can replace the H2HA sequence with any one of the following: SEQ ID NO:1, SEQ ID NO:6, SEQ ID NO:9, SEQ ID NO:13, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, or nucleic acid sequences that encode one or more of: SEQ ID NO:2, SEQ ID NO:7, SEQ ID NO:10, SEQ ID NO:14, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38; or any fragments and variants described herein.

The genetic constructs and components disclosed herein which include consensus hemagglutinin coding sequences may be used to express other influenza proteins such as influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin or neuraminidase protein whereby coding sequences for influenza A proteins H1, H2, H3, H4, H5, H6, H7, H8, H9, H10, H11, H12, H13, H14, H15, H16, N1, N2, N3, N4, N5, N6, N7, N8, N9, influenza B hemagglutinin or neuraminidase protein are included in place of consensus hemagglutinin coding sequences.

4. Pharmaceutical Compositions

Provided herein are pharmaceutical compositions according to the present invention which comprise about 1 nanogram to about 10 mg of DNA. In some embodiments, pharmaceutical compositions according to the present invention comprise from between: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg. In some embodiments, pharmaceutical compositions according to the present invention comprise about 5 nanogram to about 10 mg of DNA. In some embodiments, pharmaceutical compositions according to the present invention comprise about 25 nanogram to about 5 mg of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Preferably the pharmaceutical composition is a vaccine, and more preferably a DNA vaccine.

Provided herein is a vaccine capable of generating in a mammal an immune response against one or more influenza serotypes. The vaccine can comprise the genetic construct as discussed above. The vaccine can comprise a plurality of the vectors each directed to one or more Influenza A serotypes such as H1-H16 Influenza B hemagglutinin or combinations thereof. The vaccine may comprise one or more nucleic acid sequences that encode one or more consensus hemagglutinin antigens. When the vaccine comprises more than one consensus hemagglutinin nucleic acid sequences, all such sequences may be present on a single nucleic acid molecule or each such sequences may be present on a different nucleic acid molecule. Alternatively, vaccines that comprise more than one consensus hemagglutinin nucleic acid sequences may comprise nucleic acid molecules with a single consensus hemagglutinin nucleic acid sequences and nucleic acid molecules with more than one consensus hemagglutinin nucleic acid sequences. In addition, vaccines comprising one or more consensus hemagglutinin nucleic acid sequences may further comprise coding sequences for one or more proteins selected from the group consisting of H1, H2, H3, H4, H5, H6, H7, H8, H9, H10, H11, H12, H13, H14, H15, H16, N1, N2, N3, N4, N5, N6, N7, N8, N9 and influenza B neuraminise.

In some embodiments, vaccines may comprise proteins. Some vaccines may comprise one or more consensus hemagglutinin antigens such as H1, H2, U2 and BHA. The vaccines may comprise one or more other proteins selected from the group consisting of H1, H2, H3, H4, H5, H6, H7, H8, H9, H10, H11, H12, H13, H14, H15, H16, N1, N2, N3, N4, N5, N6, N7, N8, N9 and influenza B neuraminidase. The vaccines may comprise one or more consensus hemagglutinin antigens in combination with one or more other proteins selected from the group consisting of H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase.

The vaccine may be a DNA vaccine. The DNA vaccine may comprise a plurality of the same or different plasmids comprising one or more of consensus hemagglutinin nucleic acid sequences. The DNA vaccine may comprise one or more nucleic acid sequences that encode one or more consensus hemagglutinin antigens. When the DNA vaccine comprises more than one consensus hemagglutinin nucleic acid sequences, all such sequences may be present on a single plasmid, or each such sequences may be present on a different plasmids, or some plasmids may comprise a single consensus hemagglutinin nucleic acid sequences while other plasmids have more than one consensus hemagglutinin nucleic acid sequences. In addition, DNA vaccines may further comprise one or more consensus coding sequences for one or more proteins selected from the group consisting of influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase. Such additional coding sequences may be on the same or different plasmids from each other and from the plasmids comprising one or more of consensus hemagglutinin nucleic acid sequences.

In some embodiments, vaccines may comprise nucleic acid sequences that encode influenza antigens in combination with influenza antigens. In some embodiments, the nucleic acid sequences encode one or more consensus hemagglutinin antigens such as H1 (including H1U and H1U2), H2, H3, and BHA. In some embodiments, the nucleic acid sequences encode one or more one or more other proteins selected from the group consisting of, influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase. In some embodiments, the vaccines comprise one or more consensus hemagglutinin antigens such as H1 (including H1U and H1U2), H2, H3, and BHA. In some embodiments, the vaccines comprise one or more one or more other proteins selected from the group consisting of influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase.

In some embodiments, vaccines comprise a combination of three or more consensus hemagglutinin nucleic acid sequences including those encoding one or more of H1 (including H1U and H1U2), H2, and BHA. In some embodiments, vaccines comprise a combination of three or more hemagglutinin nucleic acid sequences including those encoding consensus H1U and/or H1U2, consensus BHA and an H3 hemagglutinin. In some embodiments, vaccines comprise a combination of three or more hemagglutinin nucleic acid sequences including those encoding consensus BHA, an H1 hemagglutinin and an H3 hemagglutinin. In some embodiments, vaccines comprise one or more nucleic acid sequences that encode one or more influenza antigens disclosed in U.S. Ser. No. 12/375,518, which is incorporated herein by reference and/or U.S. Ser. No. 12/269,824, which is incorporated herein by reference. In some embodiments, vaccines comprise a nucleic acid sequence that encodes an H1 hemagglutinin from U.S. Ser. No. 12/375,518 (SEQ ID NO:36 therein) and/or U.S. Ser. No. 12/269,824 (SEQ ID NO:9 therein). In some embodiments, vaccines comprise a nucleic acid sequence that encodes an H3 hemagglutinin from U.S. Ser. No. 12/269,824 (SEQ ID NO:11 therein).

In some embodiments, vaccines comprise a combination of three or more consensus hemagglutinin proteins including one or more of H1, H2, U2 and BHA. In some embodiments, vaccines comprise a combination of three or more hemagglutinin proteins including consensus U2, consensus BHA and an H3 hemagglutinin. In some embodiments, vaccines comprise a combination of three or more hemagglutinin proteins including consensus BHA, an H1 hemagglutinin and an H3 hemagglutinin. In some embodiments, vaccines comprise one or more antigens from U.S. Ser. No. 12/375, 518 and/or U.S. Ser. No. 12/269,824. In some embodiments, vaccines comprise an H1 hemagglutinin disclosed in U.S. Ser. No. 12/375,518 (SEQ ID NO:37 therein) and/or U.S. Ser. No. 12/269,824 (SEQ ID NO:10 therein). In some embodiments, vaccines comprise an H3 hemagglutinin disclosed in U.S. Ser. No. 12/269,824 (SEQ ID NO:12 therein).

In some embodiments, vaccines comprise a combination of 1) the consensus hemagglutinin U2 protein and/or a nucleic acid sequences encoding the consensus hemagglutinin U2 protein, 2) the consensus hemagglutinin BHA protein and/or a nucleic acid sequences encoding the consensus hemagglutinin BHA protein, and 3) a hemagglutinin H3 protein disclosed in U.S. Ser. No. 12/269,824 (SEQ ID NO:12 therein) and/or a nucleic acid sequences encoding hemagglutinin H3 protein disclosed in U.S. Ser. No. 12/269, 824 (SEQ ID NO:11 therein).

In some embodiments, vaccines comprise a combination of 1) the consensus hemagglutinin BHA protein and/or a nucleic acid sequences encoding the consensus hemagglutinin BHA protein, 2) a hemagglutinin H1 protein disclosed in U.S. Ser. No. 12/269,824 (SEQ ID NO:10 therein) or U.S. Ser. No. 12/375,518 (SEQ ID NO:37 therein) and/or a nucleic acid sequences encoding hemagglutinin H1 protein disclosed in U.S. Ser. No. 12/269,824 (SEQ ID NO:9 therein) or U.S. Ser. No. 12/375,518 (SEQ ID NO:36 therein), and 3) a hemagglutinin H3 protein disclosed in U.S. Ser. No. 12/269,824 (SEQ ID NO:12 therein) and/or a nucleic acid sequences encoding hemagglutinin H3 protein disclosed in U.S. Ser. No. 12/269,824 (SEQ ID NO:11 therein).

Preferably, combinations of antigens provided herein can be formulated to a vaccine that causes seroconversion in vaccinated mammals that provide cross-reactivity against a broad range of seasonal strains of influenza and also pandemic strains of influenza. The seroconversion and broad cross-reactivity can be determined by measuring inhibiting titers against different hemagglutinin strains of influenza. Preferred combinations include at least one antigen from the following groups: 1) consensus H1 hemagglutinin; 2) consensus H2 hemagluttinin; 3) consensus H3 hemagglutinin; and 4) influenza B hemagglutinin; and more preferred combinations include at least one antigen from the following groups: 1) consensus H1 hemagglutinin; 2) consensus H3 hemagglutinin; and 3) influenza B hemagglutinin.

In some embodiments the vaccines can have a combination as such:
a) one or more of a first influenza nucleic acid sequence H1 hemagglutinin capable of generating broadly cross reactive immune response in mammals against multiple strains of influenza virus, which is/are selected from the following: a nucleic acid sequence selected from the group consisting of: SEQ ID NO:1, a nucleic acid sequence that is at least 95% homologous to SEQ ID NO:1; a fragment of SEQ ID NO:1; a nucleic acid sequence that is at least 95% homologous to a fragment of SEQ ID NO:1; SEQ ID NO:9, a nucleic acid sequence that is at least 95% homologous to SEQ ID NO:9; a fragment of SEQ ID NO:9; a nucleic acid sequence that is at least 95% homologous to a fragment of SEQ ID NO:9; SEQ ID NO:19; a nucleic acid sequence that is at least 95% homologous to SEQ ID NO:19; a fragment of SEQ ID NO:19; a nucleic acid sequence that is at least 95% homologous to a fragment of SEQ ID NO:19; SEQ ID NO:21; a nucleic acid sequence that is at least 95% homologous to SEQ ID NO:21; a fragment of SEQ ID NO:21; a nucleic acid sequence that is at least 95% homologous to a fragment of SEQ ID NO:21; SEQ ID NO:35; a nucleic acid sequence that is at least 95% homologous to SEQ ID NO:35; a fragment of SEQ ID NO:35; a nucleic acid sequence that is at least 95% homologous to a fragment of SEQ ID NO:35; nucleic acid sequences encoding SEQ ID NO:2, a nucleic acid sequence that is at least 95% homologous to nucleic acid sequences encoding SEQ ID NO:2; a fragment of nucleic acid sequences encoding SEQ ID NO:2; a nucleic acid sequence that is at least 95% homologous to a fragment of nucleic acid sequences encoding SEQ ID NO:2; nucleic acid sequences encoding SEQ ID NO:10, a nucleic acid sequence that is at least 95% homologous to nucleic acid sequences encoding SEQ ID NO:10; a fragment of nucleic acid sequences encoding SEQ ID NO:10; a nucleic acid sequence that is at least 95% homologous to a fragment of nucleic acid sequences encoding SEQ ID NO:10; nucleic acid sequences encoding SEQ ID NO:20; a nucleic acid sequence that is at least 95% homologous to nucleic acid sequences encoding SEQ ID NO:20; a fragment of nucleic acid sequences encoding SEQ ID NO:20; a nucleic acid sequence that is at least 95% homologous to a fragment of nucleic acid sequences encoding SEQ ID NO:20; nucleic acid sequences encoding SEQ ID NO:22; a nucleic acid sequence that is at least 95% homologous to nucleic acid sequences encoding SEQ ID NO:22; a fragment of nucleic acid sequences encoding SEQ ID NO:22; a nucleic acid sequence that is at least 95% homologous to a fragment of nucleic acid sequences encoding SEQ ID NO:22; nucleic acid sequences encoding SEQ ID NO:36; a nucleic acid sequence that is at least 95% homologous to nucleic acid sequences encoding SEQ ID NO:36; a fragment of nucleic acid sequences encoding SEQ ID NO:36; and a nucleic acid sequence that is at least 95% homologous to a fragment of nucleic acid sequences encoding SEQ ID NO:36.

b) one or more of a first influenza nucleic acid sequence H3 hemagglutinin capable of generating broadly cross reactive immune response in mammals against multiple strains of influenza virus, which is/are selected from the following: a nucleic acid sequence selected from the group consisting of: SEQ ID NO:23, a nucleic acid sequence that is at least 95% homologous to SEQ ID NO:23; a fragment of SEQ ID NO:23; a nucleic acid sequence that is at least 95% homologous to a fragment of SEQ ID NO:23; SEQ ID NO:27, a nucleic acid sequence that is at least 95% homologous to SEQ ID NO:27; a fragment of SEQ ID NO:27; a nucleic acid sequence that is at least 95% homologous to a fragment of SEQ ID NO:27; SEQ ID NO:29; a nucleic acid sequence that is at least 95% homologous to SEQ ID NO:29; a fragment of SEQ ID NO:29; a nucleic acid sequence that is at least 95% homologous to a fragment of SEQ ID NO:29; SEQ ID NO:37; a nucleic acid sequence that is at least 95% homologous to SEQ ID NO:37; a fragment of SEQ ID NO:37; a nucleic acid sequence that is at least 95% homologous to a fragment of SEQ ID NO:37; nucleic acid sequences encoding SEQ ID NO:24, a nucleic acid sequence that is at least 95% homologous to nucleic acid sequences encoding SEQ ID NO:24; a fragment of nucleic acid sequences encoding SEQ ID NO:24; a nucleic acid sequence that is at least 95% homologous to a fragment of nucleic acid sequences encoding SEQ ID NO:24; nucleic acid sequences encoding SEQ ID NO:28; a nucleic acid sequence that is at least 95% homologous to nucleic acid sequences encoding SEQ ID NO: 28; a fragment of nucleic acid sequences encoding SEQ ID NO: 28; a nucleic acid sequence that is at least 95% homologous to a fragment of nucleic acid sequences encoding SEQ ID NO: 28; nucleic acid sequences encoding SEQ ID NO:30; a nucleic acid sequence that is at least 95% homologous to nucleic acid sequences encoding SEQ ID NO: 30; a fragment of nucleic acid sequences encoding SEQ ID NO: 30; a nucleic acid sequence that is at least 95% homologous to a fragment of nucleic acid sequences encoding SEQ ID NO: 30; nucleic acid sequences encoding SEQ ID NO:38; a nucleic acid sequence that is at least 95% homologous to nucleic acid sequences encoding SEQ ID NO: 38; a fragment of nucleic acid sequences encoding SEQ ID NO: 38; and a nucleic acid sequence that is at least 95% homologous to a fragment of nucleic acid sequences encoding SEQ ID NO: 38.

c) one or more of a first influenza nucleic acid sequence influenza B hemagglutinin capable of generating broadly cross reactive immune response in mammals against multiple strains of influenza virus, which is/are selected from the following:
a nucleic acid sequence selected from the group consisting of: SEQ ID NO:13, a nucleic acid sequence that is at least 95% homologous to SEQ ID NO: 13; a fragment of SEQ ID NO: 13; a nucleic acid sequence that is at least 95% homologous to a fragment of SEQ ID NO: 13; SEQ ID NO:25, a nucleic acid sequence that is at least 95% homologous to SEQ ID NO: 25; a fragment of SEQ ID NO: 25; a nucleic acid sequence that is at least 95% homologous to a fragment of SEQ ID NO: 25; SEQ ID NO:31; a nucleic acid sequence that is at least 95% homologous to SEQ ID NO: 31; a fragment of SEQ ID NO: 31; a nucleic acid sequence that is at least 95% homologous to a fragment of SEQ ID NO: 31; SEQ ID NO:33; a nucleic acid sequence that is at least 95% homologous to SEQ ID NO: 33; a fragment of SEQ ID NO: 33; a nucleic acid sequence that is at least 95% homologous to a fragment of SEQ ID NO: 33; nucleic acid sequences encoding SEQ ID NO:14, a nucleic acid sequence that is at least 95% homologous to nucleic acid sequences encoding SEQ ID NO: 14; a fragment of nucleic acid sequences encoding SEQ ID NO: 14; a nucleic acid sequence that is at least 95% homologous to a fragment of nucleic acid sequences encoding SEQ ID NO: 14; nucleic acid sequences encoding SEQ ID NO:26; a nucleic acid sequence that is at least 95% homologous to nucleic acid sequences encoding SEQ ID NO: 26; a fragment of nucleic acid sequences encoding SEQ ID NO: 26; a nucleic acid sequence that is at least 95% homologous to a fragment of nucleic acid sequences encoding SEQ ID NO: 26; nucleic acid sequences encoding SEQ ID NO:32; a nucleic acid sequence that is at least 95% homologous to nucleic acid sequences encoding SEQ ID NO: 32; a fragment of nucleic acid sequences encoding SEQ ID NO: 32; a nucleic acid sequence that is at least 95% homologous to a fragment of nucleic acid sequences encoding SEQ ID NO: 32; nucleic acid sequences encoding SEQ ID NO:34; a nucleic acid sequence that is at least 95% homologous to nucleic acid sequences encoding SEQ ID NO: 34; a fragment of nucleic acid sequences encoding SEQ ID NO: 34; and a nucleic acid sequence that is at least 95% homologous to a fragment of nucleic acid sequences encoding SEQ ID NO: 34.

In some embodiments, in addition to a), b), and c), above, the combination can also include one or more of a an influenza nucleic acid sequence H2 hemagglutinin capable of generating broadly cross reactive immune response in mammals against multiple strains of influenza virus, which is/are selected from the following: SEQ ID NO:6, a nucleic acid sequence that is at least 95% homologous to SEQ ID NO: 6; a fragment of SEQ ID NO: 6; a nucleic acid sequence that is at least 95% homologous to a fragment of SEQ ID NO: 6; nucleic acid sequences encoding SEQ ID NO:7; a nucleic acid sequence that is at least 95% homologous to nucleic acid sequences encoding SEQ ID NO: 7; a fragment of nucleic acid sequences encoding SEQ ID NO: 7; and a nucleic acid sequence that is at least 95% homologous to a fragment of nucleic acid sequences encoding SEQ ID NO: 7.

DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome. The vaccine can be an RNA of the hemagglutinin antigen. The RNA vaccine can be introduced into the cell.

The vaccine can be a recombinant vaccine comprising the genetic construct or antigen described above. The vaccine can also comprise one or more consensus hemagglutinin antigen in the form of one or more protein subunits, one or more killed influenza particles comprising one or more consensus hemagglutinin antigens, or one or more attenuated influenza particles comprising one or more consensus hemagglutinin antigens. The attenuated vaccine can be attenuated live vaccines, killed vaccines and vaccines that use recombinant vectors to deliver foreign genes that encode one or more consensus hemagglutinin antigens, and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine can comprise vectors and/or proteins directed to Influenza A serotypes from particular regions in the world, for example, Asia. The vaccine can also be directed against Influenza A serotypes of swine origin that now infect humans. The vaccine can comprise vectors and/or proteins directed to Influenza B from particular regions in the world. The vaccine can also be directed against Influenza B that infect humans. The vaccine can comprise one or more vectors and/or one or more proteins directed to one or more strains of Influenza A and/or B.

The vaccine provided may be used to induce immune responses including therapeutic or prophylactic immune responses. Antibodies and/or killer T cells may be generated which are directed to the consensus hemagglutinin antigen, and also broadly across multiple subtypes of influenza viruses. Such antibodies and cells may be isolated.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine can further comprise a genetic vaccine facilitator agent as described in U.S. Serial No. 021,579 filed Apr. 1, 1994, which is fully incorporated by reference.

5. Methods of Delivery

Provided herein is a method for delivering the pharmaceutical formulations, preferably vaccines, for providing genetic constructs and proteins of the hemagglutinin antigen which comprise epitopes that make them particular effective immunogens against which an immune response to influenza viral infections can be induced. The method of delivering the vaccine, or vaccination, can be provided to induce a therapeutic and/or prophylactic immune response. The vaccination process can generate in the mammal an immune response against a plurality of influenza subtypes, including a H1N1 serotype, such as the 2009 swine originated H1N1, or other seasonal and/or pandemic varieties. The vaccine can be delivered to an individual to modulate the activity of the mammal's immune system and enhance the immune response. The delivery of the vaccine can be the transfection of the HA antigen as a nucleic acid molecule that is expressed in the cell and delivered to the surface of the cell upon which the immune system recognized and induces a cellular, humoral, or cellular and humoral response. The delivery of the vaccine can be use to induce or elicit and immune response in mammals against a plurality of influenza viruses by administering to the mammals the vaccine as discussed herein.

Upon delivery of the vaccine to the mammal, and thereupon the vector into the cells of the mammal, the transfected cells will express and secrete the corresponding influenza protein, including at least one of the consensus antigens, and preferably H1, H2, U2, and BHA. These secreted proteins, or synthetic antigens, will be recognized as foreign by the immune system, which will mount an immune response that can include: antibodies made against the antigens, and T-cell response specifically against the antigen. In some examples, a mammal vaccinated with the vaccines discussed herein will have a primed immune system and when challenged with an influenza viral strain, the primed immune system will allow for rapid clearing of subsequent influenza viruses, whether through the humoral, cellular, or both. The vaccine can be delivered to an individual to modulate the activity of the individual's immune system thereby enhancing the immune response.

The vaccine can be delivered in the form of a DNA vaccine and methods of delivering a DNA vaccines are described in U.S. Pat. Nos. 4,945,050 and 5,036,006, which are both incorporated fully by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

a. Combination with Other Antigens and Adjuvants

The pharmaceutical compositions, preferably vaccines, described herein can be administered in combination with one or more other influenza proteins or genes encoding influenza A H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase. The vaccine can be administered in combination with proteins or genes encoding adjuvants, which can include: α-interferon (IFN-α), β-interferon (IFN-β), γ-interferon, IL-12, IL-15, IL-21, IL-23, IL-28, IL-33, CTACK, TECK, platelet derived growth factor (PDGF), TNFα, TNFβ, GM-CSF, epidermal growth factor (EGF), IL-1, IL-2, IL-4, IL-5, IL-6, IL-10, IL-18, MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, or TAP2, or functional fragments thereof.

b. Routes of Administration

The vaccine can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns", or other physical methods such as electroporation ("EP"), "hydrodynamic method", or ultrasound.

The vector of the vaccine can be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The HA antigen can be delivered via DNA injection and along with in vivo electroporation.

c. Electroporation

Administration of the vaccine via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA® EP system (VGX Pharmaceuticals, Blue Bell, Pa.) or Elgen electroporator (Genetronics, San Diego, Calif.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

d. Method of Preparing Vaccine

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1 pGX2009 (pH1HA09)—Plasmid Encoding 2009 H1N1 Influenza (Swine Flu) Hemagglutinin Antigen The backbone of pGX2009 (H1HA09) is the modified expression vector pVAX1 (Invitrogen, Carlsbad, Calif.) under the control of the cytomegalovirus immediate-early (CMV) promoter. The original pVAX1 was purchased from Invitrogen (Catalog number V260-20) and maintained at −20° C. As noted above, sequence analysis revealed differences between the sequence of pVAX1 used as the backbone of pGX2009 and the pVAX1 sequence available from Invitrogen. The differences are set forth above.

Plasmid pGX2009, also referred to as pH1HA09, comprises a nucleic acid sequence that encodes a consensus 2009 H1N1 influenza (swine flu) hemagglutinin molecule. The 79 primary sequences used to generate the consensus sequence were selected from The Influenza Sequence Database.

The accession numbers for nucleotide sequences encoding the amino acid sequence for the various influenza A hemagglutinin H1 proteins as well as the amino acid sequences encoded by the nucleotide sequences are in the GenBank database corresponding to the following accession numbers. The accession numbers not in parentheses disclose nucleotide sequences and additional list amino acid sequences encoded by them. The accession numbers in parentheses are for entries of the corresponding amino acid sequence in GenBank's protein database.

The accession numbers are as follows: GQ323579.1 (ACS72657.1), GQ323564.1 (ACS72654.1), GQ323551.1 (ACS72652.1), GQ323530.1 (ACS72651.1), GQ323520.1 (ACS72650.1), GQ323495.1 (ACS72648.1), GQ323489.1 (ACS72647.1), GQ323486.1 (ACS72646.1), GQ323483.1 (ACS72645.1), GQ323455.1 (ACS72641.1), GQ323451.1 (ACS72640.1), GQ323443.1 (ACS72638.1), GQ293077.1 (ACS68822.1), GQ288372.1 (ACS54301.1), GQ287625.1 (ACS54262.1), GQ287627.1 (ACS54263.1), GQ287623.1 (ACS54261.1), GQ287621.1 (ACS54260.1), GQ286175.1 (ACS54258.1), GQ283488.1 (ACS50088.1), GQ280797.1 (ACS45035.1), GQ280624.1 (ACS45017.1), GQ280121.1 (ACS45189.1), GQ261277.1 (ACS34968.1), GQ253498.1 (ACS27787.1), GQ323470.1 (ACS72643.1), GQ253492.1 (ACS27780.1), FJ981613.1 (ACQ55359.1), FJ971076.1 (ACP52565.1), FJ969540.1 (ACP44189.1), FJ969511.1 (ACP44150.1), FJ969509.1 (ACP44147.1), GQ255900.1 (ACS27774.1), GQ255901.1 (ACS27775.1), FJ966974.1 (ACP41953.1), GQ261275.1 (ACS34967.1), FJ966960.1 (ACP41935.1), FJ966952.1 (ACP41926.1), FJ966082.1 (ACP41105.1), GQ255897.1 (ACS27770.1), CY041645.1 (ACS27249.1), CY041637.1 (ACS27239.1), CY041629 (ACS27229.1), GQ323446.1 (ACS72639.1), CY041597.1 (ACS27189.1), CY041581.1 (ACS14726.1), CY040653.1 (ACS14666.1), CY041573.1 (ACS14716.1), CY041565.1 (ACS14706.1), CY041541.1 (ACS14676.1), GQ258462.1 (ACS34667.1), CY041557.1 (ACS14696.1), CY041549.1 (ACS14686.1), GQ283484.1 (ACS50084.1), GQ283493.1 (ACS50095.1), GQ303340.1 (ACS71656.1), GQ287619.1 (ACS54259.1), GQ267839.1 (ACS36632.1), GQ268003.1 (ACS36645.1), CY041621.1 (ACS27219.1), CY041613.1 (ACS27209.1), CY041605.1 (ACS27199.1), FJ966959.1 (ACP41934.1), FJ966982.1 (ACP41963.1), CY039527.2 (ACQ45338.1), FJ981612.1 (ACQ55358.1), FJ981615.1 (ACQ55361.1), FJ982430.1 (ACQ59195.1), FJ998208.1 (ACQ73386.1), GQ259909.1 (ACS34705.1), GQ261272.1 (ACS34966.1), GQ287621.1 (ACS54260.1), GQ290059.1 (ACS66821.1), GQ323464.1 (ACS72642.1), GQ323473.1 (ACS72644.1), GQ323509.1 (ACS72649.1), GQ323560.1 (ACS72653.1), GQ323574.1 (ACS72655.1), and GQ323576.1 (ACS72656.1). The amino acid sequences were downloaded from the NCBI Sequence Database, and an alignment and consensus sequence generated using Clustal X. A highly efficient leader sequence, the IgE leader, was fused in frame upstream of the start codon to facilitate the expression. In order to have a higher level of expression, the codon usage of this fusion gene was adapted to the codon bias of *Homo Sapiens* genes. In addition, RNA optimization was also performed: regions of very high (>80%) or very low (<30%) GC content and the cis-acting sequence motifs such as internal TATA boxes, chi-sites and ribosomal entry sites were avoided. The entire sequence was synthetically produced at Geneart (Regensburg, Germany). The synthetic engineered H1HA09 gene was 1818 bp in length (SEQ ID NO:3 and was cloned into pVAX1 at BamHI and XhoI sites by Geneart (FIG. 2).

Example 2

HS09 Influenza (pGX2009) Immunized Ferrets

Experiments were carried out using ferrets, a preferred model for influenza. The ferrets were immunized using plasmid pGX2009 (SEQ ID NO:5, including insert HS09 (SEQ ID NO:1)).

Animals: 4 groups×5 animals/group, plus one control group with 4 animals=24 ferrets total (male)

Duration: 18 weeks (including challenge)

Dose: 0.2 mg plasmid

Protocol Summary: Ferrets were allocated randomly into DNA vaccine groups.

Animals were immunized at Study Day 0, Day 28, and Day 56. Animals were anesthetized with ketamine/midazolam cocktail, isoflurane or equivalent according to approved anesthesia protocols and vaccinated IM with influenza DNA vaccine combinations. Groups 1 and 2 were immediately electroporated using CELLECTRA® adaptive constant current electroporation (EP) device at 0.5 Amp, 52 millisecond pulses, 0.2 sec between pulses, 4 sec firing delay, 3 total pulses. Control animals were naïve controls (no plasmid, no EP). Ferrets were allowed to recover from anesthesia in their cages and were closely monitored for 24 hours to ensure full recovery.

Food and water was available ad libitum for the length of the study. On Day 84, animals were challenged by intranasal infection with 1 ml of MX10 (A/Mexico/InDRE4487/2009; 5×105 PFU/ml). Animals were monitored daily for clinical signs (weight, temperature, etc.), using an established and approved scoring sheet. On 1, 3, 6, 9 and 15 dpi nasal washes and rectal swabs were collected. Lungs were collected at day 15. Samples were stored in RNAlater for virus load by real-time PCR, medium for infectious virus (TCDI50) and formalin for histology when appropriated.

HAI Titers

Figure 4:
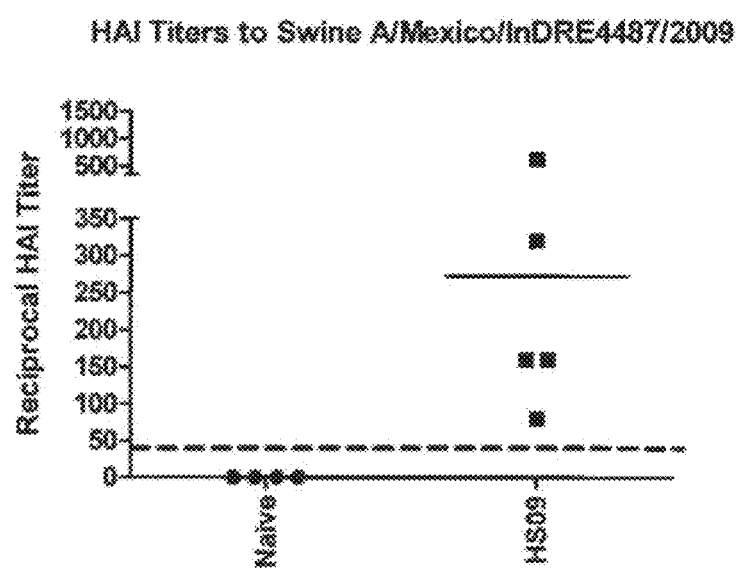

The ferrets were bled and sera samples immediately stored on dry-ice before being shipped to BIOQUAL, Rockville, Md. for processing. Sera was treated with receptor-destroying enzyme by diluting 1 part serum with 3 parts enzyme and were incubated overnight at 37° C. water bath. The enzyme was inactivated by 30-min incubation at 56° C., followed by the addition of 6 parts phosphate-buffered saline for a final dilution of 1/10. HAI assays were performed in V-bottomed 96-well microtiter plates, using 4 hemagglutination units of virus and 1% red blood cells. Virus (H1N1/Mexico/InDRE4487/2009 strain) used for the HAI assays are obtained from the influenza branch of the CDC. FIG. 4 shows a Hemagglutination Inhibition assay performed with sera from immunized ferrets (3 immunizations). A titer of >1:40 is considered "protective". A dotted line indicates the 1:40 mark. All animals were above the 1:40 mark after 3 immunizations.

Challenge Studies

Figure 5:
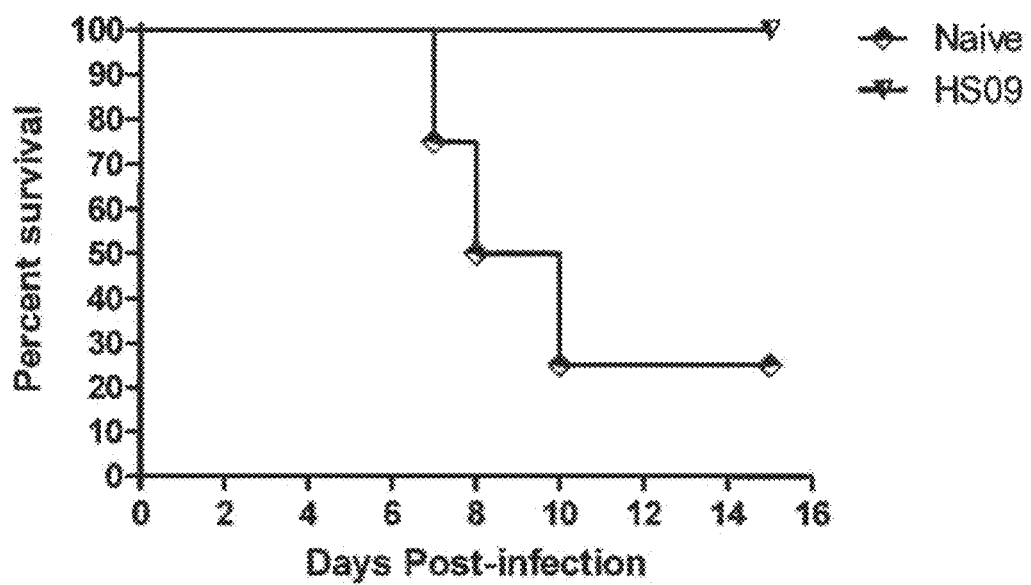
Figure 9A:
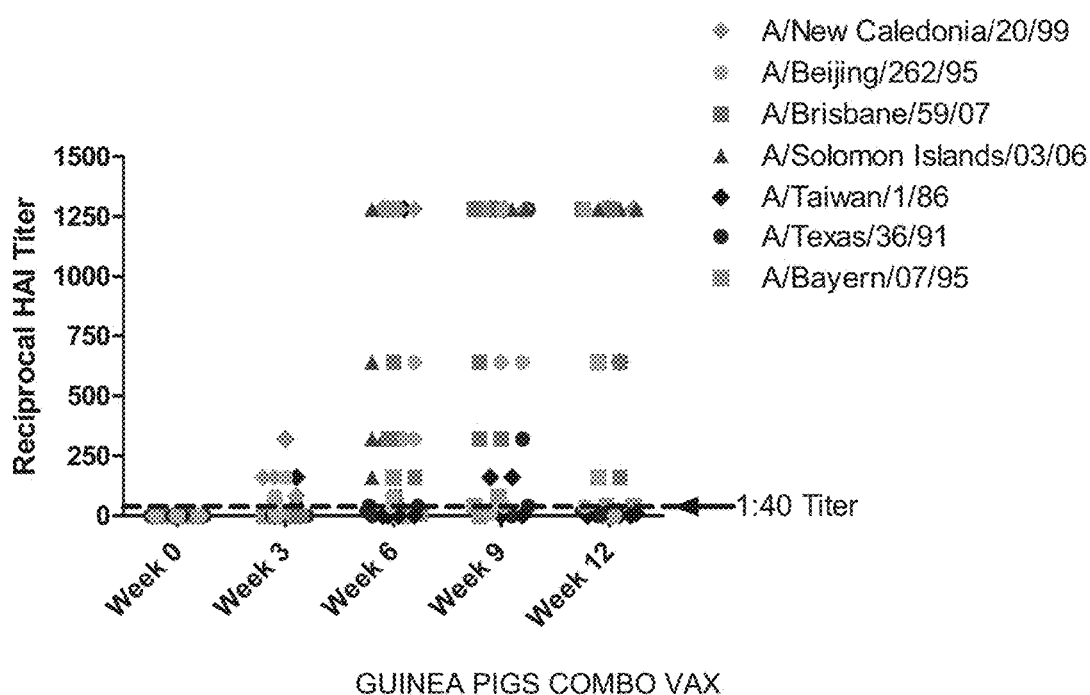
Figure 9B:
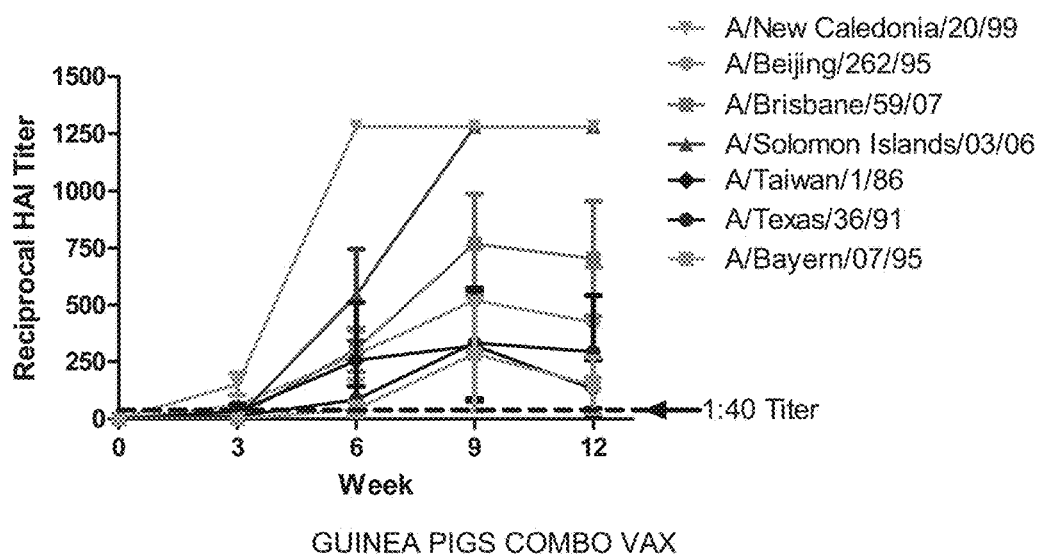
Figure 10A:
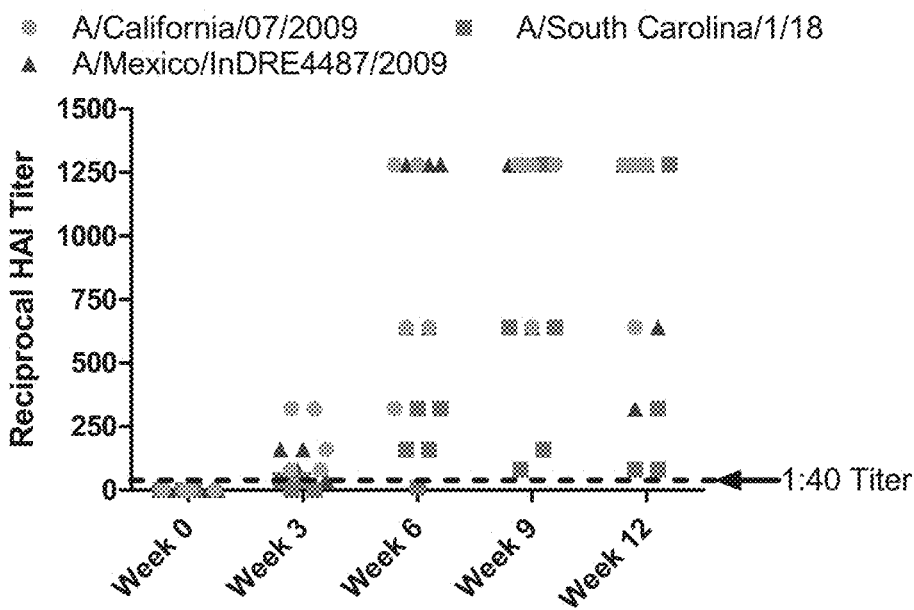
Figure 10B:
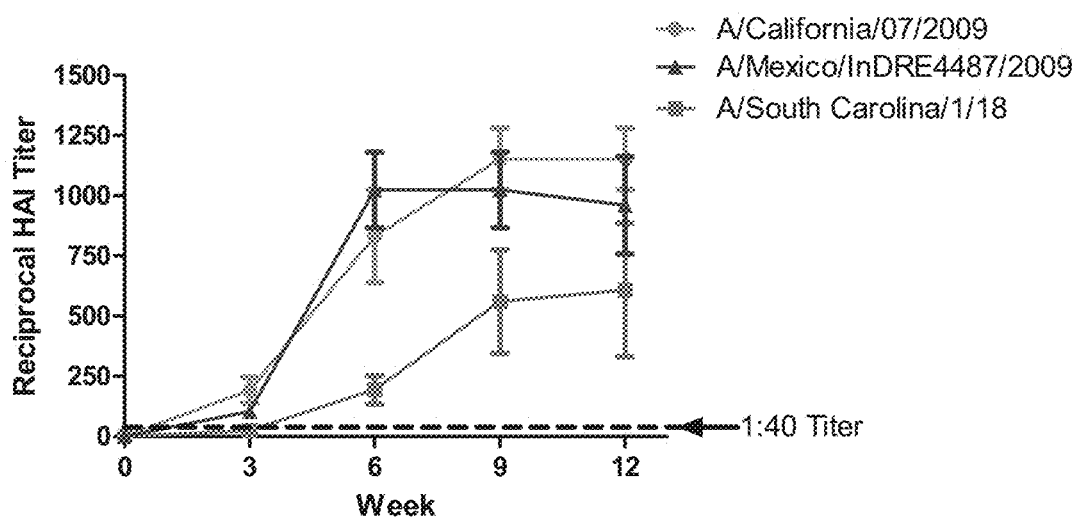
Figure 13:
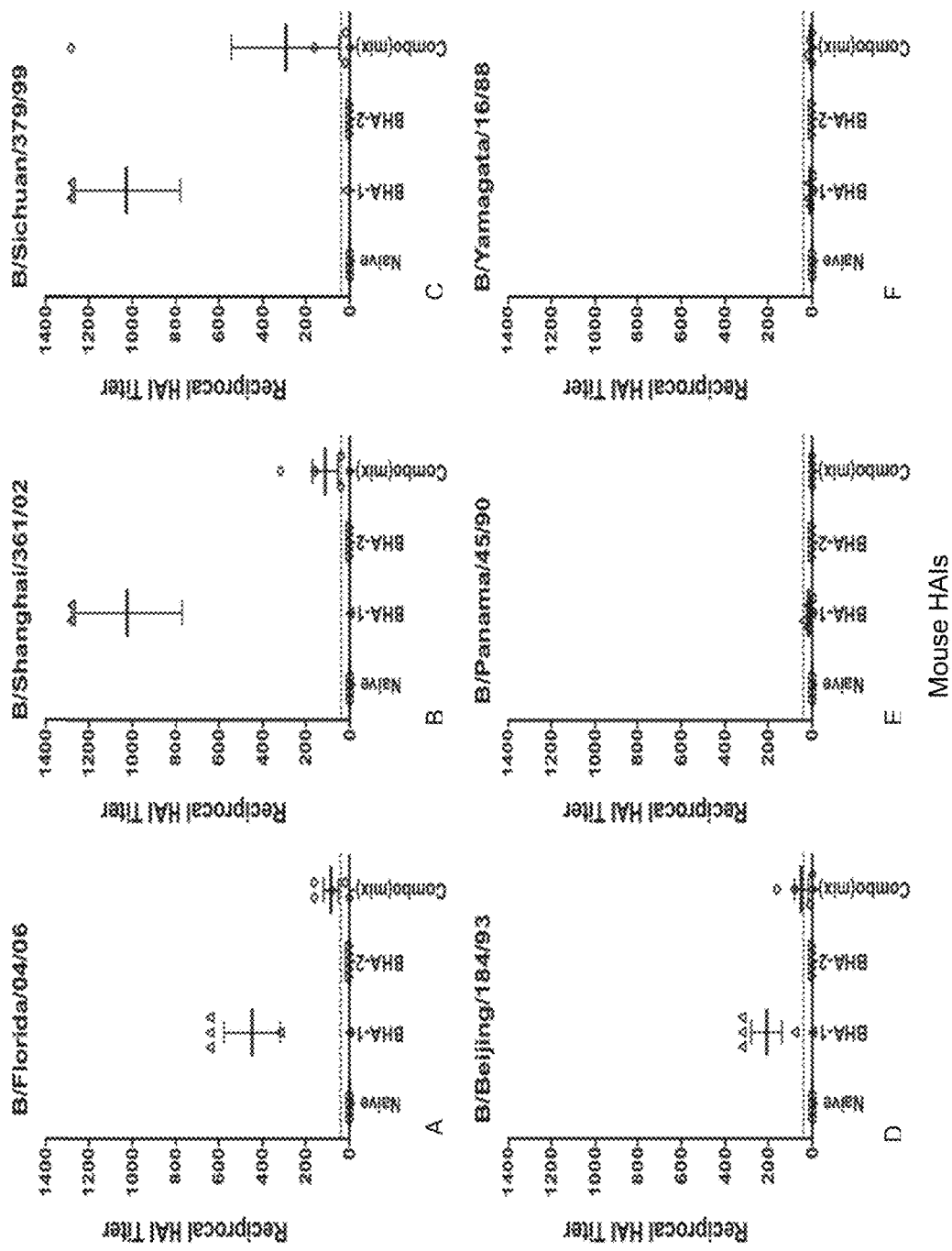
Figure 14:
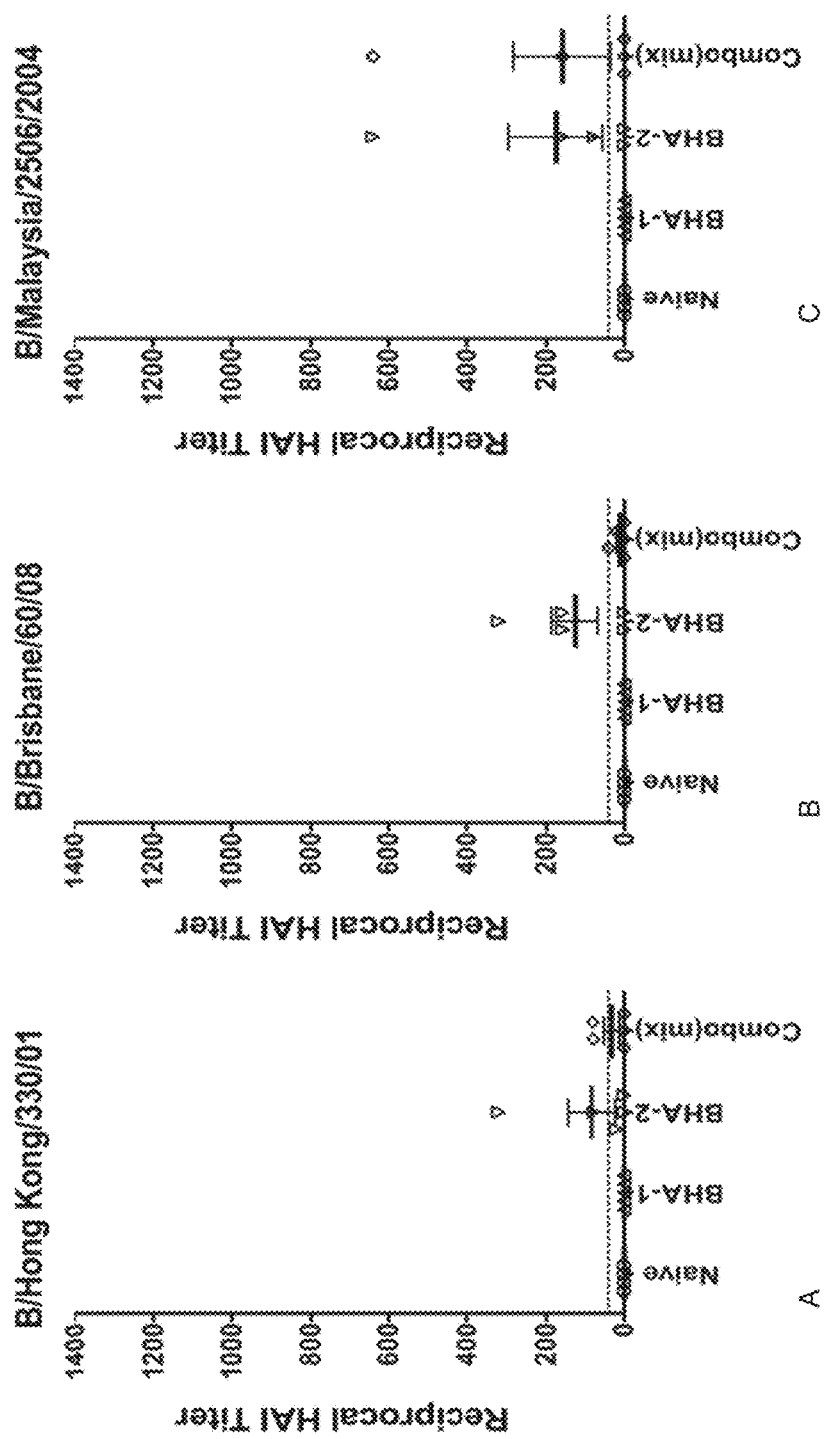
Figure 15:
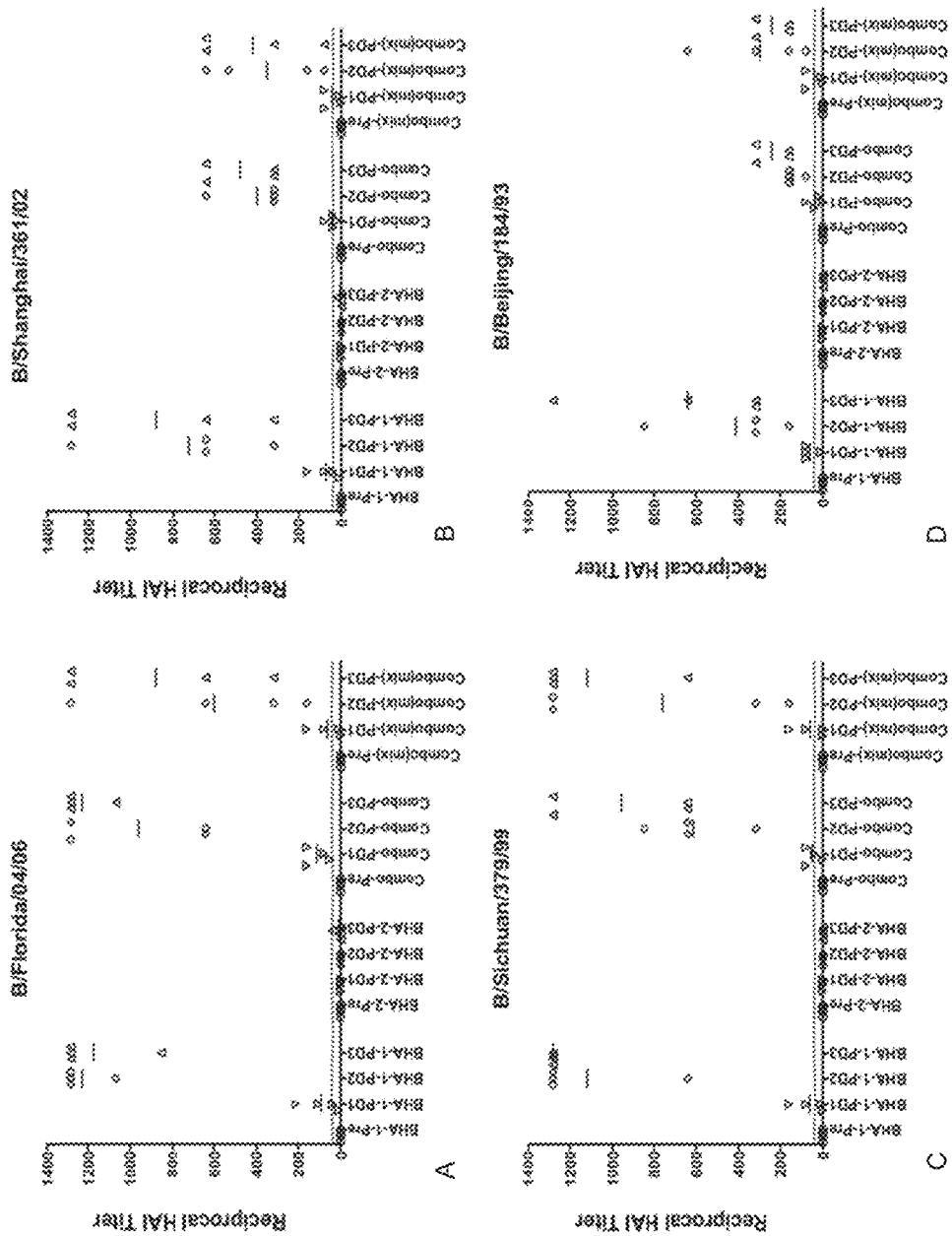
Figure 16:
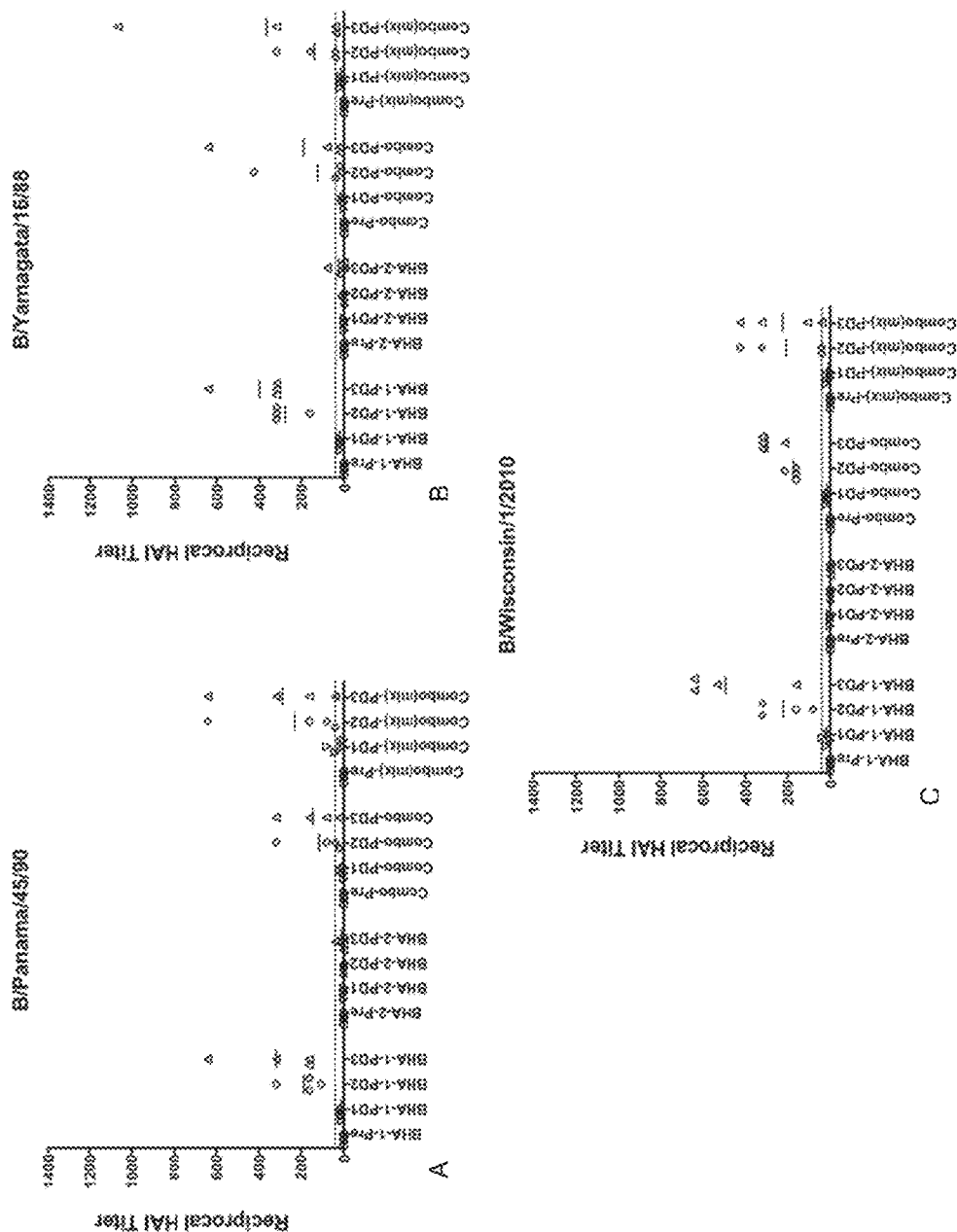
Figure 17:
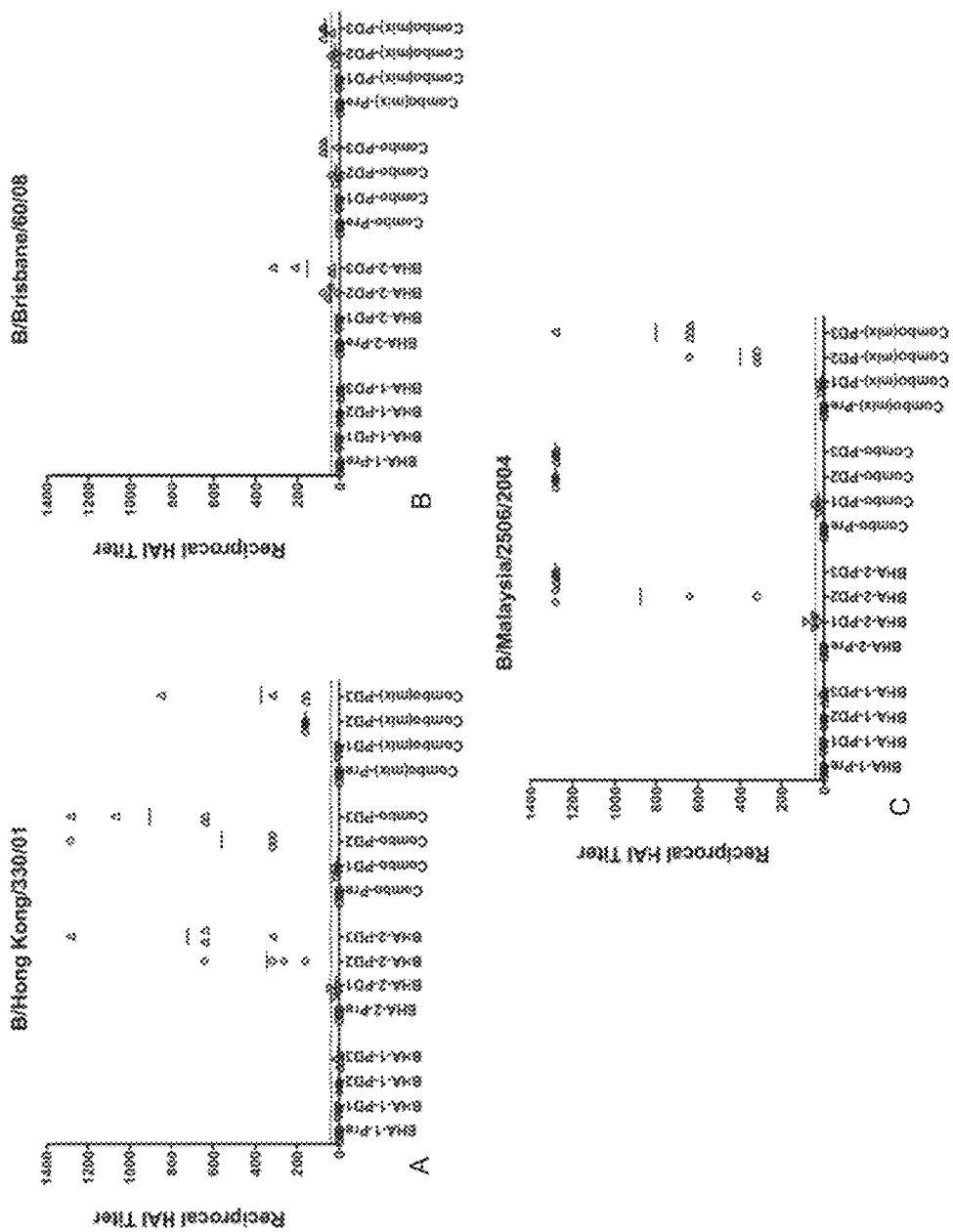

FIG. 5 shows results of a challenge of immunized and unimmunized ferrets with a novel H1N1 strain MX10 (A/Mexico/InDRE4487/2009). All immunized ferrets survived, while 75% of the naive ferrets died within the 15 day period.

Example 3

H1 Hemagglutin Combination Studies

Experiments were carried out using various animals (mouse, guinea pigs and ferrets). The animals were immunized using plasmid constructs with backbone pVAX1, with each construct having a different insert:

In FIGS. 7A-G, 8A-C, 9A-B, 10A-B, 11A-C: naive (pVAX1 only); H1U1 (pVAX1 with SEQ ID NO:35 insert); HS09 (SEQ ID NO:5); ConBris (or H1Bris) (pVAX1 with SEQ ID NO:19 insert); ConTT (or H1TT) (pVAX1 with SEQ ID NO:21 insert);

In FIGS. 13A-F, 14A-C, 15A-D, 16A-C, 17A-C: naive (pVAX1 only); BHA-1 (pVAX1 with SEQ ID NO:13 insert); BHA-2 (pVAX1 with SEQ ID NO:25 insert); BHA-3 (pVAX1 with SEQ ID NO:31 insert); BHA-4 (pVAX1 with SEQ ID NO:33 insert).

In FIGS. 19A-E, 20A-F: naive (pVAX1 only); H3HA-1 (pVAX1 with SEQ ID NO:37 insert); H3HA-2 (pVAX1 with SEQ ID NO:23 insert); H3HA-3 (pVAX1 with SEQ ID NO:27 insert); H3HA-4 (pVAX1 with SEQ ID NO:29 insert).

Dose: 0.2 mg Plasmid

Protocol Summary: animals were allocated randomly into DNA vaccine groups. Animals were immunized at Study Day 0, Day 28, and Day 56. Animals were anesthetized with ketamine/midazolam cocktail, isoflurane or equivalent according to approved anesthesia protocols and vaccinated IM with influenza DNA vaccine combinations. Groups 1 and 2 were immediately electroporated using CELLECTRA adaptive constant current electroporation (EP) device (Inovio Pharmaceuticals, Blue Bell, Pa.) at 0.5 Amp, 52 millisecond pulses, 0.2 sec between pulses, 4 sec firing delay, 3 total pulses. Control animals were naïve controls (no plasmid, no EP). The animals were allowed to recover from anesthesia in their cages and were closely monitored for 24 hours to ensure full recovery.

HAI Assays

Animals were bled and sera samples immediately stored on dry-ice before being shipped to BIOQUAL, Rockville, Md. for processing. Sera was treated with receptor-destroying enzyme by diluting 1 part serum with 3 parts enzyme and were incubated overnight at 37° C. water bath. The enzyme was inactivated by 30-min incubation at 56° C., followed by the addition of 6 parts phosphate-buffered saline for a final dilution of 1/10. HAI assays were performed in V-bottomed 96-well microtiter plates, using 4 hemagglutination units of virus and 1% red blood cells. Virus (H1N1/Mexico/2009 strain) used for the HAI assays are obtained from the influenza branch of the CDC.

H1 Studies:

The experiments showed that mice vaccinated with the combo (all four H1 antigens) showed protective titers against 9 out of 10 strains (FIG. 7A-7F, and FIG. 8A-C). This shows robust cross-reactivity across strains. Similarly the experiments showed that guinea pigs with the combo showed protective titers against all 10 strains (see FIGS. 9A-B and 10A-B).

Flu B Studies:

The experiments showed that mice vaccinated with the combo (both BHA-1 and BHA-2 antigens) showed protective titers against 4 out of 9 strains (FIG. 13A-13C, and FIG. 14C); while 2 strains showed borderline 1:40 (FIG. 13D and FIG. 14A). The individual antigens showed protective titers against 4 of 9 strains (BHA-1) and 3 out of 9 strains (BHA-2). Similarly the experiments showed that guinea pigs with the combo showed protective titers against all 10 strains (see FIGS. 9A-B and 10A-B).

The experiments showed that guinea pigs vaccinated with the combo (both BHA-1 and BHA-2 antigens) showed protective titers against all 10 of 10 strains (looking at post-dose 3 "PD3"). Whereas, on the other hand, immunization with single antigens did not provide such cross-protection, with BHA-1 providing only protective titers against 7 of 10 strains (FIG. 15A-D and FIG. 16A-C).

H3 Studies:

The experiments showed that mice vaccinated with the combo (both H3HA-1 and H3HA-2 antigens) showed protective titers against 4 of 11 strains (FIG. 19A-D), and near protective titers against 2 strains (FIG. 19E and FIG. 20F). Whereas, on the other hand, the single antigens display cross-protection against 4 of 11 strains in the case of H3HA-1 (FIG. 19A-D) but no HAI titer exhibited in any of the remaining strains. The combo H3 mix showed slightly broader cross-protection than one H3 antigen alone.

Challenge Studies

Food and water was available ad libitum for the length of the study. On Day 84, ferrets were challenged by intranasal infection with 1 ml of MX10 (A/Mexico/2009; 5×105 PFU/ml). Animals were monitored daily for clinical signs (weight, temperature, etc.), using an established and approved scoring sheet. On 1, 3, 6, 9 and 15 dpi nasal washes and rectal swabs were collected. Lungs were collected at day 15. Samples were stored in RNAlater for virus load by real-time PCR, medium for infectious virus (TCDI50) and formalin for histology when appropriated.

H1HA Vaccinated—Challenge

Figure 11A:
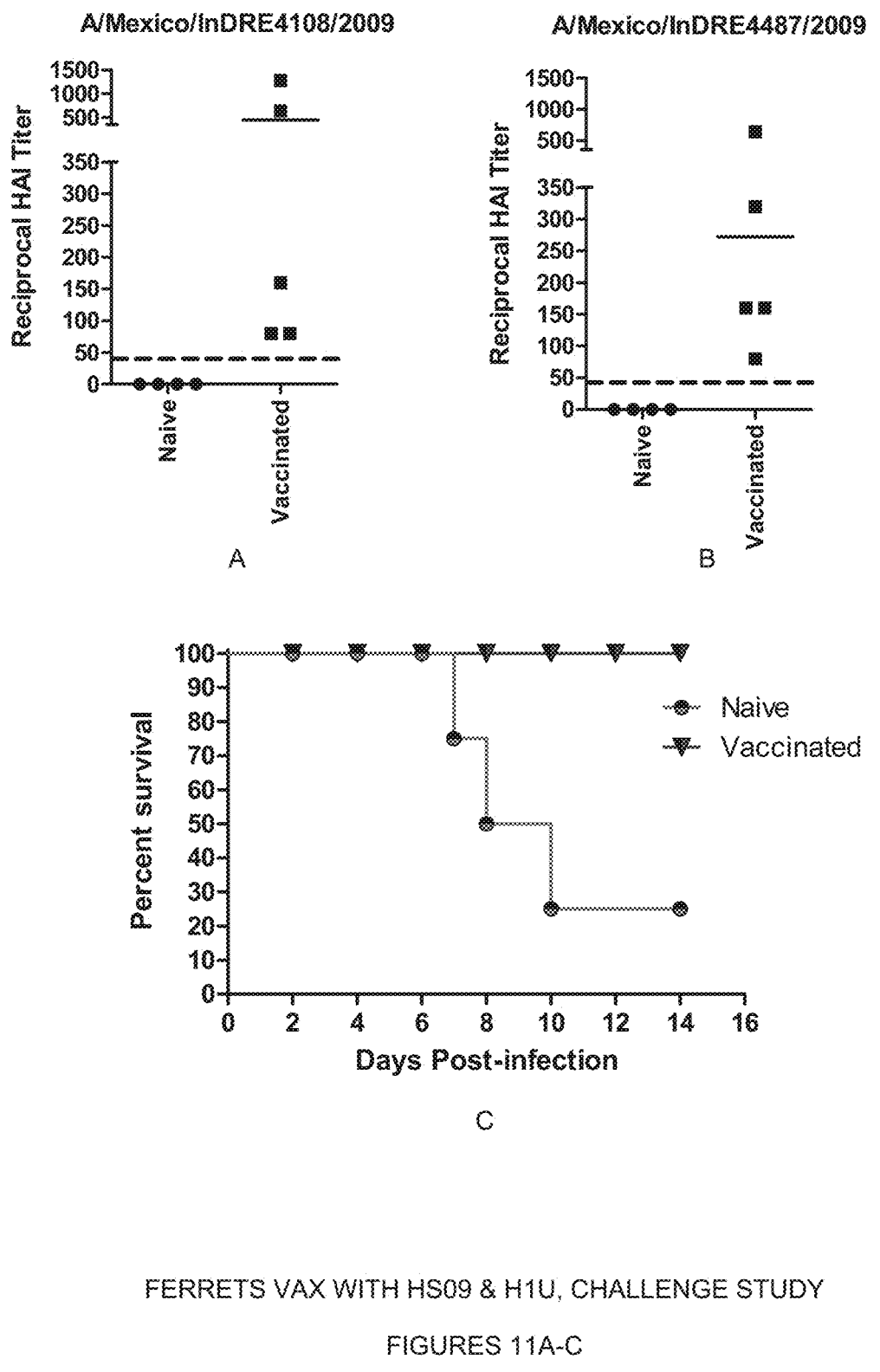

The ferrets vaccinated with HS09 and H1U showed immunoprotection as all five ferrets survive 14 days post-infection; whereas only one out of five naive survived. See FIGS. 11A-C.

What is claimed is:

1. A multiple consensus subtype vaccine wherein the vaccine provides cross-reactivity against a variety of influenza strains, the vaccine comprising at least one consensus nucleic acid sequence encoding a hemagglutinin antigen, wherein said nucleic acid sequence is selected from the group consisting of:
   SEQ ID NO:19 (H1Bris), a nucleic acid sequence that is at least 95% homologous to SEQ ID NO:19, a fragment of SEQ ID NO:19 that is 300 or more nucleotides in length, a nucleic acid sequence that is at least 98% homologous to a fragment of SEQ ID NO:19 that is 300 or more nucleotides in length;
   SEQ ID NO:21 (H1TT), a nucleic acid sequence that is at least 95% homologous to SEQ ID NO:21, a fragment of SEQ ID NO:21 that is 300 or more nucleotides in length, a nucleic acid sequence that is at least 98% homologous to a fragment of SEQ ID NO:21 that is 300 or more nucleotides in length;
   SEQ ID NO:23 (H3HA-2), a nucleic acid sequence that is at least 95% homologous to SEQ ID NO:23, a fragment of SEQ ID NO:23 that is 300 or more nucleotides in length, a nucleic acid sequence that is at least 98% homologous to a fragment of SEQ ID NO:23 that is 300 or more nucleotides in length;
   SEQ ID NO:25 (BHA-2), a nucleic acid sequence that is at least 95% homologous to SEQ ID NO:25, a fragment of SEQ ID NO:25 that is 300 or more nucleotides in length, a nucleic acid sequence that is at least 98% homologous to a fragment of SEQ ID NO:25 that is 300 or more nucleotides in length;
   SEQ ID NO:27 (H3HA-3), a nucleic acid sequence that is at least 95% homologous to SEQ ID NO:27, a fragment of SEQ ID NO:27 that is 300 or more nucleotides in length, a nucleic acid sequence that is at least 98% homologous to a fragment of SEQ ID NO:27 that is 300 or more nucleotides in length;
   SEQ ID NO:29 (H3HA-4), a nucleic acid sequence that is at least 95% homologous to SEQ ID NO:29, a fragment of SEQ ID NO:29 that is 300 or more nucleotides in length, a nucleic acid sequence that is at least 98% homologous to a fragment of SEQ ID NO:29 that is 300 or more nucleotides in length;
   SEQ ID NO:31 (BHA-3), a nucleic acid sequence that is at least 95% homologous to SEQ ID NO:31, a fragment of SEQ ID NO:31 that is 300 or more nucleotides in length, a nucleic acid sequence that is at least 98% homologous to a fragment of SEQ ID NO:31 that is 300 or more nucleotides in length;
   SEQ ID NO:33 (BHA-4), a nucleic acid sequence that is at least 95% homologous to SEQ ID NO:33, a fragment of SEQ ID NO:33 that is 300 or more nucleotides in length, a nucleic acid sequence that is at least 98% homologous to a fragment of SEQ ID NO:33 that is 300 or more nucleotides in length, and any combination thereof.

2. The vaccine of claim 1, further comprising an additional nucleic acid sequence encoding an hemagglutinin antigen selected from the group consisting of H1 hemagglutinin, H2 hemagglutinin, H3 hemagglutinin, and influenza B hemagglutinin, and any combination thereof.

3. The vaccine of claim 2, wherein said additional nucleic acid sequence encoding H1 hemagglutinin is selected from the group consisting of a nucleic acid sequence encoding HS09, a nucleic acid sequence encoding H1U, and any combination thereof.

4. The vaccine of claim 2, wherein the H3 hemagglutinin is selected from the group consisting of H3HA-1, H3HA-2, and any combination thereof.

5. The vaccine of claim 2, wherein the influenza B hemagglutinin is selected from the group consisting of BHA-1, BHA-2, and any combination thereof.

6. The vaccine of claim 3, wherein said nucleic acid sequence encoding HS09 comprises a nucleic acid sequence selected from the group consisting of a nucleic acid sequence encoding SEQ ID NO:2, a nucleic acid sequence that is at least 95% homologous to nucleic acid sequences encoding SEQ ID NO:2; a fragment of nucleic acid sequences encoding SEQ ID NO:2; and a nucleic acid sequence that is at least 95% homologous to a fragment of nucleic acid sequences encoding SEQ ID NO:2;

wherein said nucleic acid sequence encoding H1U comprises a nucleic acid sequence selected from the group consisting of a nucleic acid sequence encoding SEQ ID NO:36, a nucleic acid sequence that is at least 95% homologous to nucleic acid sequences encoding SEQ ID NO:36; a fragment of nucleic acid sequences encoding SEQ ID NO:36; and a nucleic acid sequence that is at least 95% homologous to a fragment of nucleic acid sequences encoding SEQ ID NO:36.

7. The vaccine of claim 3, wherein said nucleic acid sequence encoding H509 comprises a nucleic acid sequence selected from the group consisting of SEQ ID NO:1, a nucleic acid sequence that is at least 95% homologous to SEQ ID NO:1; a fragment of SEQ ID NO:1; and a nucleic acid sequence that is at least 95% homologous to a fragment of SEQ ID NO:1;

wherein said nucleic acid sequence encoding H1U comprises a nucleic acid sequence selected from the group consisting of SEQ ID NO:35, a nucleic acid sequence that is at least 95% homologous to SEQ ID NO:35; a fragment of SEQ ID NO:35; and a nucleic acid sequence that is at least 95% homologous to a fragment of SEQ ID NO:35.

8. The vaccine of claim 4, wherein H3HA-1 comprises a nucleic acid sequence selected from the group consisting of a nucleic acid sequence encoding SEQ ID NO:38, a nucleic acid sequence that is at least 95% homologous to nucleic acid sequences encoding SEQ ID NO:38; a fragment of nucleic acid sequences encoding SEQ ID N0:38; and a nucleic acid sequence that is at least 95% homologous to a fragment of nucleic acid sequences encoding SEQ ID NO:38;

wherein H3HA-2 comprises a nucleic acid sequence selected from the group consisting of a nucleic acid sequence encoding SEQ ID NO:24, a nucleic acid sequence that is at least 95% homologous to nucleic acid sequences encoding SEQ ID NO:24; a fragment of nucleic acid sequences encoding SEQ ID NO:24; and a nucleic acid sequence that is at least 95% homologous to a fragment of nucleic acid sequences encoding SEQ ID NO:24.

9. The vaccine of claim 4, wherein H3HA-1 comprises a nucleic acid sequence selected from the group consisting of SEQ ID NO:37, a nucleic acid sequence that is at least 95% homologous to SEQ ID NO:37; a fragment of SEQ ID NO:37; and a nucleic acid sequence that is at least 95% homologous to a fragment of SEQ ID NO:37;

wherein H3HA-2 comprises a nucleic acid sequence selected from the group consisting of SEQ ID NO:23, a nucleic acid sequence that is at least 95% homologous to SEQ ID NO:23; a fragment of SEQ ID NO:23; and a nucleic acid sequence that is at least 95% homologous to a fragment of SEQ ID NO:23.

10. The vaccine of claim 5, wherein BHA-1 comprises a nucleic acid sequence selected from the group consisting of a nucleic acid sequence encoding SEQ ID NO:14, a nucleic acid sequence that is at least 95% homologous to nucleic acid sequences encoding SEQ ID NO:14; a fragment of nucleic acid sequences encoding SEQ ID NO:14; and a nucleic acid sequence that is at least 95% homologous to a fragment of nucleic acid sequences encoding SEQ ID NO:14;

wherein BHA-2 comprises a nucleic acid sequence selected from the group consisting of a nucleic acid sequence encoding SEQ ID NO:26, a nucleic acid sequence that is at least 95% homologous to nucleic acid sequences encoding SEQ ID NO:26; a fragment of nucleic acid sequences encoding SEQ ID NO:26; and a nucleic acid sequence that is at least 95% homologous to a fragment of nucleic acid sequences encoding SEQ ID NO:26.

11. The vaccine of claim 5, wherein BHA-1 comprises a nucleic acid sequence selected from the group consisting of SEQ ID NO:13, a nucleic acid sequence that is at least 95% homologous to SEQ ID NO:13; a fragment of SEQ ID NO:13; and a nucleic acid sequence that is at least 95% homologous to a fragment of SEQ ID NO:13;

wherein BHA-2 comprises a nucleic acid sequence selected from the group consisting of SEQ ID NO:25, a nucleic acid sequence that is at least 95% homologous to SEQ ID NO:25; a fragment of SEQ ID NO:25; and a nucleic acid sequence that is at least 95% homologous to a fragment of SEQ ID NO:25.

12. A method of inducing cross-reactivity against a variety of influenza strains in a mammal, the method comprising administering to the mammal in need thereof the vaccine of claim 1.

13. The method of claim 12, wherein each of the consensus hemagglutinin antigen is administered to the mammal separately.

14. The method of claim 12, wherein each of the consensus hemagglutinin antigen is administered to the mammal simultaneously.

15. The vaccine of claim 1, wherein said nucleic acid sequence is selected from the group consisting of: SEQ ID NO: 19, SEQ ID NO: 21, SEQ ID NO: 23, SEQ ID NO: 25, SEQ ID NO: 27, SEQ ID NO: 29, SEQ ID NO: 31, and SEQ ID NO: 33.

* * * * *